(12) United States Patent
Raghavan et al.

(10) Patent No.: US 8,168,649 B2
(45) Date of Patent: May 1, 2012

(54) NIACIN RECEPTOR AGONISTS, COMPOSITIONS CONTAINING SUCH COMPOUNDS AND METHODS OF TREATMENT

(75) Inventors: Subharekha Raghavan, Teaneck, NJ (US); Steven L. Colletti, Princeton Junction, NJ (US); Fa-Xiang Ding, Staten Island, NY (US); Hong Shen, West Windsor, NJ (US); James R. Tata, Westfield, NJ (US); Ashley Rouse Lins, Edison, NJ (US); Abigail Lee Smenton, Brooklyn, NY (US); Weichun Chen, Livingston, NJ (US); Darby Rye Schmidt, Clark, NJ (US); George Scott Tria, La Jolla, CA (US)

(73) Assignee: Merk Sharp & Dohme Corp., Rahway, NJ (US)

( * ) Notice: Subject to any disclaimer, the term of this patent is extended or adjusted under 35 U.S.C. 154(b) by 627 days.

(21) Appl. No.: 11/922,629

(22) PCT Filed: Jun. 26, 2006

(86) PCT No.: PCT/US2006/024740
§ 371 (c)(1),
(2), (4) Date: Dec. 20, 2007

(87) PCT Pub. No.: WO2007/002557
PCT Pub. Date: Jan. 4, 2007

(65) Prior Publication Data
US 2010/0144778 A1 Jun. 10, 2010

Related U.S. Application Data

(60) Provisional application No. 60/694,711, filed on Jun. 28, 2005.

(51) Int. Cl.
*A61K 31/44* (2006.01)
*A01N 43/40* (2006.01)
*A61K 31/19* (2006.01)
*A61K 31/165* (2006.01)

(52) U.S. Cl. ........ 514/292; 514/338; 514/364; 514/568; 514/617

(58) Field of Classification Search .................. None
See application file for complete search history.

(56) References Cited

U.S. PATENT DOCUMENTS
2004/0142377 A1 7/2004 Unett et al.
2006/0281810 A1 12/2006 Dehmlow et al.

FOREIGN PATENT DOCUMENTS

| WO | WO 94/15906 A1 | 7/1994 |
|---|---|---|
| WO | WO 98/56820 | 12/1998 |
| WO | WO 00/53581 | 9/2000 |
| WO | WO 01/36471 A2 | 5/2001 |
| WO | WO 01/77320 A2 | 10/2001 |
| WO | WO 02/084298 A2 | 10/2002 |
| WO | WO 03/018536 A1 | 3/2003 |
| WO | WO 2005/016867 A2 | 2/2005 |
| WO | WO 2005/016870 A1 | 2/2005 |
| WO | WO 2005/044816 A1 | 5/2005 |
| WO | WO 2005/077950 A2 | 8/2005 |
| WO | WO 2006/045565 A1 | 5/2006 |
| WO | WO 2006/052555 A2 | 5/2006 |
| WO | WO 2006/057922 A2 | 6/2006 |
| WO | WO 2006/069242 A2 | 6/2006 |
| WO | WO 2006/085108 A1 | 8/2006 |
| WO | WO 2006/085111 A1 | 8/2006 |
| WO | WO 2006/085112 A1 | 8/2006 |
| WO | WO 2006/085113 A2 | 8/2006 |
| WO | WO 2006/124490 A2 | 11/2006 |
| WO | WO 2007/002557 A1 | 1/2007 |

OTHER PUBLICATIONS

Han (Advances in Characterization of Pharmaceutical Hydrates. Trends in Bio/Pharmaceutical Industry, pp. 25-29. Mar. 2006).*
Schmidt et al (Bioorg Med Chem Lett 20:3426-3430, 2010).*
Danishefsky et al., J. Am. Chem. Soc., vol. 126, pp. 14358-14359 (2004).
Karpe, F., et al., Rapid Review, vol. 363, pp. 1892-1894 (2004).
Pike, N. B. et al., Current Opinion in Investigational Drugs, vol. 5, pp. 271-275 (2004).
van Herk et al., J. Med. Chem., vol. 46, pp. 3945-3951 (2003).
Vippagunta, Sudha R., Advanced Drug Delivery Reviews, vol. 48, pp. 3-26 (2001).

* cited by examiner

*Primary Examiner* — Brandon Fetterolf
*Assistant Examiner* — Craig Ricci
(74) *Attorney, Agent, or Firm* — Dianne Pecoraro; Catherine D. Fitch

(57) ABSTRACT

The present invention encompasses compounds of Formula (I): as well as pharmaceutically acceptable salts and hydrates thereof, that are useful for treating atherosclerosis, dyslipidemias and the like. Pharmaceutical compositions and methods of use are also included.

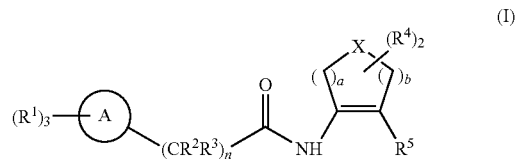

20 Claims, No Drawings

NIACIN RECEPTOR AGONISTS, COMPOSITIONS CONTAINING SUCH COMPOUNDS AND METHODS OF TREATMENT

PRIORITY CLAIM

This application is a §371 National Stage Application of PCT/US2006/024740, filed on Jun. 26, 2006, which claims priority from U.S. Provisional Application Ser. No. 60/694,711, filed on Jun. 28, 2005.

BACKGROUND OF THE INVENTION

The present invention relates to cycloalkene compounds, their derivatives, compositions containing such compounds and methods of treatment or prevention in a mammal relating to dyslipidemias. Dyslipidemia is a condition wherein serum lipids are abnormal. Elevated cholesterol and low levels of high density lipoprotein (HDL) are independent risk factors for atherosclerosis associated with a greater-than-normal risk of atherosclerosis and cardiovascular disease. Factors known to affect serum cholesterol include genetic predisposition, diet, body weight, degree of physical activity, age and gender. While cholesterol in normal amounts is a vital building block for cell membranes and essential organic molecules such as steroids and bile acids, cholesterol in excess is known to contribute to cardiovascular disease. For example, cholesterol, through its relationship with foam cells, is a primary component of plaque which collects in coronary arteries, resulting in the cardiovascular disease termed atherosclerosis.

Traditional therapies for reducing cholesterol include medications such as statins (which reduce production of cholesterol by the body). More recently, the value of nutrition and nutritional supplements in reducing blood cholesterol has received significant attention. For example, dietary compounds such as soluble fiber, vitamin E, soy, garlic, omega-3 fatty acids, and niacin have all received significant attention and research funding.

Niacin or nicotinic acid (pyridine-3-carboxylic acid) is a drug that reduces coronary events in clinical trials. It is commonly known for its effect in elevating serum levels of high density lipoproteins (HDL). Importantly, niacin also has a beneficial effect on other lipid profiles. Specifically, it reduces low density lipoproteins (LDL), very low density lipoproteins (VLDL), and triglycerides (TG). However, the clinical use of nicotinic acid is limited by a number of adverse side-effects including cutaneous vasodilation, sometimes called flushing.

Despite the attention focused on traditional and alternative means for controlling serum cholesterol, serum triglycerides, and the like, a significant portion of the population has total cholesterol levels greater than about 200 mg/dL, and are thus candidates for dyslipidemia therapy. There thus remains a need in the art for compounds, compositions and alternative methods of reducing total cholesterol, serum triglycerides, and the like, and raising HDL.

The present invention relates to compounds that have been discovered to have effects in modifying serum lipid levels.

The invention thus provides compositions for effecting reduction in total cholesterol and triglyceride concentrations and raising HDL, in accordance with the methods described.

Consequently one object of the present invention is to provide a nicotinic acid receptor agonist that can be used to treat dyslipidemias, atherosclerosis, diabetes, metabolic syndrome and related conditions while minimizing the adverse effects that are associated with niacin treatment.

Yet another object is to provide a pharmaceutical composition for oral use.

These and other objects will be apparent from the description provided herein.

SUMMARY OF THE INVENTION

A compound represented by formula I:

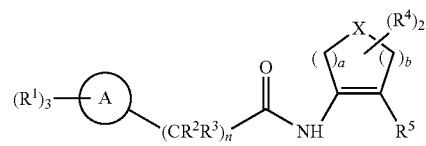

or a pharmaceutically acceptable salt or solvate thereof is disclosed wherein:

X represents $CH_2$, O, S, S(O), $SO_2$ or NH, such that when X represents NH, the nitrogen atom may be optionally substituted with $R^6$, $C(O)R^6$, or $SO_2R^6$, wherein:

$R^6$ represents $C_{1-3}$alkyl optionally substituted with 1-3 groups, 0-3 of which are halo, and 0-1 of which are selected from the group consisting of: $OC_{1-3}$alkyl, OH, $NH_2$, $NHC_{1-3}$alkyl, $N(C_{1-3}alkyl)_2$, CN, Hetcy, Aryl and HAR, said Aryl and HAR being further optionally substituted with 1-3 groups, 1-3 of which are halo, and 0-1 of which are selected from the group consisting of: OH, $NH_2$, $C_{1-3}$alkyl, $C_{1-3}$alkoxy, halo$C_{1-3}$alkyl and halo$C_{1-3}$alkoxy groups;

a and b are each integers 1, 2 or 3, such that the sum of a and b is 2, 3 or 4;

ring A represents a 6-10 membered aryl, a 5-13 membered heteroaryl or a partially aromatic heterocyclic group, said heteroaryl and partially aromatic heterocyclic group containing at least one heteroatom selected from O, S, S(O), $S(O)_2$ and N, and optionally containing 1 other heteroatom selected from O and S, and optionally containing 1-3 additional N atoms, with up to 5 heteroatoms being present;

each $R^2$ and $R^3$ is independently H, $C_{1-3}$alkyl, halo$C_{1-3}$alkyl, halo$C_{1-3}$alkoxy, OH or F;

n represents an integer of from 1 to 5;

each $R^4$ is H or is independently selected from halo and $R^6$;

$R^5$ represents —$CO_2H$,

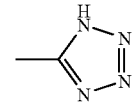

or —$C(O)NHSO_2R^e$ wherein $R^e$ represents $C_{1-4}$alkyl or phenyl, said $C_{1-4}$alkyl and phenyl each being optionally substituted with 1-3 groups, 1-3 of which are selected from halo and $C_{1-3}$alkyl, and 1-2 of which are selected from the group consisting of: $OC_{1-3}$alkyl, halo$C_{1-3}$alkyl, halo$C_{1-3}$alkoxy, OH, $NH_2$ and $NHC_{1-3}$alkyl;

and each $R^1$ is H or is independently selected from the group consisting of:

a) halo, OH, $CO_2H$, CN, $NH_2$, $S(O)_{0-2}R^e$, $C(O)R^e$, $OC(O)R^e$ and $CO_2R^e$, wherein $R^e$ is as previously defined;

b) $C_{1-6}$ alkyl and $OC_{1-6}$alkyl, said $C_{1-6}$alkyl and alkyl portion of $OC_{1-6}$alkyl being optionally substituted with 1-3 groups, 1-3 of which are halo and 1-2 of which are selected from: OH, $CO_2H$, $CO_2C_{1-4}$alkyl, $CO_2C_{1-4}$haloalkyl, $OCO_2C_{1-4}$alkyl, $NH_2$, $NHC_{1-4}$alkyl, $N(C_{1-4}alkyl)_2$, Hetcy and CN;

c) NHC$_{1-4}$alkyl and N(C$_{1-4}$alkyl)$_2$, the alkyl portions of which are optionally substituted as set forth in (b) above;

d) C(O)NH$_2$, C(O)NHC$_{1-4}$alkyl, C(O)N(C$_{1-4}$alkyl)$_2$, C(O)Hetcy, C(O)NHOC$_{1-4}$alkyl and C(O)N(C$_{1-4}$alkyl)(OC$_{1-4}$alkyl), the alkyl portions of which are optionally substituted as set forth in (b) above;

e) NR'C(O)R", NR'SO$_2$R", NR'CO$_2$R" and NR'C(O)NR"R'" wherein:

R' represents H, C$_{1-3}$alkyl or haloC$_{1-3}$alkyl,

R" represents (a) C$_{1-8}$alkyl optionally substituted with 1-4 groups, 0-4 of which are halo, and 0-1 of which are selected from the group consisting of: OC$_{1-6}$alkyl, OH, CO$_2$H, CO$_2$C$_{1-4}$alkyl, CO$_2$C$_{1-4}$haloalkyl, NH$_2$, NHC$_{1-4}$alkyl, N(C$_{1-4}$alkyl)$_2$, CN, Hetcy, Aryl and HAR, said Hetcy, Aryl and HAR being further optionally substituted with 1-3 halo, C$_{1-4}$alkyl, C$_{1-4}$alkoxy, haloC$_{1-4}$alkyl or haloC$_{1-4}$alkoxy groups;

(b) Hetcy, Aryl or HAR, each being optionally substituted with 1-3 members selected from the group consisting of: halo, C$_{1-4}$alkyl, C$_{1-4}$alkoxy, haloC$_{1-4}$alkyl and haloC$_{1-4}$alkoxy groups;

and R'" representing H or R";

f) phenyl or a 5-6 membered heteroaryl or a Hetcy group attached at any available ring atom and each being optionally substituted with 1-3 groups, 1-3 of which are selected from halo, C$_{1-3}$alkyl and haloC$_{1-3}$alkyl groups, and 1-2 of which are selected from OC$_{1-3}$alkyl and haloOC$_{1-3}$alkyl groups, and 0-1 of which is selected from the group consisting of:

i) OH; CO$_2$H; CN; NH$_2$ and S(O)$_{0-2}$R$^e$ wherein R$^e$ is as described above;

ii) NHC$_{1-4}$alkyl and N(C$_{1-4}$alkyl)$_2$, the alkyl portions of which are optionally substituted with 1-3 groups, 1-3 of which are halo and 1-2 of which are selected from: OH, CO$_2$H, CO$_2$C$_{1-4}$alkyl, CO$_2$C$_{1-4}$haloalkyl, NH$_2$, NHC$_{1-4}$alkyl, N(C$_{1-4}$alkyl)$_2$ and CN;

iii) C(O)NH$_2$, C(O)NHC$_{1-4}$alkyl, C(O)N(C$_{1-4}$alkyl)$_2$, C(O)NHOC$_{1-4}$alkyl and C(O)N(C$_{1-4}$alkyl)(OC$_{1-4}$alkyl), the alkyl portions of which are optionally substituted as set forth in b) above; and iv) NR'C(O)R", NR'SO$_2$R", NR'CO$_2$R" and NR'C(O)NR"R'" wherein R', R" and R'" are as described above.

DETAILED DESCRIPTION OF THE INVENTION

The invention is described herein in detail using the terms defined below unless otherwise specified.

"Alkyl", as well as other groups having the prefix "alk", such as alkoxy, alkanoyl and the like, means carbon chains which may be linear, branched, or cyclic, or combinations thereof, containing the indicated number of carbon atoms. If no number is specified, 1-6 carbon atoms are intended for linear and 3-7 carbon atoms for branched alkyl groups. Examples of alkyl groups include methyl, ethyl, propyl, isopropyl, butyl, sec- and tert-butyl, pentyl, hexyl, heptyl, octyl, nonyl and the like. Cycloalkyl is a subset of alkyl; if no number of atoms is specified, 3-7 carbon atoms are intended, forming 1-3 carbocyclic rings that are fused. "Cycloalkyl" also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl and the like. Haloalkoxy and haloOalkyl are used interchangeably and refer to halo substituted alkyl groups linked through the oxygen atom. Haloalkyl and haloalkoxy include mono-substituted as well as multiple substituted alkyl and alkoxy groups, up to perhalo substituted alkyl and alkoxy. For example, trifluoromethyl and trifluoromethoxy are included.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Aryl" (Ar) means mono- and bicyclic aromatic rings containing 6-10 carbon atoms. Examples of aryl include phenyl, naphthyl, indenyl and the like.

"Heteroaryl" (HAR) unless otherwise specified, means mono-, bicyclic and tricyclic aromatic ring systems containing at least one heteroatom selected from O, S, S(O), SO$_2$ and N, with each ring containing 5 to 6 atoms. HAR groups may contain from 5-14, preferably 5-13 atoms. Examples include, but are not limited to, pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, benzopyrazolyl, benzotriazolyl, furo(2,3-b)pyridyl, benzoxazinyl, tetrahydrohydroquinolinyl, tetrahydroisoquinolinyl, quinolyl, isoquinolyl, indolyl, dihydroindolyl, quinoxalinyl, quinazolinyl, naphthyridinyl, pteridinyl, 2,3-dihydrofuro(2,3-b)pyridyl and the like. Heteroaryl also includes aromatic carbocyclic or heterocyclic groups fused to heterocycles that are non-aromatic or partially aromatic, and optionally containing a carbonyl. Examples of additional heteroaryl groups include indolinyl, dihydrobenzofuranyl, dihydrobenzothiophenyl, dihydrobenzoxazolyl, and aromatic heterocyclic groups fused to cycloalkyl rings. Examples also include the following:

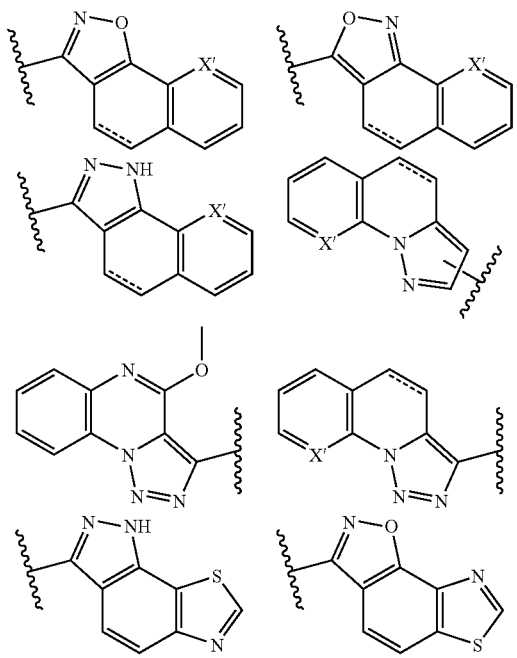

-continued

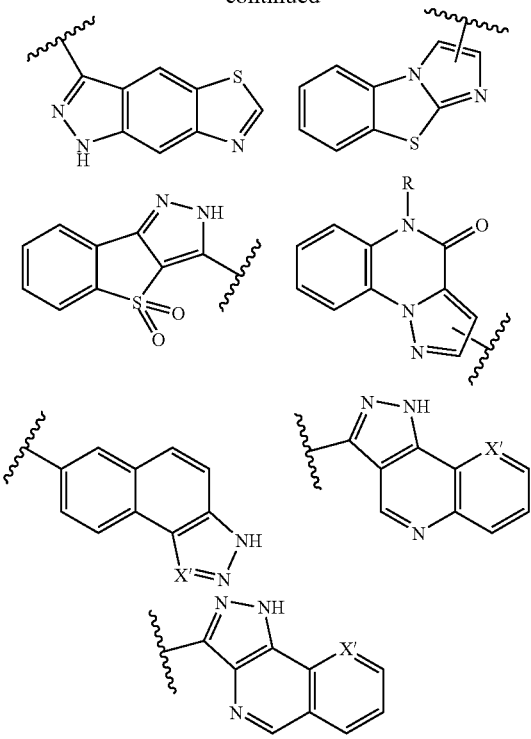

----- is a single or double bond
X' = CH or N
R = H or CH₃

Heteroaryl also includes such groups in charged form, e.g., pyridinium.

"Heterocyclyl" (Hetcy) unless otherwise specified, means mono- and bicyclic saturated and partially saturated rings and ring systems containing at least one heteroatom selected from N, S and O, each of said ring having from 3 to 10 atoms in which the point of attachment may be carbon or nitrogen. Examples of "heterocyclyl" include, but are not limited to, azetidinyl, pyrrolidinyl, piperidinyl, piperazinyl, imidazolidinyl, tetrahydrofuranyl, 1,4-dioxanyl, morpholinyl, thiomorpholinyl, tetrahydrothienyl and the like. Heterocycles can also exist in tautomeric forms, e.g., 2- and 4-pyridones. Heterocycles moreover includes such moieties in charged form, e.g., piperidinium.

"Halogen" (Halo) includes fluorine, chlorine, bromine and iodine.

The phrase "in the absence of substantial flushing" refers to the side effect that is often seen when nicotinic acid is administered in therapeutic amounts. The flushing effect of nicotinic acid usually becomes less frequent and less severe as the patient develops tolerance to the drug at therapeutic doses, but the flushing effect still occurs to some extent and can be transient. Thus, "in the absence of substantial flushing" refers to the reduced severity of flushing when it occurs, or fewer flushing events than would otherwise occur. Preferably, the incidence of flushing (relative to niacin) is reduced by at least about a third, more preferably the incidence is reduced by half, and most preferably, the flushing incidence is reduced by about two thirds or more. Likewise, the severity (relative to niacin) is preferably reduced by at least about a third, more preferably by at least half, and most preferably by at least about two thirds. Clearly a one hundred percent reduction in flushing incidence and severity is most preferable, but is not required.

One aspect of the invention relates to a compound represented by formula I:

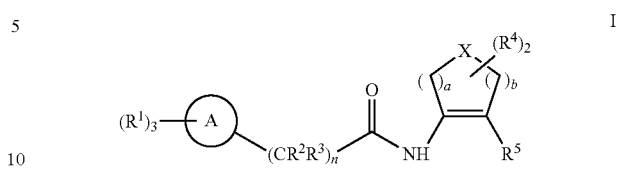

or a pharmaceutically acceptable salt or solvate thereof is disclosed wherein:

X represents $CH_2$, O, S, S(O), $SO_2$ or NH, such that when X represents NH, the nitrogen atom may be optionally substituted with $R^6$, $C(O)R^6$, or $SO_2R^6$, wherein:

$R^6$ represents $C_{1-3}$alkyl optionally substituted with 1-3 groups, 0-3 of which are halo, and 0-1 of which are selected from the group consisting of: $OC_{1-3}$alkyl, OH, $NH_2$, $NHC_{1-3}$alkyl, $N(C_{1-3}alkyl)_2$, CN, Hetcy, Aryl and HAR, said Aryl and HAR being further optionally substituted with 1-3 groups, 1-3 of which are halo, and 0-1 of which are selected from the group consisting of OH, $NH_2$, $C_{1-3}$alkyl, $C_{1-3}$alkoxy, $haloC_{1-3}$alkyl and $haloC_{1-3}$alkoxy groups;

a and b are each integers 1, 2 or 3, such that the sum of a and b is 2, 3 or 4;

ring A represents a 6-10 membered aryl, a 5-13 membered heteroaryl or a partially aromatic heterocyclic group, said heteroaryl and partially aromatic heterocyclic group containing at least one heteroatom selected from O, S, S(O), $S(O)_2$ and N, and optionally containing 1 other heteroatom selected from O and S, and optionally containing 1-3 additional N atoms, with up to 5 heteroatoms being present;

each $R^2$ and $R^3$ is independently H, $C_{1-3}$alkyl, $haloC_{1-3}$alkyl, $OC_{1-3}$alkyl, $haloC_{1-3}$alkoxy, OH or F;

n represents an integer of from 1 to 5;

each $R^4$ is H or is independently selected from halo and $R^6$;

$R^5$ represents —$CO_2H$,

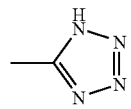

or —$C(O)NHSO_2R^e$ wherein $R^e$ represents $C_{1-4}$alkyl or phenyl, said $C_{1-4}$alkyl and phenyl each being optionally substituted with 1-3 groups, 1-3 of which are selected from halo and $C_{1-3}$alkyl, and 1-2 of which are selected from the group consisting of: $OC_{1-3}$alkyl, $haloC_{1-3}$alkyl, $haloC_{1-3}$alkoxy, OH, $NH_2$ and $NHC_{1-3}$alkyl;

and each $R^1$ is H or is independently selected from the group consisting of:

a) halo, OH, $CO_2H$, CN, $NH_2$, $S(O)_{0-2}R^e$, $C(O)R^e$, $OC(O)R^e$ and $CO_2R^e$, wherein $R^e$ is as previously defined;

b) $C_{1-6}$ alkyl and $OC_{1-6}$alkyl, said $C_{1-6}$alkyl and alkyl portion of $OC_{1-6}$alkyl being optionally substituted with 1-3 groups, 1-3 of which are halo and 1-2 of which are selected from: OH, $CO_2H$, $CO_2C_{1-4}$alkyl, $CO_2C_{1-4}$haloalkyl, $OCO_2C_{1-4}$alkyl, $NH_2$, $NHC_{1-4}$alkyl, $N(C_{1-4}alkyl)_2$, Hetcy and CN;

c) $NHC_{1-4}$alkyl and $N(C_{1-4}alkyl)_2$, the alkyl portions of which are optionally substituted as set forth in (b) above;

d) $C(O)NH_2$, $C(O)NHC_{1-4}$alkyl, $C(O)N(C_{1-4}alkyl)_2$, $C(O)$Hetcy, $C(O)NHOC_{1-4}$alkyl and $C(O)N(C_{1-4}alkyl)(OC_{1-4}alkyl)$, the alkyl portions of which are optionally substituted as set forth in (b) above;

e) NR'C(O)R", NR'SO$_2$R", NR'CO$_2$R" and NR'C(O)NR"R'" wherein:

R' represents H, C$_{1-3}$alkyl or haloC$_{1-3}$alkyl,

R" represents (a) C$_{1-8}$alkyl optionally substituted with 1-4 groups, 0-4 of which are halo, and 0-1 of which are selected from the group consisting of: OC$_{1-6}$alkyl, OH, CO$_2$H, CO$_2$C$_{1-4}$alkyl, CO$_2$C$_{1-4}$haloalkyl, NH$_2$, NHC$_{1-4}$alkyl, N(C$_{1-4}$alkyl)$_2$, CN, Hetcy, Aryl and HAR, said Hetcy, Aryl and HAR being further optionally substituted with 1-3 halo, C$_{1-4}$alkyl, C$_{1-4}$alkoxy, haloC$_{1-4}$alkyl or haloC$_{1-4}$alkoxy groups; or (b) Hetcy, Aryl or HAR, each being optionally substituted with 1-3 members selected from the group consisting of halo, C$_{1-4}$alkyl, C$_{1-4}$alkoxy, haloC$_{1-4}$alkyl and haloC$_{1-4}$alkoxy groups;

and R'" representing H or R";

f) phenyl or a 5-6 membered heteroaryl or a Hetcy group attached at any available ring atom and each being optionally substituted with 1-3 groups, 1-3 of which are selected from halo, C$_{1-3}$alkyl and haloC$_{1-3}$alkyl groups, and 1-2 of which are selected from OC$_{1-3}$alkyl and haloOC$_{1-3}$alkyl groups, and 0-1 of which is selected from the group consisting of i) OH; CO$_2$H; CN; NH$_2$ and S(O)$_{0-2}$R$^e$ wherein R$^e$ is as described above;

ii) NHC$_{1-4}$alkyl and N(C$_{1-4}$alkyl)$_2$, the alkyl portions of which are optionally substituted with 1-3 groups, 1-3 of which are halo and 1-2 of which are selected from: OH, CO$_2$H, CO$_2$C$_{1-4}$alkyl, CO$_2$C$_{1-4}$haloalkyl, NH$_2$, NHC$_{1-4}$alkyl, N(C$_{1-4}$alkyl)$_2$ and CN;

iii) C(O)NH$_2$, C(O)NHC$_{1-4}$alkyl, C(O)N(C$_{1-4}$alkyl)$_2$, C(O)NHOC$_{1-4}$alkyl and C(O)N(C$_{1-4}$alkyl)(OC$_{1-4}$alkyl), the alkyl portions of which are optionally substituted as set forth in b) above; and iv) NR'C(O)R", NR'SO$_2$R", NR'CO$_2$R" and NR'C(O)NR"R'" wherein R', R" and R'" are as described above.

One aspect of the invention that is of interest relates to a compound of formula I wherein up to 4 R$^2$ and R$^3$ moieties are selected from the group consisting of: C$_{1-3}$alkyl, haloC$_{1-3}$alkyl, OC$_{1-3}$alkyl, haloC$_{1-3}$alkoxy, OH and F, and any remaining R$^2$ and R$^3$ moieties represent H.

Another subset of compounds that is of interest relates to compounds of formula I wherein ring A is a phenyl or naphthyl group, a 5-6 membered monocyclic heteroaryl group or a 9-13 membered bicyclic or tricyclic heteroaryl group. Within this subset of compounds, all other variables are as defined with respect to formula I.

More particularly, a subset of compounds that is of interest relates to compounds of formula I wherein ring A is selected from the group consisting of: phenyl; naphthyl;

HAR which is a member selected from the group consisting of: pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, benzopyrazolyl, benzotriazolyl, furo(2,3-b)pyridyl, benzoxazinyl, tetrahydrohydroquinolinyl, tetrahydroisoquinolinyl, quinolyl, isoquinolyl, indolyl, dihydroindolyl, quinoxalinyl, quinazolinyl, naphthyridinyl, pteridinyl, 2,3-dihydrofuro(2,3-b)pyridyl indolinyl, dihydrobenzofuranyl, dihydrobenzothiophenyl, dihydrobenzoxazolyl, or a member selected from the group consisting of:

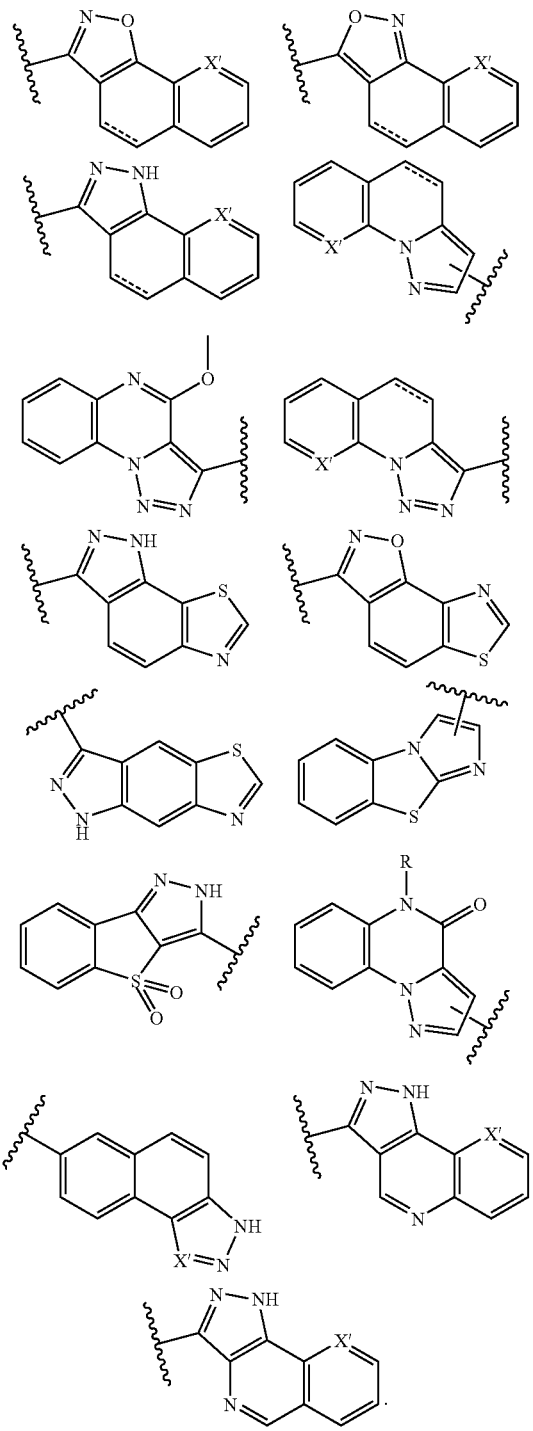

----- is a single or double bond
X' = CH or N
R = H or CH$_3$

Even more particularly, an aspect of the invention that is of interest relates to a compound of formula I wherein ring A is selected from the group consisting of: phenyl; naphthyl;

HAR which is a member selected from the group consisting of: isoxazolyl, pyrazolyl, oxazolyl, oxadiazolyl, thiazolyl, triazolyl, thienyl, benzothiazolyl, or a member selected from the group consisting of:

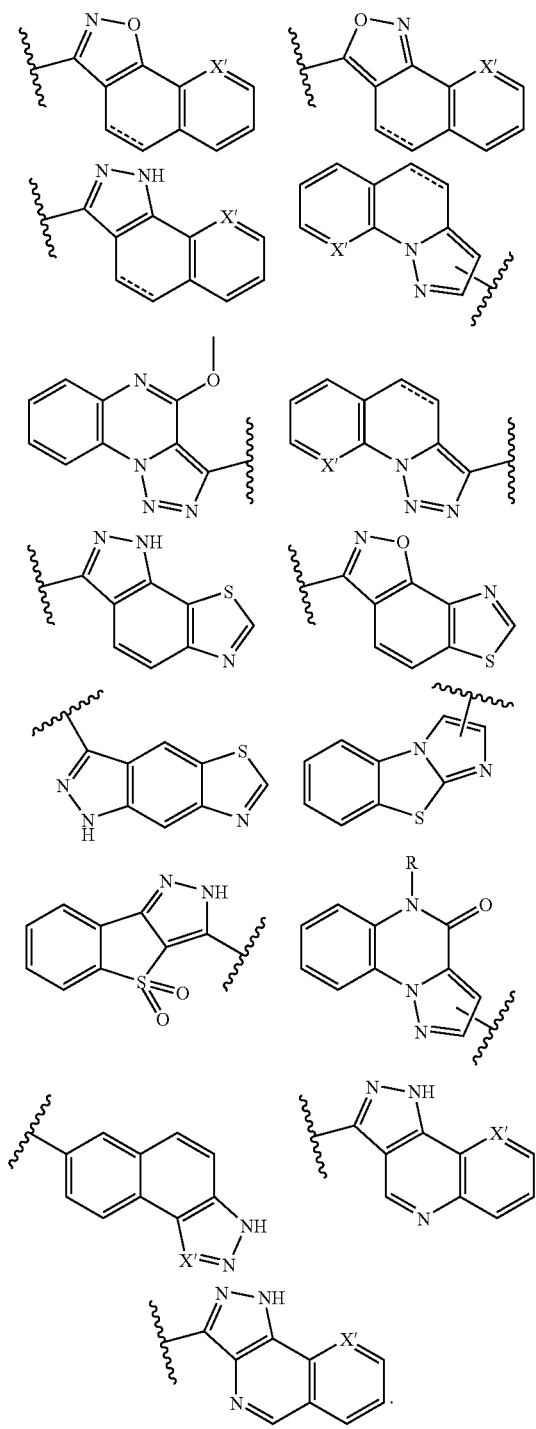

----- is a single or double bond
X' = CH or N
R = H or CH₃

Within this subset of compounds, all other variables are as defined with respect to formula I.

Another subset of compounds that is of interest relates to compounds of formula I wherein each R¹ is H or is selected from the group consisting of:

a) halo, OH, CN, NH₂ and S(O)₀₋₂Rᵉ wherein Rᵉ is methyl or phenyl optionally substituted with 1-3 halo groups;

b) $C_{1-3}$alkyl and O$C_{1-3}$alkyl, each being optionally substituted with 1-3 groups, 1-3 of which are halo and 1-2 of which are selected from: OH, NH₂, NH$C_{1-4}$alkyl and CN;

c) NR'SO₂R" and NR'C(O)NR"R''' wherein:

R' represents H, $C_{1-3}$alkyl or halo$C_{1-4}$alkyl,

R" represents (a) $C_{1-8}$alkyl optionally substituted with 1-4 groups, 0-4 of which are halo, and 0-1 of which are selected from the group consisting of: O$C_{1-6}$alkyl, OH, CO₂H, CO₂$C_{1-4}$alkyl, CO₂$C_{1-4}$haloalkyl, OCO₂$C_{1-4}$alkyl, NH₂, NH$C_{1-4}$alkyl, N($C_{1-4}$alkyl)₂, CN, Hetcy, Aryl and HAR, said Hetcy, Aryl and HAR being further optionally substituted with 1-3 groups selected from: halo, $C_{1-4}$alkyl, $C_{1-4}$alkoxy, halo$C_{1-4}$alkyl and halo$C_{1-4}$alkoxy;

(b) Hetcy, Aryl or HAR, said Aryl and HAR being optionally substituted with 1-3 groups selected from: halo, $C_{1-4}$alkyl, $C_{1-4}$alkoxy, halo$C_{1-4}$alkyl and halo$C_{1-4}$alkoxyl;

and R''' representing H or R"; and d) phenyl or a 5-6 membered heteroaryl or a heterocyclic group attached at any available point and being optionally substituted with 1-3 groups, 1-3 of which are halo, $C_{1-3}$alkyl or halo$C_{1-3}$alkyl groups, 1-2 of which are O$C_{1-3}$alkyl or haloO$C_{1-3}$alkyl groups, and 1 of which is selected from the group consisting of i) OH; CO₂H; CN; NH₂ and S(O)₀₋₂Rᵉ wherein Rᵉ is as described above;

ii) NH$C_{1-4}$alkyl, the alkyl portion of which is optionally substituted with 1-3 groups, 1-3 of which are halo and 1 of which is selected from: OH, CO₂H, CO₂$C_{1-4}$alkyl, CO₂$C_{1-4}$haloalkyl, NH₂, NH$C_{1-4}$alkyl, N($C_{1-4}$ alkyl)₂ and CN;

iii) C(O)NH₂, C(O)NH$C_{1-4}$alkyl and C(O)N($C_{1-4}$alkyl)₂, the alkyl portions of which are optionally substituted as set forth in (b) above; and iv) NR'C(O)R" and NR'SO₂R" wherein R' and R" are as described above. Within this subset of compounds, all other variables are as defined with respect to formula I.

In particular, another subset of compounds that is of interest relates to compounds of formula I wherein each R¹ is H or is selected from the group consisting of:

a) halo, OH, CN and NH₂;

b) $C_{1-3}$alkyl and O$C_{1-3}$alkyl, each being optionally substituted with 1-3 groups, 1-3 of which are halo and 1-2 of which are selected from: OH, NH₂, NH$C_{1-4}$alkyl and CN;

c) phenyl or a 5-6 membered heteroaryl or a heterocyclic group attached at any available point and being optionally substituted with 1-3 groups, 1-3 of which are halo, $C_{1-3}$alkyl or halo$C_{1-3}$alkyl groups, 1-2 of which are O$C_{1-3}$alkyl or haloO$C_{1-3}$alkyl groups, and 1 of which is selected from the group consisting of:

i) OH, CN and NH₂. Within this subset of compounds, all other variables are as defined with respect to formula I.

Another subset of compounds that is of interest relates to compounds of formula I wherein a and b are 1 or 2 such that the sum of a and b is 2 or 3. Within this subset of compounds, all other variables are as defined with respect to formula I.

Another subset of compounds that is of interest relates to compounds of formula I wherein X represents O, S, N or CH₂. Within this subset of compounds, all other variables are as defined with respect to formula I.

More particularly, another subset of compounds that is of interest relates to compounds of formula I wherein X represents O or CH₂. Within this subset of compounds, all other variables are as defined with respect to formula I.

Another subset of compounds that is of interest relates to compounds of formula I wherein R² and R³ are independently H, $C_{1-3}$alkyl, OH or halo$C_{1-3}$alkyl. Within this subset of compounds, all other variables are as defined with respect to formula I.

More particularly, another subset of compounds that is of interest relates to compounds of formula I wherein $R^2$ and $R^3$ are independently H, $C_{1-3}$alkyl or halo$C_{1-3}$alkyl. Within this subset of compounds, all other variables are as defined with respect to formula I.

More particularly, a subset of compounds that is of interest relates to compounds of formula I wherein $R^2$ and $R^3$ are independently H or methyl. Within this subset of compounds, all other variables are as defined with respect to formula I.

Another subset of compounds that is of interest relates to compounds of formula I wherein n represents an integer of from 2 to 4. Within this subset of compounds, all other variables are as defined with respect to formula I.

More particularly, a subset of compounds that is of interest relates to compounds of formula I wherein n is 2. Within this subset of compounds, all other variables are as defined with respect to formula I.

Another subset of compounds that is of interest relates to compounds of formula I wherein each $R^4$ is H or is independently selected from the group consisting of halo, $C_{1-3}$alkyl optionally substituted with 1-3 halo groups and 0-1 $OC_{1-3}$alkyl groups. Within this subset of compounds, all other variables are as defined with respect to formula I.

Another subset of compounds that is of interest relates to compounds of formula I wherein each $R^4$ is H or is independently selected from halo or $C_{1-3}$alkyl optionally substituted with 1-3 halo groups. Within this subset of compounds, all other variables are as defined with respect to formula I.

Another subset of compounds that is of interest relates to compounds of formula I wherein $R^5$ represents —$CO_2H$. Within this subset of compounds, all other variables are as defined with respect to formula I.

A particular subset of compounds that is of interest relates to compounds of formula I or a pharmaceutically acceptable salt or solvate thereof wherein:
ring A is a phenyl or naphthyl group, a 5-6 membered monocyclic heteroaryl group or a 9-13 membered bicyclic or tricyclic heteroaryl group;
each $R^1$ is H or is selected from the group consisting of:
a) halo, OH, CN, $NH_2$ and $S(O)_{0-2}R^e$ wherein $R^e$ is methyl or phenyl optionally substituted with 1-3 halo groups;
b) $C_{1-3}$ alkyl and $OC_{1-3}$alkyl, each being optionally substituted with 1-3 groups, 1-3 of which are halo and 1-2 of which are selected from: OH, $NH_2$, $NHC_{1-4}$alkyl and CN;
c) $NR'SO_2R''$ and $NR'C(O)NR''R'''$ wherein:
R' represents H, $C_{1-3}$alkyl or halo$C_{1-3}$alkyl,
R" represents (a) $C_{1-8}$alkyl optionally substituted with 1-4 groups, 0-4 of which are halo, and 0-1 of which are selected from the group consisting of: $OC_{1-6}$alkyl, OH, $CO_2H$, $CO_2C_{1-4}$alkyl, $CO_2C_{1-4}$haloalkyl, $OCO_2C_{1-4}$alkyl, $NH_2$, $NHC_{1-4}$alkyl, $N(C_{1-4}$alkyl$)_2$, CN, Hetcy, Aryl and HAR,
said Hetcy, Aryl and HAR being further optionally substituted with 1-3 halo, $C_{1-4}$alkyl, $C_{1-4}$alkoxy, halo$C_{1-4}$alkyl and halo$C_{1-4}$alkoxy groups;
(b) Hetcy, Aryl or HAR, said Aryl and HAR being further optionally substituted with 1-3 halo, $C_{1-4}$alkyl, $C_{1-4}$alkoxy, halo$C_{1-4}$alkyl and halo$C_{1-4}$alkoxy groups;
and R'" representing H or R"; and
d) phenyl or a 5-6 membered heteroaryl or a heterocyclic group attached at any available point and being optionally substituted with 1-3 groups, 1-3 of which are halo, $C_{1-3}$alkyl or halo$C_{1-3}$alkyl groups, 1-2 of which are $OC_{1-3}$alkyl or haloO$C_{1-3}$alkyl groups, and 1 of which is selected from the group consisting of:
i) OH; $CO_2H$; CN; $NH_2$; $S(O)_{0-2}R^e$ wherein $R^e$ is as described above;
ii) $NHC_{1-4}$alkyl the alkyl portion of which is optionally substituted with 1-3 groups, 1-3 of which are halo and 1 of which is selected from: OH, $CO_2H$, $CO_2C_{1-4}$alkyl, $CO_2C_{1-4}$haloalkyl, $NH_2$, $NHC_{1-4}$alkyl, $N(C_{1-4}$alkyl$)_2$ and CN;
iii) $C(O)NH_2$, $C(O)NHC_{1-4}$alkyl, $C(O)N(C_{1-4}$alkyl$)_2$, the alkyl portions of which are optionally substituted as set forth in (b) above; and
iv) $NR'C(O)R''$ and $NR'SO_2R''$ wherein R' and R" are as described above;
a and b are 1 or 2 such that the sum of a and b is 2 or 3;
X represents O or $CH_2$;
$R^2$ and $R^3$ are independently H, OH, $C_{1-3}$alkyl or halo$C_{1-3}$alkyl;
n represents 2;
$R^4$ is H or is independently selected from the group consisting of: halo, $C_{1-3}$alkyl optionally substituted with 1-3 halo groups or 0-1 $OC_{1-3}$alkyl groups; and
$R^5$ represents —$CO_2H$.

A more particular subset of compounds that is of interest relates to compounds of formula I or a pharmaceutically acceptable salt of solvate thereof wherein:
ring A is selected from the group consisting of:

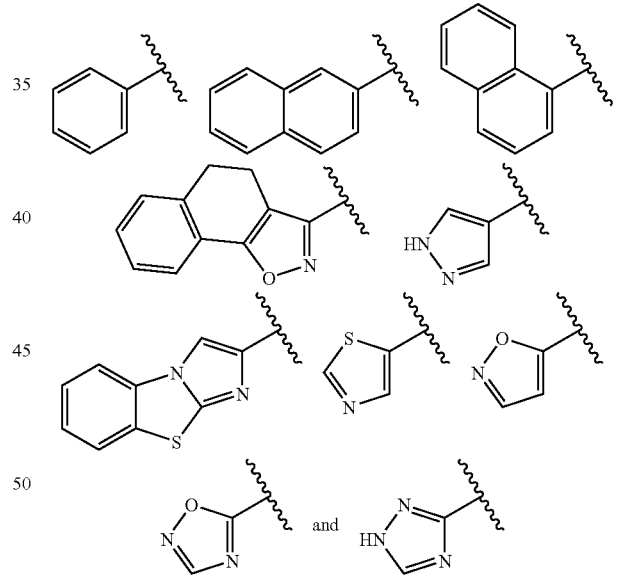

each $R^1$ is independently H, $CH_3$, phenyl, 4-hydroxy-phenyl, OH, 2-hydroxy-phenyl, 3-hydroxy-phenyl, 3-amino-phenyl, 2,3-dihydro-benzofuran-6-yl, 2-chloro-4-hydroxy-phenyl, 1H-pyrazol-4-yl, 5-hydroxy-pyridin-2-yl, 4-hydroxy-pyrazol-1-yl, 1H-[1,2,3]triazol-4-yl, or 5-fluoro-pyridin-2-yl;
a and b are 1 or 2 such that the sum of a and b is 2 or 3;
X represents $CH_2$;
each $R^2$ and $R^3$ is independently H, OH or $CH_3$;
n represents 2;
$R^4$ is H, $CH_3$, $CH_2CH_3$, $CF_3$ or $CH_2OCH_3$; and
$R^5$ represents —$CO_2H$.

Representative examples of species that are of interest are shown below in Table I. Within this subset of compounds, all other variables are as originally defined with respect to formula I.
TABLE 1
Compound 1
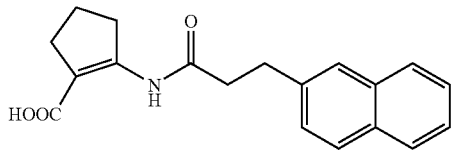
Compound 2
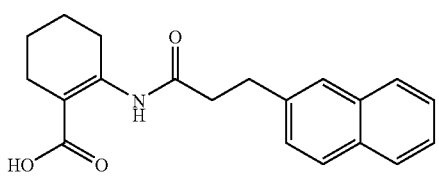
Compound 3
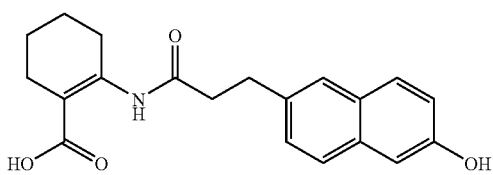
Compound 4
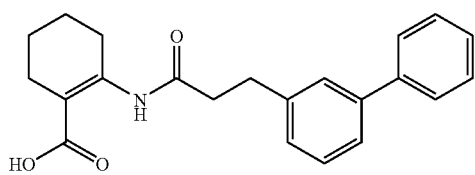
Compound 5
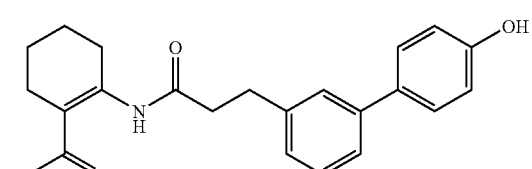
Compound 6
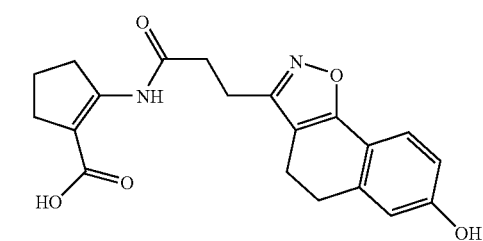
TABLE 1-continued
Compound 7
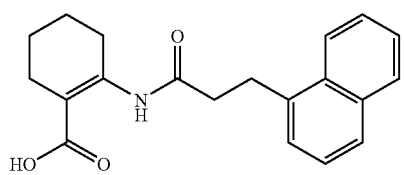
Compound 8
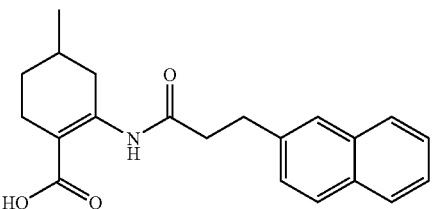
Compound 9
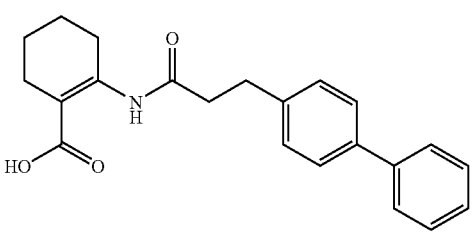
Compound 10
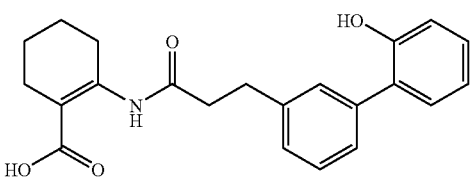
Compound 11
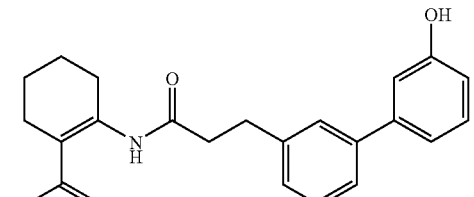
Compound 12
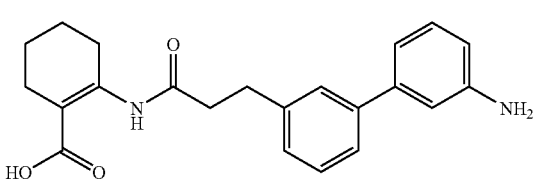

TABLE 1-continued
Compound 13
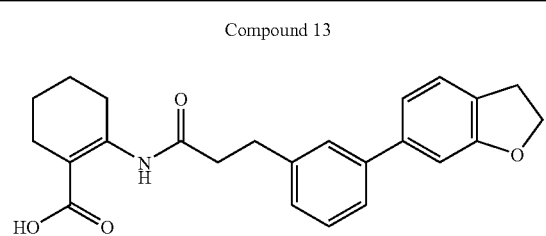
Compound 14
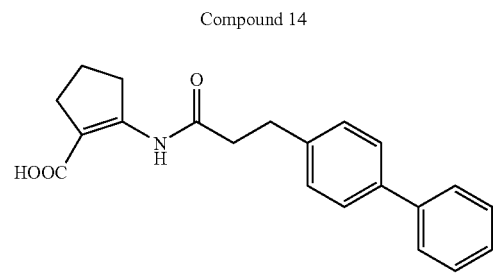
Compound 15
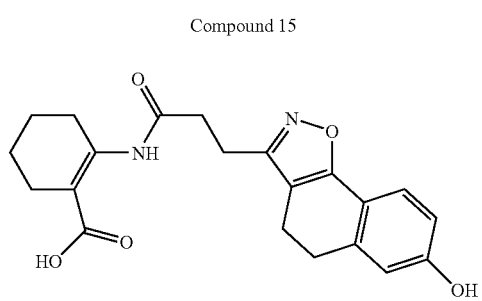
Compound 16
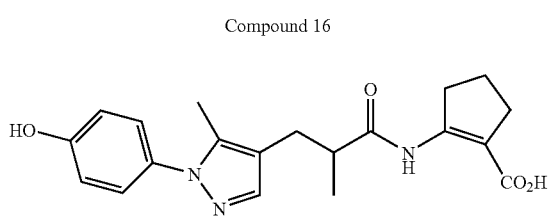
Compound 17
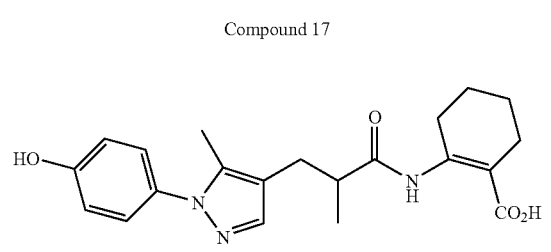
Compound 18
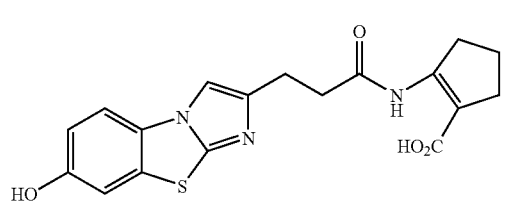
TABLE 1-continued
Compound 19
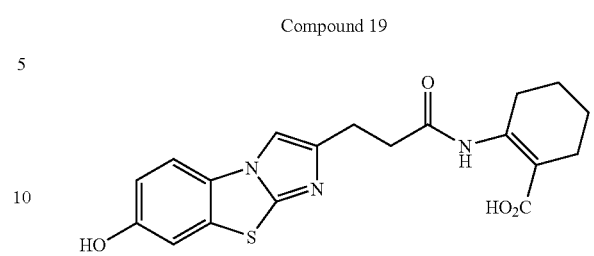
Compound 20
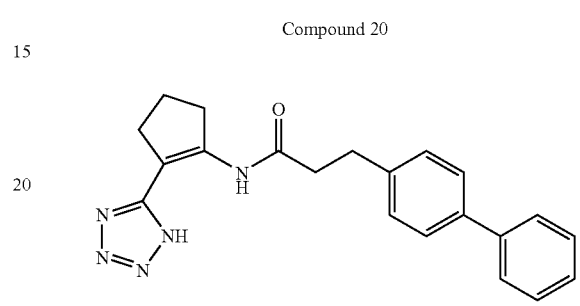
Compound 21
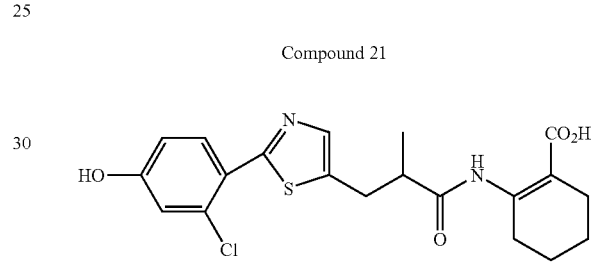
Compound 22
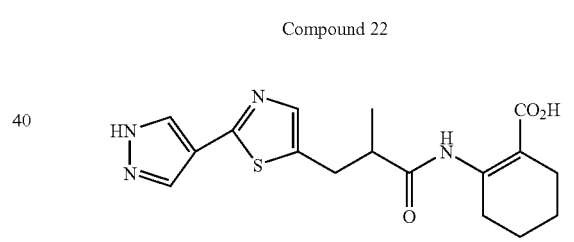
Compound 23
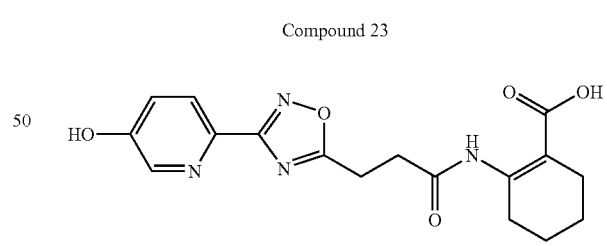
Compound 24
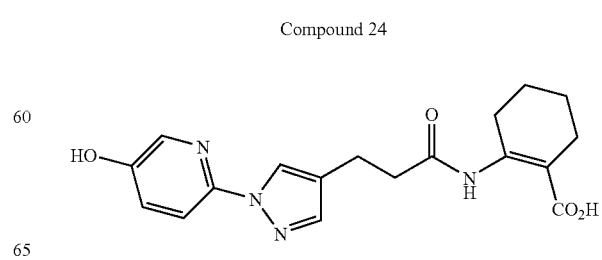

TABLE 1-continued
Compound 25
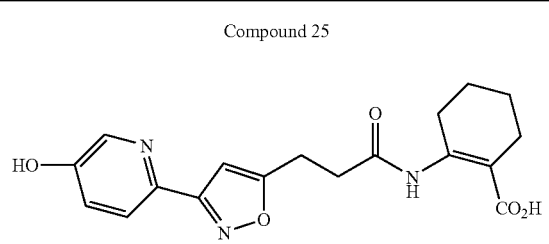
Compound 26
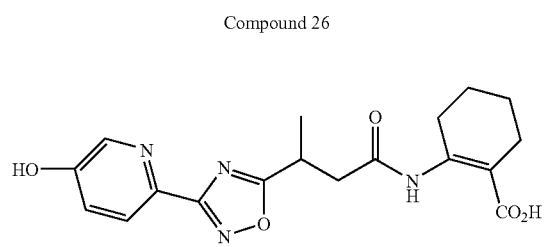
Compound 27
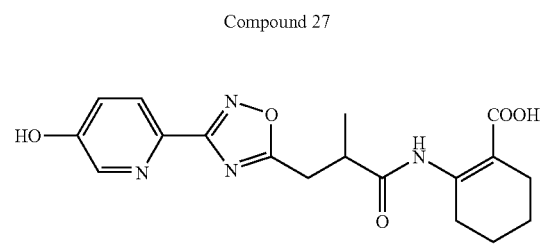
Compound 28
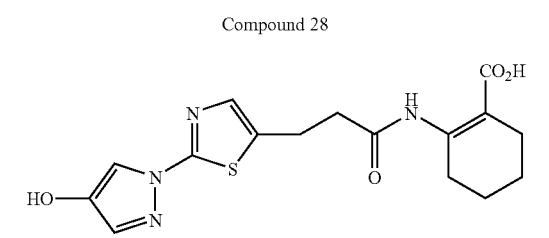
Compound 29
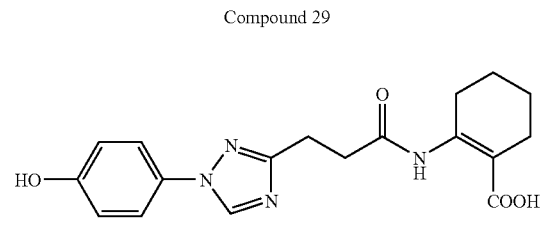
Compound 30
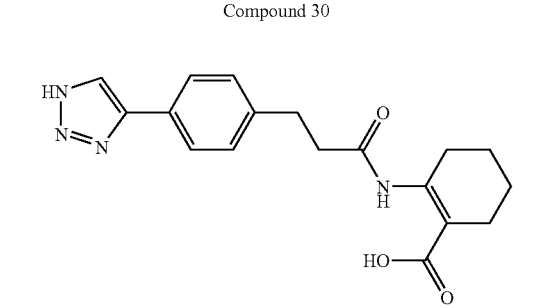
TABLE 1-continued
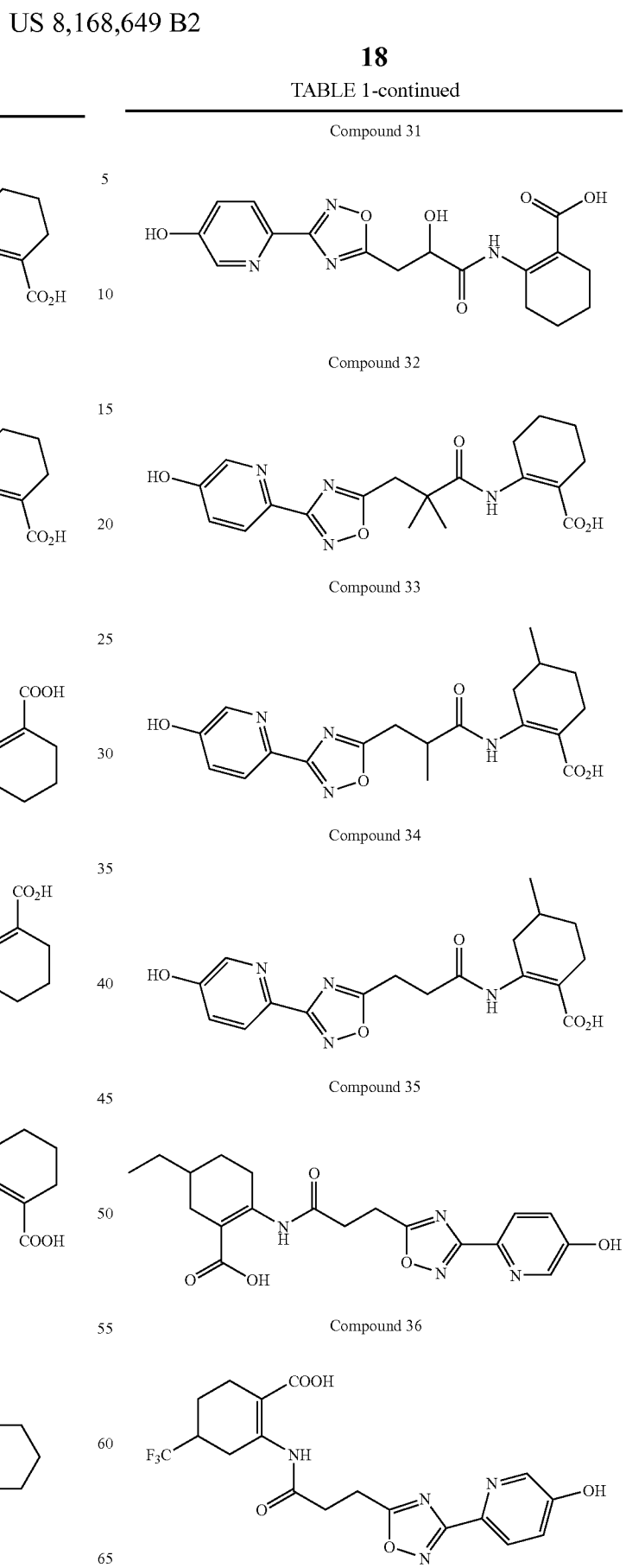

TABLE 1-continued

Compound 37

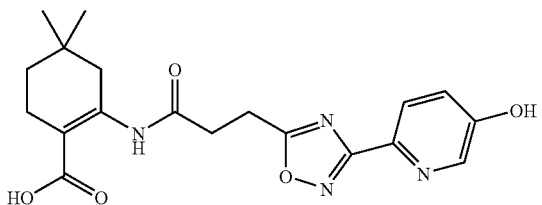

Compound 38

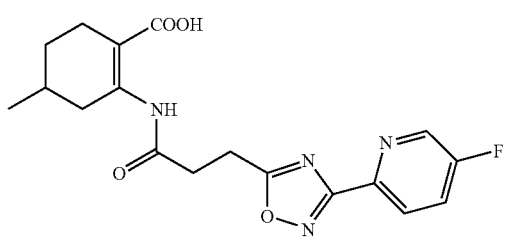

Compound 39

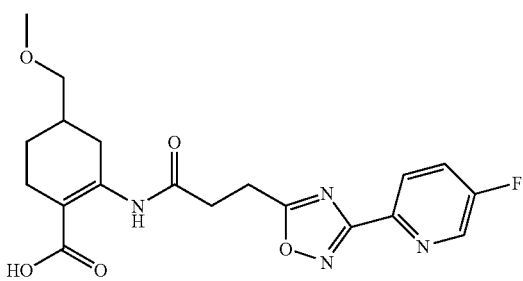

Compound 40

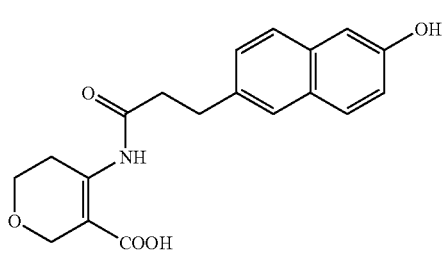

Compound 41

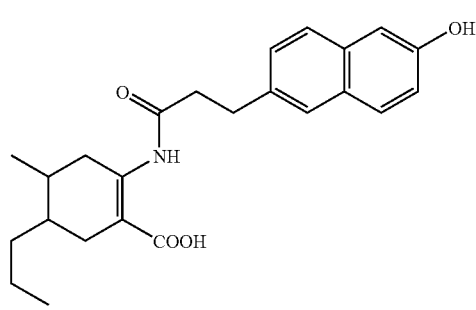

Pharmaceutically acceptable salts and solvates thereof are included as well.

Many of the compounds of formula I contain asymmetric centers and can thus occur as racemates and racemic mixtures, single enantiomers, diastereomeric mixtures and individual diastereomers. All such isomeric forms are included.

Moreover, chiral compounds possessing one stereocenter of general formula I, may be resolved into their enantiomers in the presence of a chiral environment using methods known to those skilled in the art. Chiral compounds possessing more than one stereocenter may be separated into their diastereomers in an achiral environment on the basis of their physical properties using methods known to those skilled in the art. Single diastereomers that are obtained in racemic form may be resolved into their enantiomers as described above.

If desired, racemic mixtures of compounds may be separated so that individual enantiomers are isolated. The separation can be carried out by methods well known in the art, such as the coupling of a racemic mixture of compounds of Formula I to an enantiomerically pure compound to form a diastereomeric mixture, which is then separated into individual diastereomers by standard methods, such as fractional crystallization or chromatography. The coupling reaction is often the formation of salts using an enantiomerically pure acid or base. The diasteromeric derivatives may then be converted to substantially pure enantiomers by cleaving the added chiral residue from the diastereomeric compound.

The racemic mixture of the compounds of Formula I can also be separated directly by chromatographic methods utilizing chiral stationary phases, which methods are well known in the art.

Alternatively, enantiomers of compounds of the general Formula I may be obtained by stereoselective synthesis using optically pure starting materials or reagents.

Some of the compounds described herein exist as tautomers, which have different points of attachment for hydrogen accompanied by one or more double bond shifts. For example, a ketone and its enol form are keto-enol tautomers. Or for example, a 2-hydroxyquinoline can reside in the tautomeric 2-quinolone form. The individual tautomers as well as mixtures thereof are included.

Dosing Information

The dosages of compounds of formula I or a pharmaceutically acceptable salt or solvate thereof vary within wide limits. The specific dosage regimen and levels for any particular patient will depend upon a variety of factors including the age, body weight, general health, sex, diet, time of administration, route of administration, rate of excretion, drug combination and the severity of the patient's condition. Consideration of these factors is well within the purview of the ordinarily skilled clinician for the purpose of determining the therapeutically effective or prophylactically effective dosage amount needed to prevent, counter, or arrest the progress of the condition. Generally, the compounds will be administered in amounts ranging from as low as about 0.01 mg/day to as high as about 2000 mg/day, in single or divided doses. A representative dosage is about 0.1 mg/day to about 1 g/day. Lower dosages can be used initially, and dosages increased to further minimize any untoward effects. It is expected that the compounds described herein will be administered on a daily basis for a length of time appropriate to treat or prevent the medical condition relevant to the patient, including a course of therapy lasting months, years or the life of the patient.

Combination Therapy

One or more additional active agents may be administered with the compounds described herein. The additional active agent or agents can be lipid modifying compounds or agents having other pharmaceutical activities, or agents that have both lipid-modifying effects and other pharmaceutical activities. Examples of additional active agents which may be employed include but are not limited to HMG-CoA reductase inhibitors, which include statins in their lactonized or dihydroxy open acid forms and pharmaceutically acceptable salts and esters thereof, including but not limited to lovastatin (see U.S. Pat. No. 4,342,767), simvastatin (see U.S. Pat. No. 4,444,784), dihydroxy open-acid simvastatin, particularly the ammonium or calcium salts thereof, pravastatin, particularly the sodium salt thereof (see U.S. Pat. No. 4,346,227), fluvastatin particularly the sodium salt thereof (see U.S. Pat. No. 5,354,772), atorvastatin, particularly the calcium salt thereof (see U.S. Pat. No. 5,273,995), pitavastatin also referred to as NK-104 (see PCT international publication number WO 97/23200) and rosuvastatin, also known as CRESTOR®; see U.S. Pat. No. 5,260,440); HMG-CoA synthase inhibitors; squalene epoxidase inhibitors; squalene synthetase inhibitors (also known as squalene synthase inhibitors), acyl-coenzyme A: cholesterol acyltransferase (ACAT) inhibitors including selective inhibitors of ACAT-1 or ACAT-2 as well as dual inhibitors of ACAT-1 and -2; microsomal triglyceride transfer protein (MTP) inhibitors; endothelial lipase inhibitors; bile acid sequestrants; LDL receptor inducers; platelet aggregation inhibitors, for example glycoprotein IIb/IIIa fibrinogen receptor antagonists and aspirin; human peroxisome proliferator activated receptor gamma (PPAR-gamma) agonists including the compounds commonly referred to as glitazones for example pioglitazone and rosiglitazone and, including those compounds included within the structural class known as thiazolidine diones as well as those PPAR-gamma agonists outside the thiazolidine dione structural class; PPAR-alpha agonists such as clofibrate, fenofibrate including micronized fenofibrate, and gemfibrozil; PPAR dual alpha/gamma agonists; vitamin $B_6$ (also known as pyridoxine) and the pharmaceutically acceptable salts thereof such as the HCl salt; vitamin $B_{12}$ (also known as cyanocobalamin); folic acid or a pharmaceutically acceptable salt or ester thereof such as the sodium salt and the methylglucamine salt; anti-oxidant vitamins such as vitamin C and E and beta carotene; beta-blockers; angiotensin II antagonists such as losartan; angiotensin converting enzyme inhibitors such as enalapril and captopril; renin inhibitors, calcium channel blockers such as nifedipine and diltiazem; endothelin antagonist; agents that enhance ABCA1 gene expression; cholesteryl ester transfer protein (CETP) inhibiting compounds, 5-lipoxygenase activating protein (FLAP) inhibiting compounds, 5-lipoxygenase (5-LO) inhibiting compounds, farnesoid X receptor (FXR) ligands including both antagonists and agonists; Liver X Receptor (LXR)-alpha ligands, LXR-beta ligands, bisphosphonate compounds such as alendronate sodium; cyclooxygenase-2 inhibitors such as rofecoxib and celecoxib; and compounds that attenuate vascular inflammation.

Cholesterol absorption inhibitors can also be used in the present invention. Such compounds block the movement of cholesterol from the intestinal lumen into enterocytes of the small intestinal wall, thus reducing serum cholesterol levels. Examples of cholesterol absorption inhibitors are described in U.S. Pat. Nos. 5,846,966, 5,631,365, 5,767,115, 6,133,001, 5,886,171, 5,856,473, 5,756,470, 5,739,321, 5,919,672, and in PCT application Nos. WO 00/63703, WO 00/60107, WO 00/38725, WO 00/34240, WO 00/20623, WO 97/45406, WO 97/16424, WO 97/16455, and WO 95/08532. The most notable cholesterol absorption inhibitor is ezetimibe, also known as 1-(4-fluorophenyl)-3(R)-[3(S)-(4-fluorophenyl)-3-hydroxypropyl)]-4(S)-(4-hydroxyphenyl)-2-azetidinone, described in U.S. Pat. Nos. 5,767,115 and 5,846,966.

Therapeutically effective amounts of cholesterol absorption inhibitors include dosages of from about 0.01 mg/kg to about 30 mg/kg of body weight per day, preferably about 0.1 mg/kg to about 15 mg/kg.

For diabetic patients, the compounds used in the present invention can be administered with conventional diabetic medications. For example, a diabetic patient receiving treatment as described herein may also be taking insulin or an oral antidiabetic medication. One example of an oral antidiabetic medication useful herein is metformin.

In the event that these niacin receptor agonists induce some degree of vasodilation, it is understood that the compounds of formula I may be co-dosed with a vasodilation suppressing agent. Consequently, one aspect of the methods described herein relates to the use of a compound of formula I or a pharmaceutically acceptable salt or solvate thereof in combination with a compound that reduces flushing. Conventional compounds such as aspirin, ibuprofen, naproxen, indomethacin, other NSAIDs, COX-2 selective inhibitors and the like are useful in this regard, at conventional doses. Alternatively, DP antagonists are useful as well. Doses of the DP receptor antagonist and selectivity are such that the DP antagonist selectively modulates the DP receptor without substantially modulating the CRTH2 receptor. In particular, the DP receptor antagonist ideally has an affinity at the DP receptor (i.e., $K_i$) that is at least about 10 times higher (a numerically lower $K_i$; value) than the affinity at the CRTH2 receptor. Any compound that selectively interacts with DP according to these guidelines is deemed "DP selective". This is in accordance with US Published Application No. 2004/0229844A1 published on Nov. 18, 2004, incorporated herein by reference.

Dosages for DP antagonists as described herein, that are useful for reducing or preventing the flushing effect in mammalian patients, particularly humans, include dosages ranging from as low as about 0.01 mg/day to as high as about 100 mg/day, administered in single or divided daily doses. Preferably the dosages are from about 0.1 mg/day to as high as about 1.0 g/day, in single or divided daily doses.

Examples of compounds that are particularly useful for selectively antagonizing DP receptors and suppressing the flushing effect include the following:

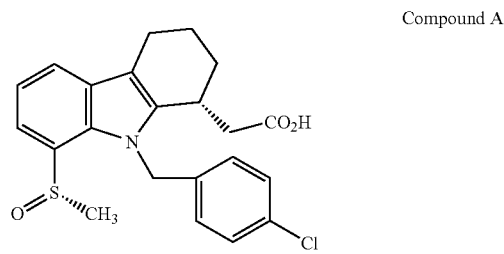

Compound A

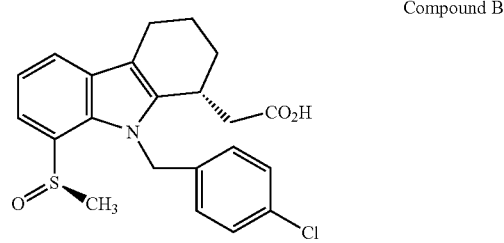

Compound B

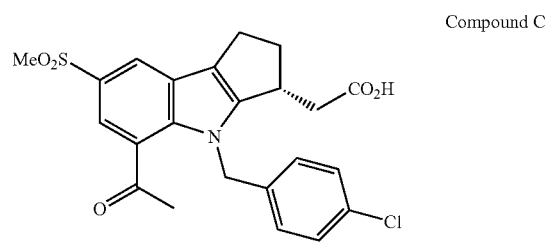

Compound C

Compound D
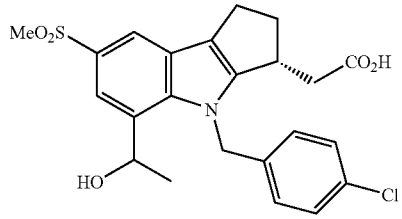
Compound E
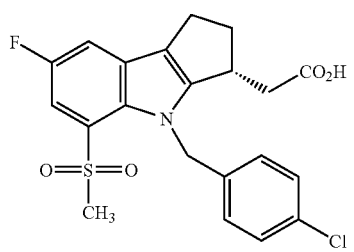
Compound F
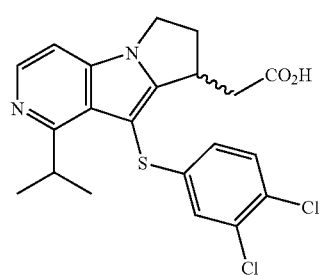
Compound G
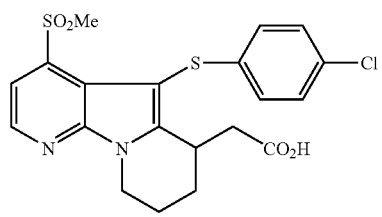
Compound H
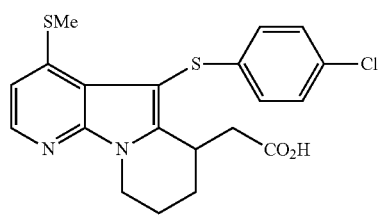
Compound I
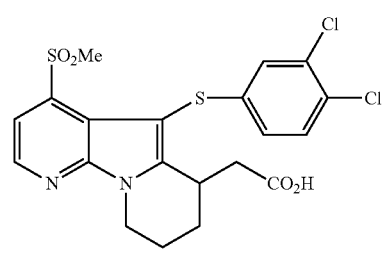
Compound J
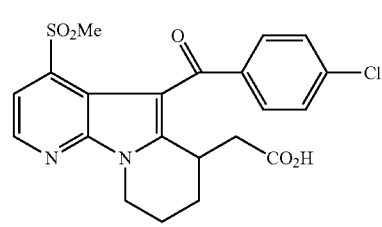
Compound K
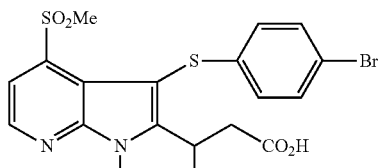
Compound L
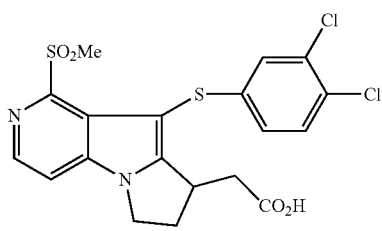
Compound M
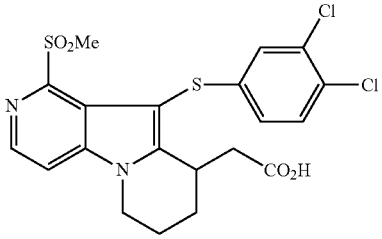
Compound N
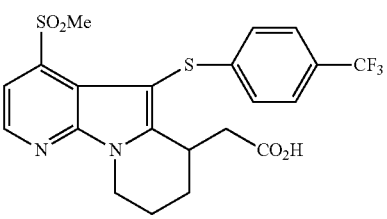
Compound O
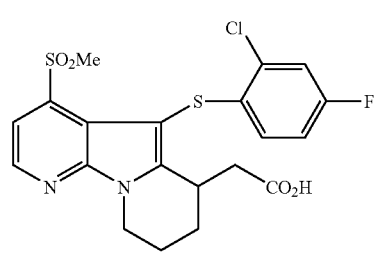
Compound P
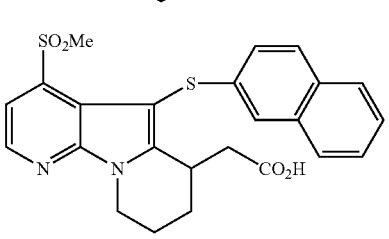
Compound Q
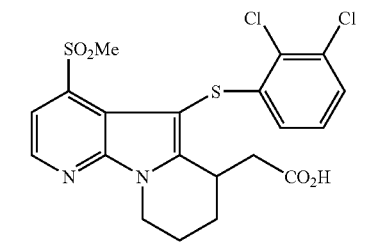

Compound R
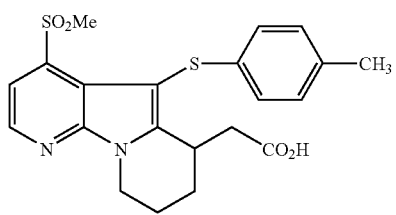
Compound S
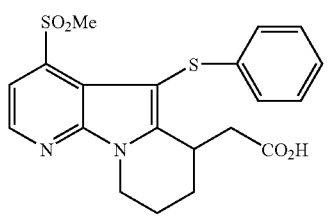
Compound T
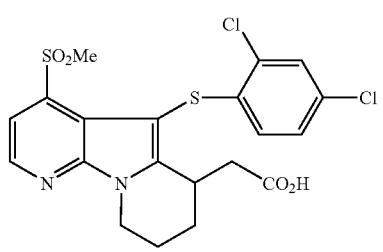
Compound U
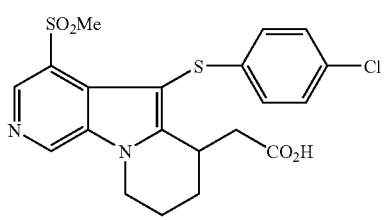
Compound V
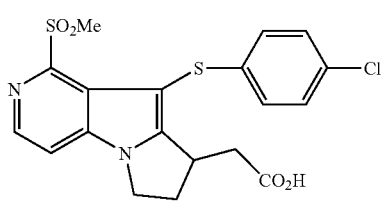
Compound W
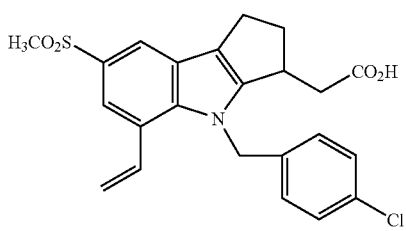
Compound X
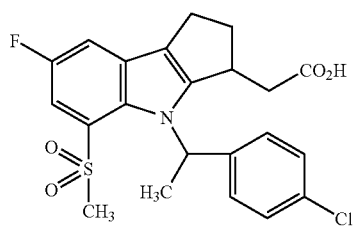
Compound Y
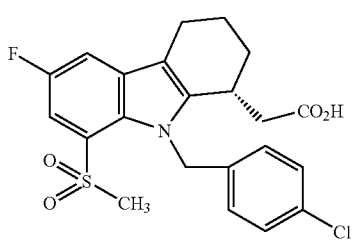
Compound Z
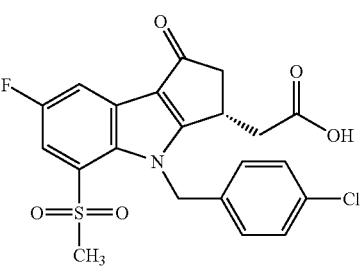
Compound AA
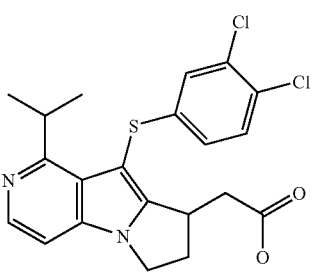
Compound AB
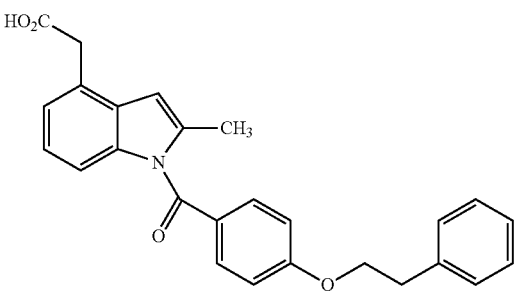
Compound AC
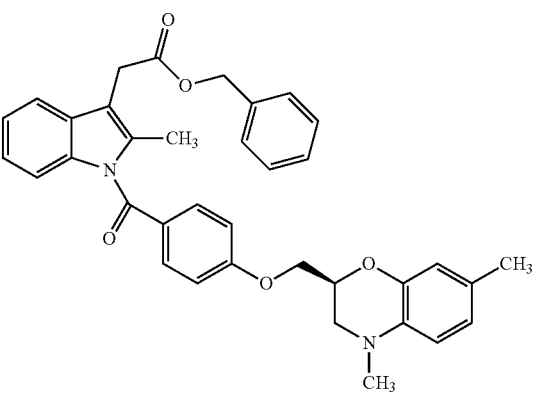

-continued

Compound AD
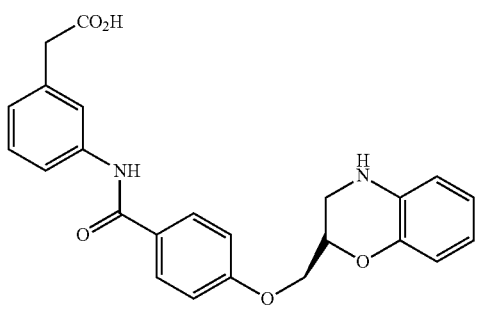

Compound AE
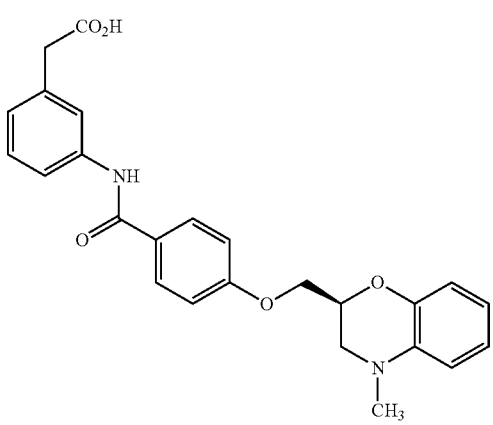

Compound AF
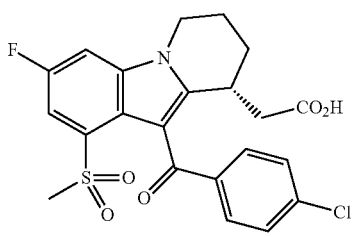

Compound AG
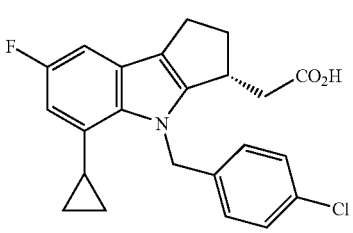

Compound AH
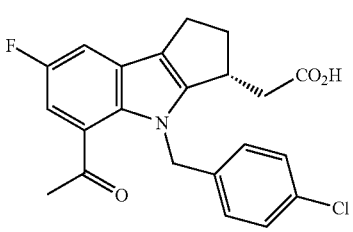

-continued

Compound AI
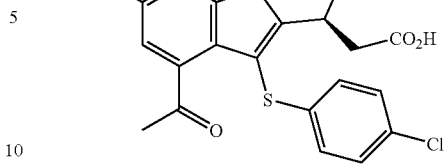

Compound AJ
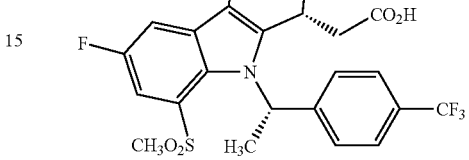

as well as the pharmaceutically acceptable salts and solvates thereof.

The compound of formula I or a pharmaceutically acceptable salt or solvate thereof and the DP antagonist can be administered together or sequentially in single or multiple daily doses, e.g., bid, tid or qid, without departing from the invention. If sustained release is desired, such as a sustained release product showing a release profile that extends beyond 24 hours, dosages may be administered every other day. However, single daily doses are preferred. Likewise, morning or evening dosages can be utilized.

Salts and Solvates

Salts and solvates of the compounds of formula I are also included in the present invention, and numerous pharmaceutically acceptable salts and solvates of nicotinic acid are useful in this regard. Alkali metal salts, in particular, sodium and potassium, form salts that are useful as described herein. Likewise alkaline earth metals, in particular, calcium and magnesium, form salts that are useful as described herein. Various salts of amines, such as ammonium and substituted ammonium compounds also form salts that are useful as described herein. Similarly, solvated forms of the compounds of formula I are useful within the present invention. Examples include the hemihydrate, mono-, di-, tri- and sesquihydrate.

The compounds of the invention also include esters that are pharmaceutically acceptable, as well as those that are metabolically labile. Metabolically labile esters include $C_{1-4}$ alkyl esters, preferably the ethyl ester. Many prodrug strategies are known to those skilled in the art. One such strategy involves engineered amino acid anhydrides possessing pendant nucleophiles, such as lysine, which can cyclize upon themselves, liberating the free acid. Similarly, acetone-ketal diesters, which can break down to acetone, an acid and the active acid, can be used.

The compounds used in the present invention can be administered via any conventional route of administration. The preferred route of administration is oral.

Pharmaceutical Compositions

The pharmaceutical compositions described herein are generally comprised of a compound of formula I or a pharmaceutically acceptable salt or solvate thereof, in combination with a pharmaceutically acceptable carrier.

Examples of suitable oral compositions include tablets, capsules, troches, lozenges, suspensions, dispersible powders or granules, emulsions, syrups and elixirs. Examples of carrier ingredients include diluents, binders, disintegrants, lubricants, sweeteners, flavors, colorants, preservatives, and the like. Examples of diluents include, for example, calcium carbonate, sodium carbonate, lactose, calcium phosphate and sodium phosphate. Examples of granulating and disintegrants include corn starch and alginic acid. Examples of binding agents include starch, gelatin and acacia. Examples of lubricants include magnesium stearate, calcium stearate, stearic acid and talc. The tablets may be uncoated or coated by known techniques. Such coatings may delay disintegration and thus, absorption in the gastrointestinal tract and thereby provide a sustained action over a longer period.

One embodiment of the invention that is of interest is a tablet or capsule that is comprised of a compound of formula I or a pharmaceutically acceptable salt or solvate thereof in an amount ranging from about 0.1 mg to about 1000 mg, in combination with a pharmaceutically acceptable carrier.

In another embodiment of the invention, a compound of formula I or a pharmaceutically acceptable salt or solvate thereof is combined with another therapeutic agent and the carrier to form a fixed combination product. This fixed combination product may be a tablet or capsule for oral use.

More particularly, in another embodiment of the invention, a compound of formula I or a pharmaceutically acceptable salt or solvate thereof (about 0.1 to about 1000 mg) and the second therapeutic agent (about 0.1 to about 500 mg) are combined with the pharmaceutically acceptable carrier, providing a tablet or capsule for oral use.

Sustained release over a longer period of time may be particularly important in the formulation. A time delay material such as glyceryl monostearate or glyceryl distearate may be employed. The dosage form may also be coated by the techniques described in the U.S. Pat. Nos. 4,256,108; 4,166,452 and 4,265,874 to form osmotic therapeutic tablets for controlled release.

Other controlled release technologies are also available and are included herein. Typical ingredients that are useful to slow the release of nicotinic acid in sustained release tablets include various cellulosic compounds, such as methylcellulose, ethylcellulose, propylcellulose, hydroxypropylcellulose, hydroxyethylcellulose, hydroxypropylmethylcellulose, microcrystalline cellulose, starch and the like. Various natural and synthetic materials are also of use in sustained release formulations. Examples include alginic acid and various alginates, polyvinyl pyrrolidone, tragacanth, locust bean gum, guar gum, gelatin, various long chain alcohols, such as cetyl alcohol and beeswax.

Optionally and of even more interest is a tablet as described above, comprised of a compound of formula I or a pharmaceutically acceptable salt or solvate thereof, and further containing an HMG Co-A reductase inhibitor, such as simvastatin or atorvastatin. This particular embodiment optionally contains the DP antagonist as well.

Typical release time frames for sustained release tablets in accordance with the present invention range from about 1 to as long as about 48 hours, preferably about 4 to about 24 hours, and more preferably about 8 to about 16 hours.

Hard gelatin capsules constitute another solid dosage form for oral use. Such capsules similarly include the active ingredients mixed with carrier materials as described above. Soft gelatin capsules include the active ingredients mixed with water-miscible solvents such as propylene glycol, PEG and ethanol, or an oil such as peanut oil, liquid paraffin or olive oil.

Aqueous suspensions are also contemplated as containing the active material in admixture with excipients suitable for the manufacture of aqueous suspensions. Such excipients include suspending agents, for example sodium carboxymethylcellulose, methylcellulose, hydroxypropylmethylcellulose, sodium alginate, polyvinylpyrrolidone, tragacanth and acacia; dispersing or wetting agents, e.g., lecithin; preservatives, e.g., ethyl, or n-propyl para-hydroxybenzoate, colorants, flavors, sweeteners and the like.

Dispersible powders and granules suitable for preparation of an aqueous suspension by the addition of water provide the active ingredients in admixture with a dispersing or wetting agent, suspending agent and one or more preservatives. Suitable dispersing or wetting agents and suspending agents are exemplified by those already mentioned above.

Syrups and elixirs may also be formulated.

More particularly, a pharmaceutical composition that is of interest is a sustained release tablet that is comprised of a compound of formula I or a pharmaceutically acceptable salt or solvate thereof, and a DP receptor antagonist that is selected from the group consisting of compounds A through AJ in combination with a pharmaceutically acceptable carrier.

Yet another pharmaceutical composition that is of more interest is comprised of a compound of formula I or a pharmaceutically acceptable salt or solvate thereof and a DP antagonist compound selected from the group consisting of compounds A, B, D, E, X, AA, AF, AG, AH, AI and AJ, in combination with a pharmaceutically acceptable carrier.

Yet another pharmaceutical composition that is of more particular interest relates to a sustained release tablet that is comprised of a compound of formula I or a pharmaceutically acceptable salt or solvate thereof, a DP receptor antagonist selected from the group consisting of compounds A, B, D, E, X, AA, AF, AG, AH, AI and AJ, and simvastatin or atorvastatin in combination with a pharmaceutically acceptable carrier.

The term "composition", in addition to encompassing the pharmaceutical compositions described above, also encompasses any product which results, directly or indirectly, from the combination, complexation or aggregation of any two or more of the ingredients, active or excipient, or from dissociation of one or more of the ingredients, or from other types of reactions or interactions of one or more of the ingredients. Accordingly, the pharmaceutical composition of the present invention encompasses any composition made by admixing or otherwise combining the compounds, any additional active ingredient(s), and the pharmaceutically acceptable excipients.

Another aspect of the invention relates to the use of a compound of formula I or a pharmaceutically acceptable salt or solvate thereof and a DP antagonist in the manufacture of a medicament. This medicament has the uses described herein.

More particularly, another aspect of the invention relates to the use of a compound of formula I or a pharmaceutically acceptable salt or solvate thereof, a DP antagonist and an HMG Co-A reductase inhibitor, such as simvastatin, in the manufacture of a medicament. This medicament has the uses described herein.

Compounds of the present invention have anti-hyperlipidemic activity, causing reductions in LDL-C, triglycerides, lipoprotein (a), free fatty acids and total cholesterol, and increases in HDL-C. Consequently, the compounds of the present invention are useful in treating dyslipidemias. The present invention thus relates to the treatment, prevention or reversal of atherosclerosis and the other diseases and conditions described herein, by administering a compound of formula I or a pharmaceutically acceptable salt or solvate in an amount that is effective for treating, preventing or reversing said condition. This is achieved in humans by administering a compound of formula I or a pharmaceutically acceptable salt or solvate thereof in an amount that is effective to treat or prevent said condition, while preventing, reducing or minimizing flushing effects in terms of frequency and/or severity.

One aspect of the invention that is of interest relates to a compound in accordance with formula I or a pharmaceutically acceptable salt or solvate thereof for use in a method of treatment of the human or animal body by therapy.

Another aspect of the invention that is of interest relates to a compound in accordance with formula I or a pharmaceutically acceptable salt or solvate thereof for use in a method for the treatment of atherosclerosis, dyslipidemia, diabetes, metabolic syndrome or a related condition in the human or animal body by therapy.

More particularly, an aspect of the invention that is of interest is a method of treating atherosclerosis in a human patient in need of such treatment comprising administering to the patient a compound of formula I or a pharmaceutically acceptable salt or solvate thereof in an amount that is effective for treating atherosclerosis in the absence of substantial flushing.

Another aspect of the invention that is of interest relates to a method of raising serum HDL levels in a human patient in need of such treatment, comprising administering to the patient a compound of formula I or a pharmaceutically acceptable salt or solvate thereof in an amount that is effective for raising serum HDL levels.

Another aspect of the invention that is of interest relates to a method of treating dyslipidemia in a human patient in need of such treatment comprising administering to the patient a compound of formula I or a pharmaceutically acceptable salt or solvate thereof in an amount that is effective for treating dyslipidemia.

Another aspect of the invention that is of interest relates to a method of reducing serum VLDL or LDL levels in a human patient in need of such treatment, comprising administering to the patient a compound of formula I or a pharmaceutically acceptable salt or solvate thereof in an amount that is effective for reducing serum VLDL or LDL levels in the patient in the absence of substantial flushing.

Another aspect of the invention that is of interest relates to a method of reducing serum triglyceride levels in a human patient in need of such treatment, comprising administering to the patient a compound of formula I or a pharmaceutically acceptable salt or solvate thereof in an amount that is effective for reducing serum triglyceride levels.

Another aspect of the invention that is of interest relates to a method of reducing serum Lp(a) levels in a human patient in need of such treatment, comprising administering to the patient a compound of formula I or a pharmaceutically acceptable salt or solvate thereof in an amount that is effective for reducing serum Lp(a) levels. As used herein Lp(a) refers to lipoprotein (a).

Another aspect of the invention that is of interest relates to a method of treating diabetes, and in particular, type 2 diabetes, in a human patient in need of such treatment comprising administering to the patient a compound of formula I or a pharmaceutically acceptable salt or solvate thereof in an amount that is effective for treating diabetes.

Another aspect of the invention that is of interest relates to a method of treating metabolic syndrome in a human patient in need of such treatment comprising administering to the patient a compound of formula I or a pharmaceutically acceptable salt or solvate thereof in an amount that is effective for treating metabolic syndrome.

Another aspect of the invention that is of particular interest relates to a method of treating atherosclerosis, dyslipidemias, diabetes, metabolic syndrome or a related condition in a human patient in need of such treatment, comprising administering to the patient a compound of formula I or a pharmaceutically acceptable salt or solvate thereof and a DP receptor antagonist, said combination being administered in an amount that is effective to treat atherosclerosis, dyslipidemia, diabetes or a related condition in the absence of substantial flushing.

Another aspect of the invention that is of particular interest relates to the methods described above wherein the DP receptor antagonist is selected from the group consisting of compounds A through AJ and the pharmaceutically acceptable salts and solvates thereof.

Methods of Synthesis for Compounds of Formula I

Compounds of Formula I have been prepared by the following representative reaction schemes. It is understood that similar reagents, conditions or other synthetic approaches to these structure classes are conceivable to one skilled in the art of organic synthesis. Therefore these reaction schemes should not be construed as limiting the scope of the invention. All substituents are as defined above unless indicated otherwise.

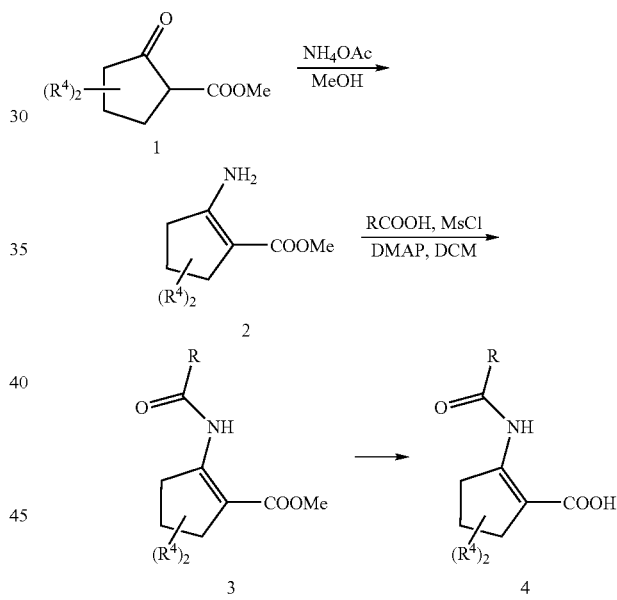

Scheme 1

Compounds of Formula I, where X represents $CH_2$, a and b equal 1 and RCOOH represents:

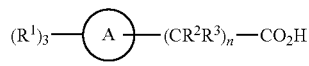

can be prepared as illustrated in Scheme 1 by treatment of commercially available methyl 2-oxocyclopentane-1-carboxylate 1 with ammonium acetate in a polar solvent such a methanol or ethanol to give the methyl 2-amino cyclopent-1-ene-1-carboxylate 2. The amine 2 can be coupled with the appropriate acid in the presence of methanesulfonyl chloride (MsCl) and DMAP to give the desired amide 3. Finally, the ester can be saponified by one skilled in the art using such methods as NaOH or LiOH-dioxane to give compounds with the structure 4.

Scheme 2

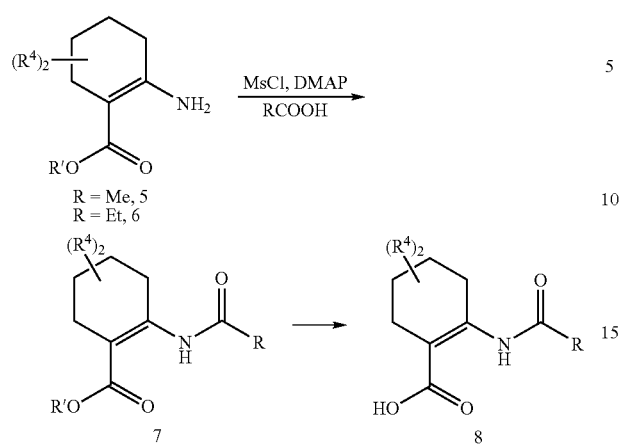

Compounds of Formula I, where X represents CH$_2$, a represents 2, and b represents 1 such that the sum of a and b is 3, can be prepared as illustrated in Scheme 2 by coupling commercially available methyl or ethyl 2-amino-cyclo-hex-1-ene-1-carboxylate 5 or 6 with the appropriate acid in the presence of methanesulfonyl chloride and DMAP to give the desired amide 7. The ester can be saponified to the desired compound 8 by methods known to those skilled in the art.

Scheme 3

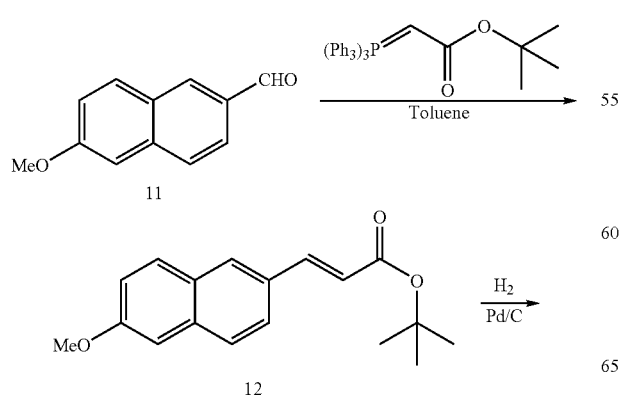

Shown in Scheme 3 is the preparation of acid of the structure 10 from commercially available material 9 by methods known to one skilled in the art, such as hydrogenation in a polar solvent, such as methanol or ethanol, using Pd/C as a catalyst.

Scheme 4

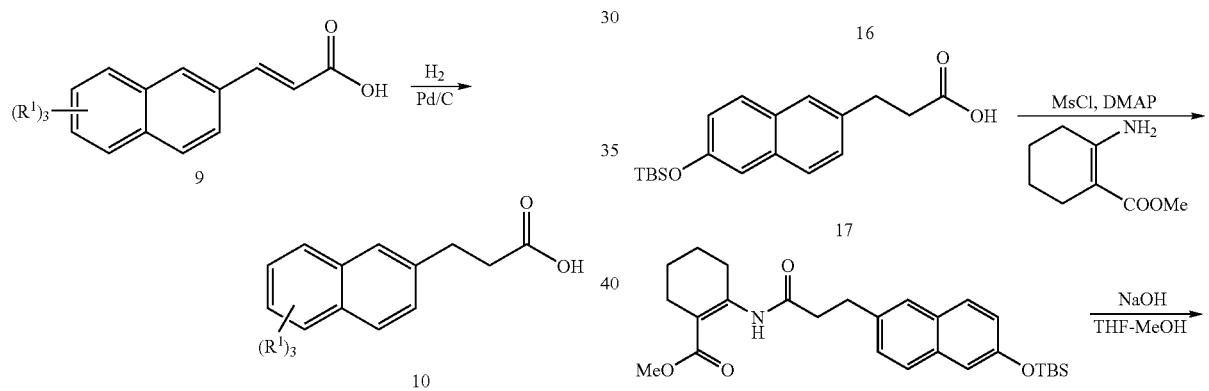

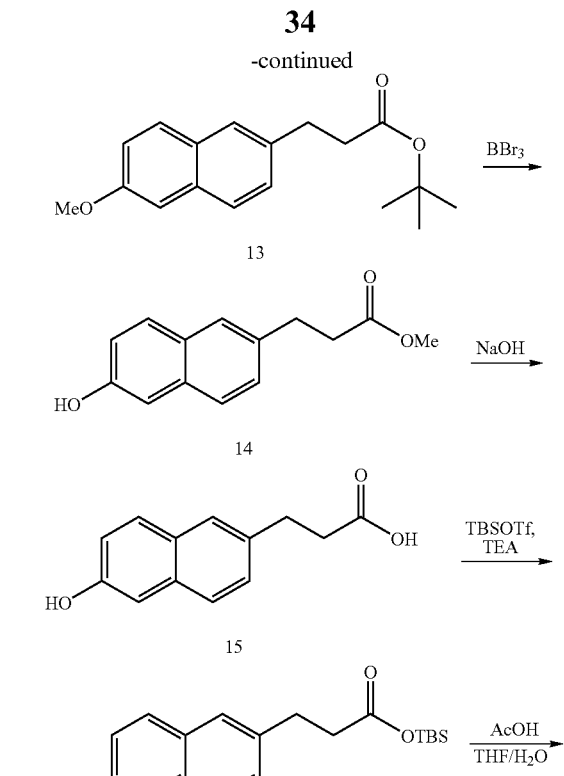

Compounds with the structure 19 can be prepared by the chemistry outlined in Scheme 4. Thus, 6-methoxy-2-naphthaldehyde 11 can be treated with a suitable ylide such as (tert-Butoxycarbonyl-methylene)triphenyl-phospharane in a non-polar solvent such as toluene or xylenes under refluxing conditions to give the desired olefin 12. Hydrogenation of the double bond can be accomplished using standard conditions such as H$_2$(g), Pd/C in a suitable polar solvent like methanol or ethanol to give 13. Removal of the methyl group in the methoxynaphthyl moiety can be accomplished with boron tribromide at low temperature, followed by a careful quenching of the reaction with methanol to give the trans-esterified product 14. Saponification of the ester was accomplished using conditions described earlier. The naphthol can be protected as the TBS ether using TBSOTf or TBS-Cl in the presence of a suitable base such as triethylamine or imidazole in dichloromethane. The TBS ester can be hydrolyzed with a mild acid such as acetic acid in THF-$H_2O$ to give the desired acid 17. This acid can be coupled to the methyl or ethyl 2-aminocyclo-hex-1-ene-1-carboxylate in the presence of methanesulfonyl chloride and DMAP to give the desired amide 18. Finally, TBS ether removal and methyl ester saponification can be achieved using NaOH/THF-$H_2O$ providing compounds of the structure 19.

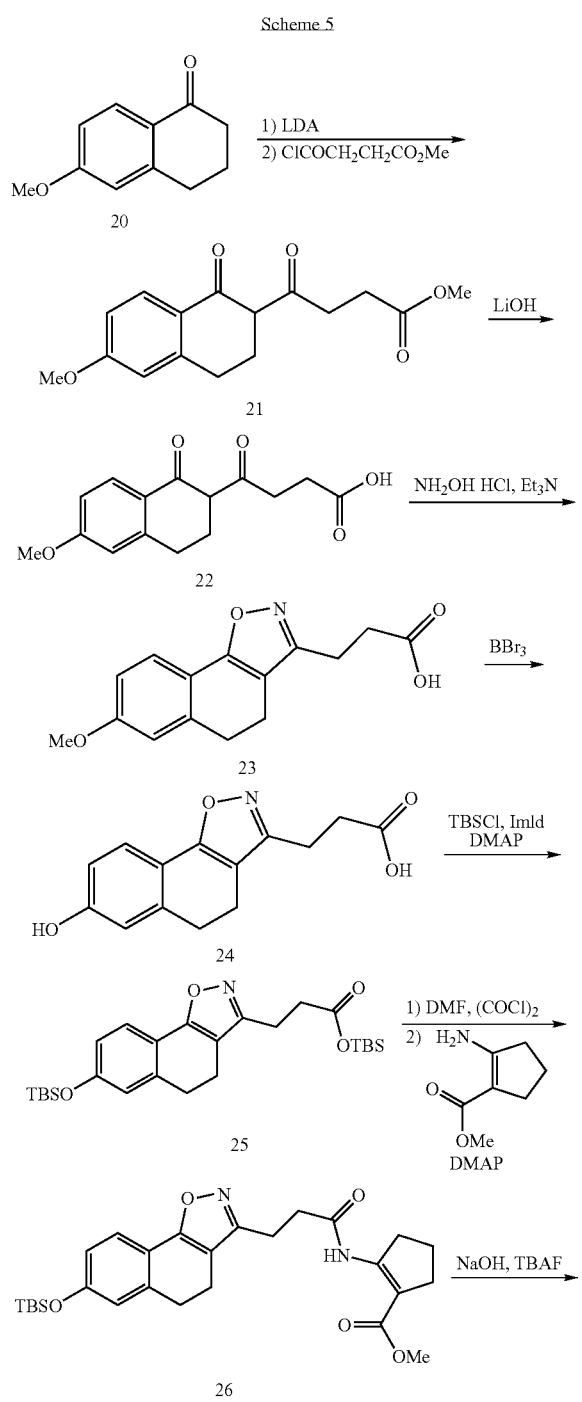

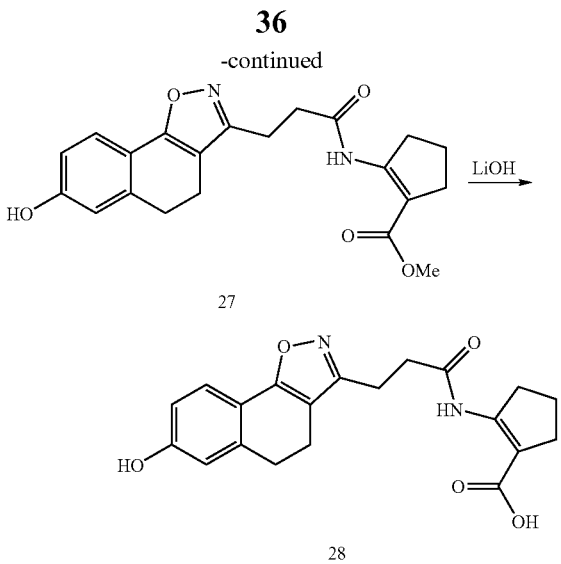

Compounds with the structure 28 can be prepared by the chemistry outlined in Scheme 5. Thus, treating a suitable tetralone such as 20 with LDA at low temperature followed by the addition of a suitable acylating agent such as 4-chloro-4-oxobutyrate provides the desired diketo-ester 21. The ester can be saponified using standard conditions known to one skilled in the art to give the acid 22. The di-ketone 22 can be converted to the fused isoxazole of the structure 23 by refluxing with hydroxylamine hydrochloride in the presence of a base such as triethylamine in an alcoholic solvent such as methanol or ethanol. De-protection of the methyl ether can be done with boron tribromide in a suitable solvent such as dichloromethane to give the desired alcohol 24. Treatment of the intermediate 24 with a silylating agent such as TBS-Cl in the presence of a base such as imidazole or triethylamine in a chlorinated solvent like DCM gives the bis-silyl protected ester 25. The silyl ester 25 can be treated with oxalyl chloride in a solvent such as DCM under anhydrous conditions followed by coupling with methyl 2-aminocyclo-pent-1-ene-1-carboxylate to give the desired amide 26. The TBS group can be removed using aqueous TBAF. Finally, the methyl ester can be saponified using standard conditions to give compounds of the structure 28.

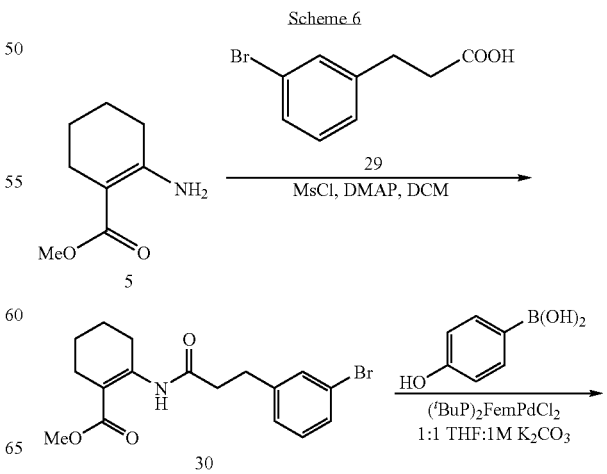

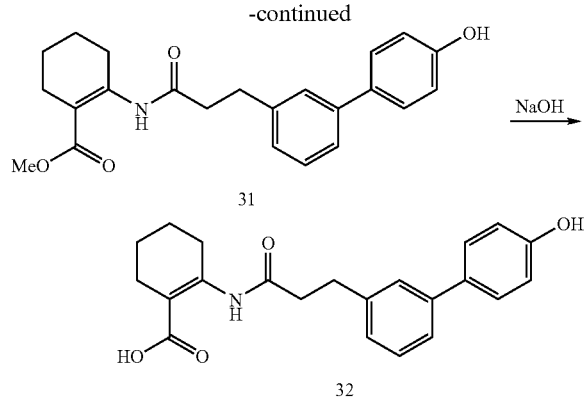

Scheme 6 outlines the strategy used to synthesize compounds of the structure 32. Coupling commercially available methyl or ethyl 2-aminocyclo-hex-1-ene-1-carboxylate 5 or 6 with 3-(3-bromophenyl) propionic acid 29 in the presence of methanesulfonyl chloride and DMAP gives the desired amide 30. The bromide 30 can be converted to 31 via a Suzuki reaction with a suitable boronic acid such as 4-hydroxy phenyl boronic acid in the presence of a catalyst such as Bis-tert-butyl-ferrocene palladium dichloride. The ester can be saponified by methods known to those skilled in the art providing compounds of the structure 32.

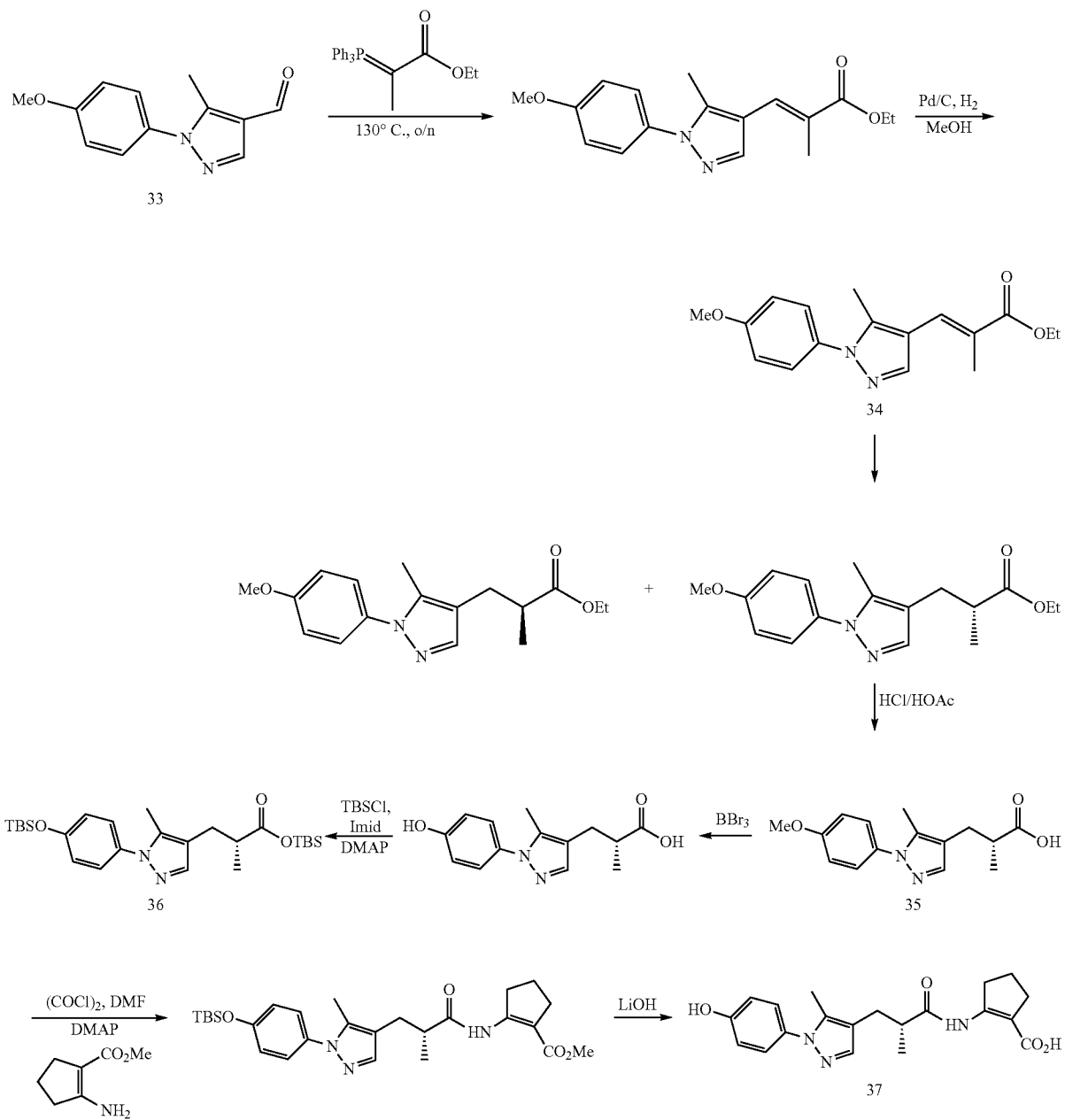

Scheme 7 outlines the strategy used to synthesize compounds of the structure 37. Homologating aldehyde 33, followed by reduction provides 34 which may be resolved into its enantiomers via chiral HPLC. One enantiomer is shown in Scheme 7 for illustrative purposes. Hydrolysis of the ethyl esters provides the acid 35, followed by demethylation and silylation to give 36. This intermediate can be acylated with the cyclopentene fragment, and saponified to provide biaryl products such as 37.

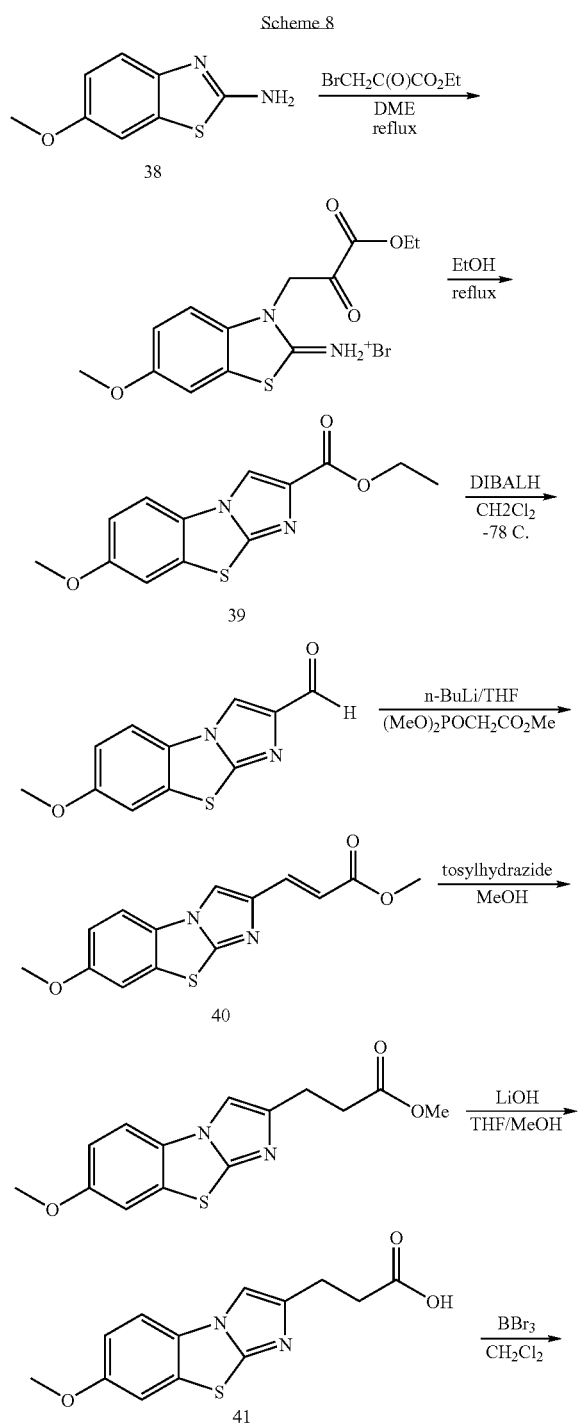

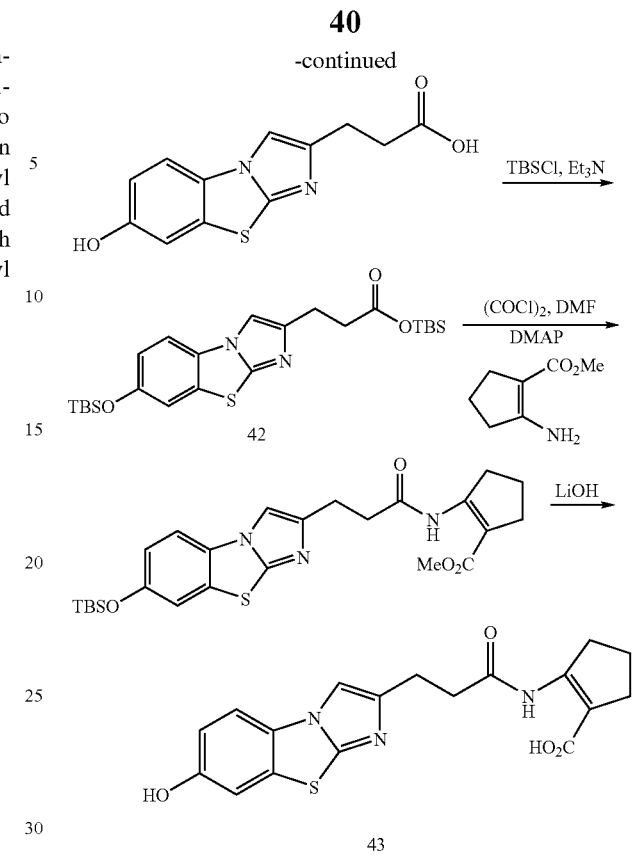

Scheme 8 outlines the strategy used to synthesize compounds of the structure 43. The aminobenzothiazole 38 may be N-alkylated and cyclized to form intermediate 39. The ester can be reduced to the aldehyde, and homologated to the enoate 40. This intermediate can then be reduced and saponified to provide the acid 41. Demethylation and silylation affords intermediate 42, which can be acylated and saponified once again as in Scheme 7 above, to provide products such as 43.

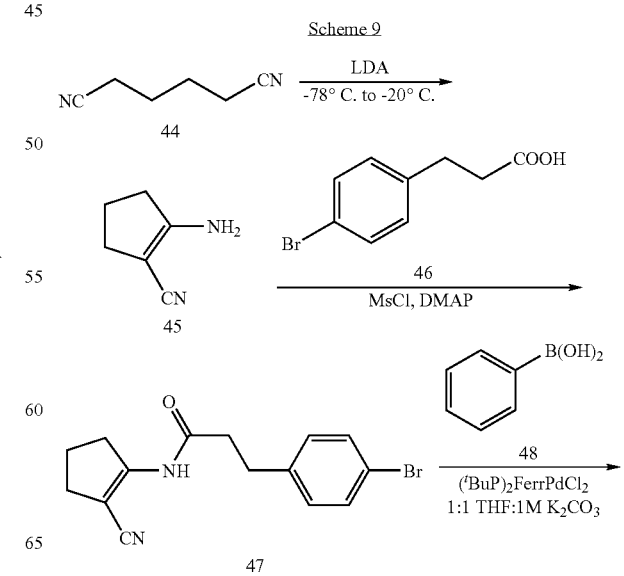

41

-continued

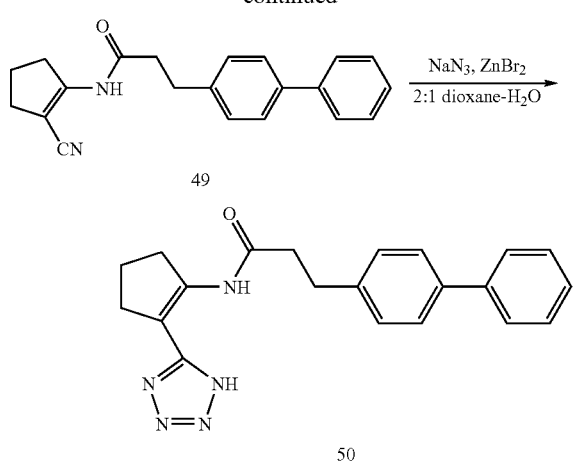

Scheme 9 outlines the strategy used to synthesize compounds of the structure 50. Adiponitrile can be converted to the amino-nitrile 45 via a Thorpe-Ziegler reaction using a suitable base such as LDA in a solvent such as THF. Coupling the amino nitrile 45 to 3-(4-bromophenyl) propionic acid 46 in the presence of methanesulfonyl chloride and DMAP gives the desired amide 47. The bromide 47 can be converted to 49 via a Suzuki reaction with a suitable boronic acid such as phenyl boronic acid in the presence of a catalyst such as 1,1 bis(di-tert-butylphosphino)-ferrocene palladium dichloride. Finally, treatment of the nitrile 49 with NaN$_3$ in the presence of a Lewis acid such as zinc bromide, in a suitable solvent mixture such as dioxane-water gives tetrazoles such as 50.

Scheme 10

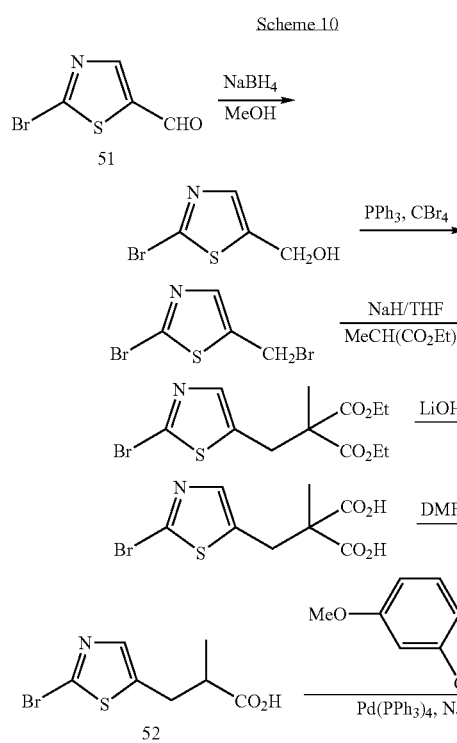

42

-continued

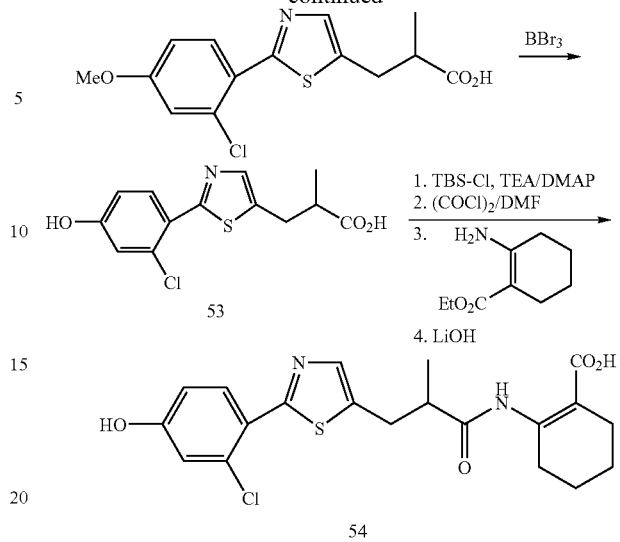

Scheme 10 outlines the strategy used to synthesize compounds of the structure 54. The heterocyclic bromo aldehyde 51 can be homologated to the intermediate 52 via several transformations including the displacement of an activated bromide with a malonate anion. The bromide 52 can be arylated and demethylated to provide acid 53, which in turn may be acylated and deprotected to provide compounds such as 54.

Scheme 11

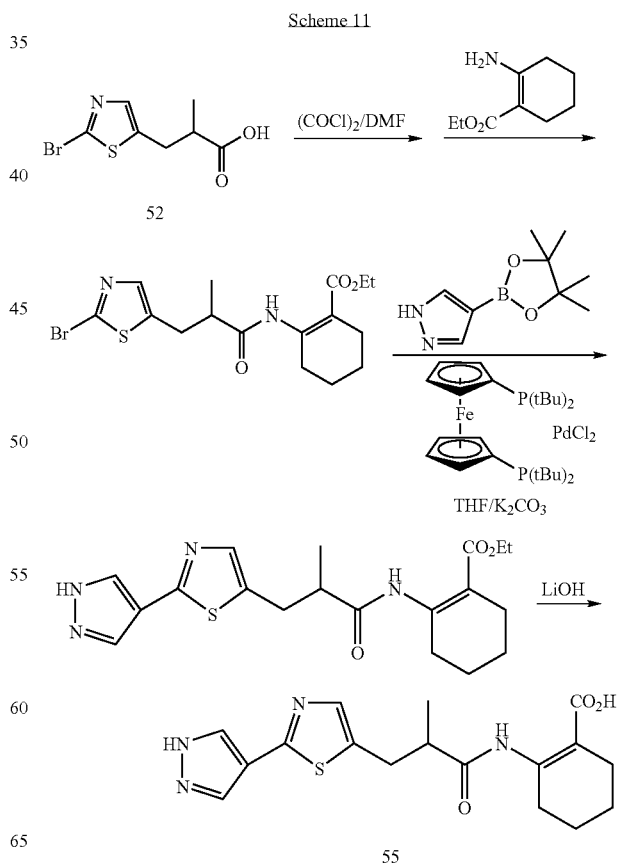

Scheme 11 displays a method for generating compounds of the structure 55. The acid intermediate 52 from Scheme 10 above may be acylated, the bromide coupled with a heterocyclic boronate ester, and this intermediate deprotected to provide compounds such as 55.

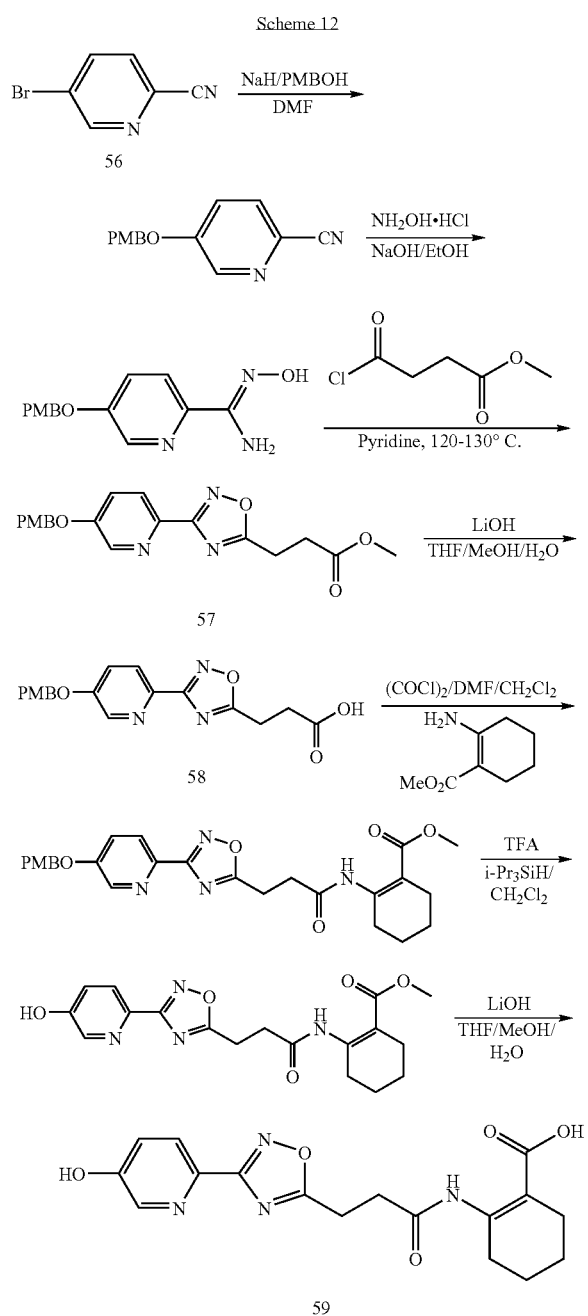

Scheme 12 demonstrates a synthetic strategy to access compounds of the structure 59. Starting from a pyridyl bromo nitrile such as 56, the bromide may be displaced, the nitrile transformed to an N-hydroxy amidine, this intermediate acylated and then cyclized to provide the intermediate 57. Saponification of 57 can give acid 58, which may be acylated, and after deprotection provide compounds such as 59.

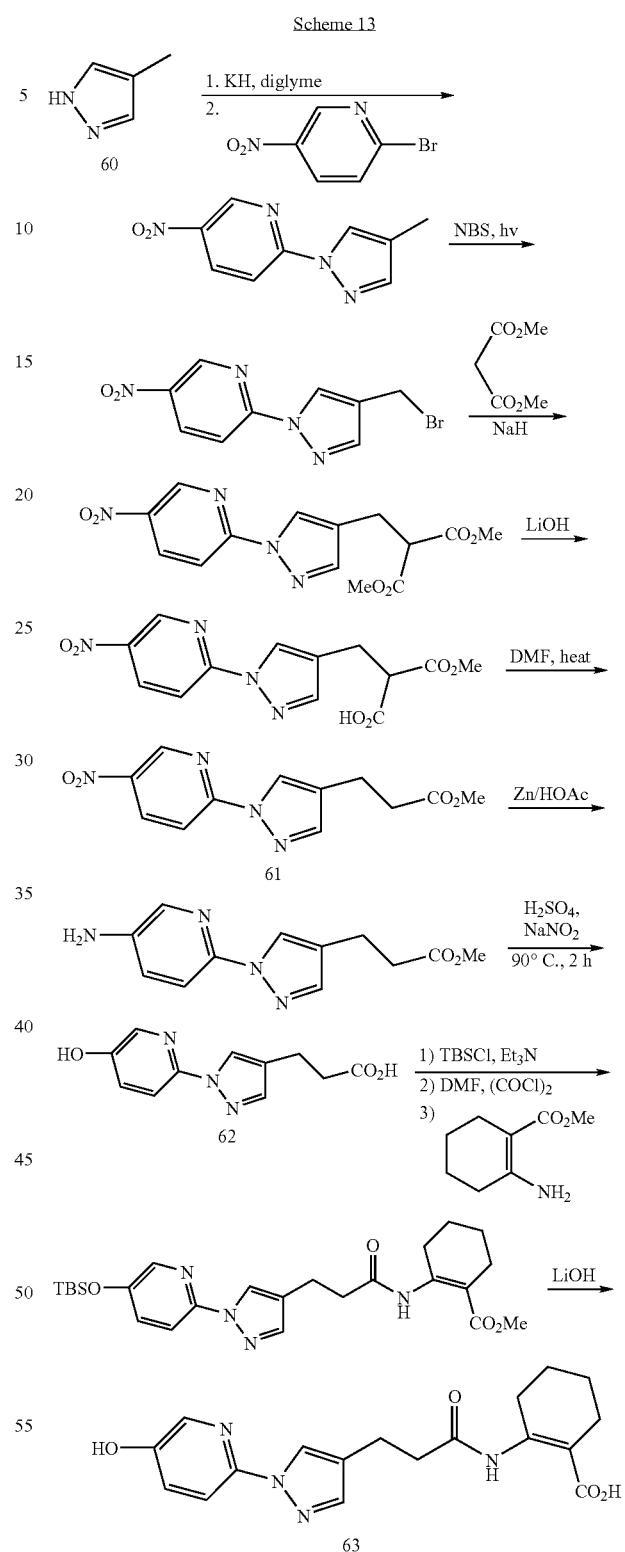

Scheme 13 outlines the strategy used to synthesize compounds of the structure 63. The pyrazole 60 may be N-arylated, this intermediate homologated to nitro 61, which in turn may be transformed to hydroxy acid 62. Upon acylation and deprotection, compounds such as 63 may be obtained.

45

Scheme 14

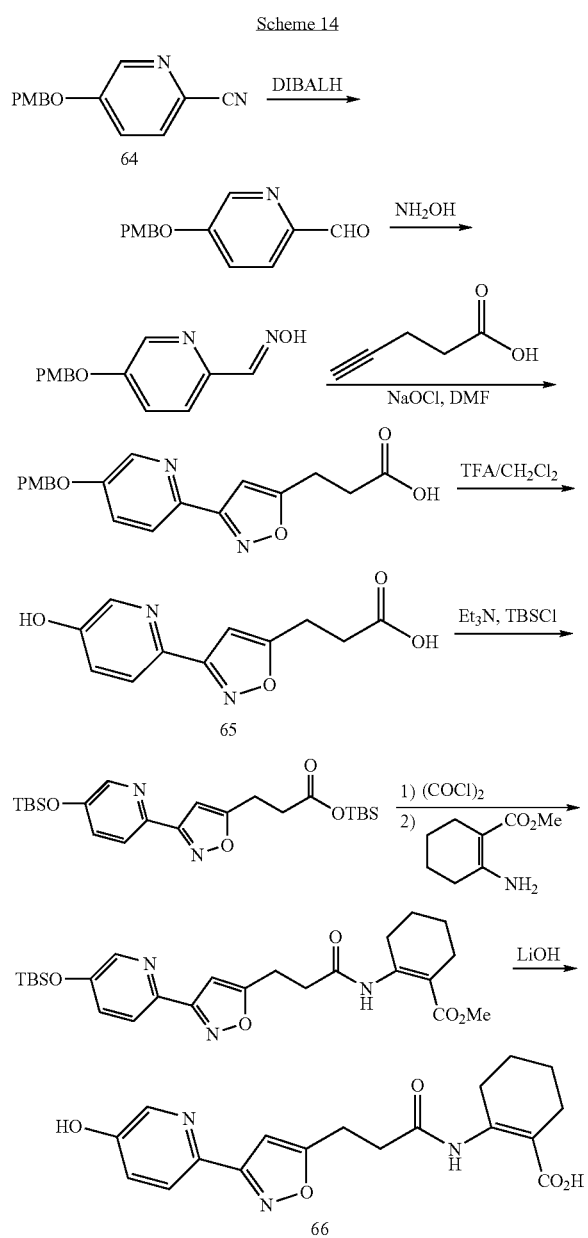

Scheme 14 displays a method to access compounds of the structure 66. The intermediate 64 generated in Scheme 12, may be elaborated into 65 via an intermediate oxime cycloaddition with an alkyne. The hydroxy acid 65 can be protected, acylated and deprotected to provide compounds such as 66.

Scheme 15

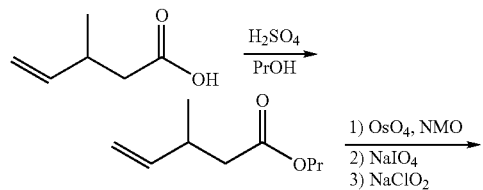

46

-continued

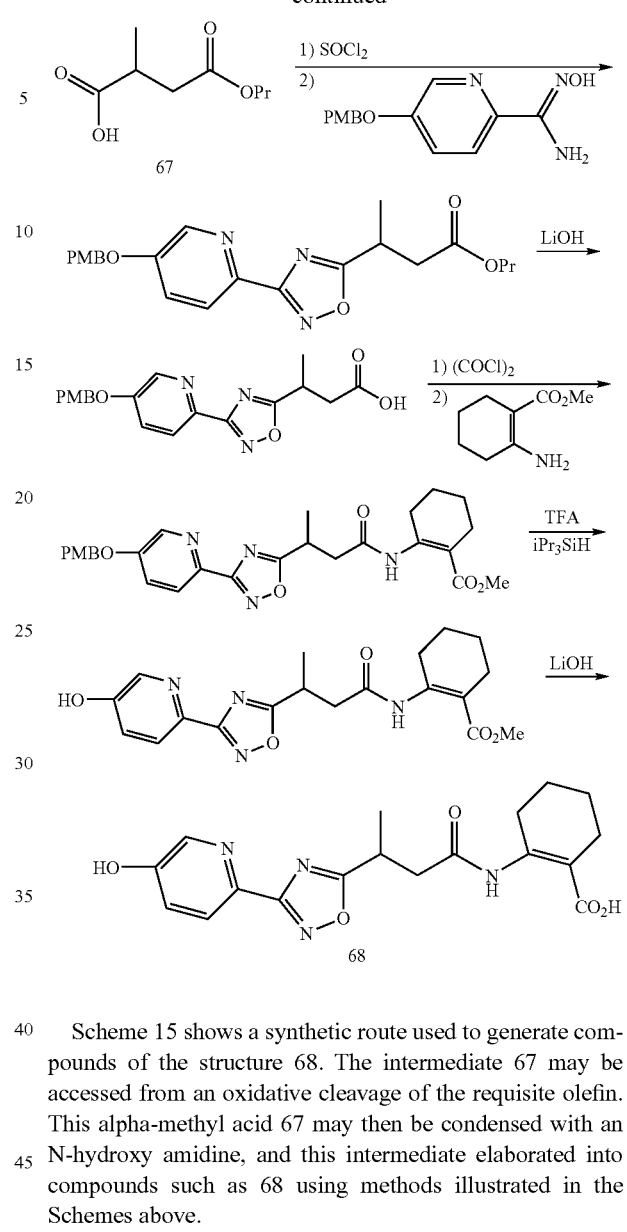

Scheme 15 shows a synthetic route used to generate compounds of the structure 68. The intermediate 67 may be accessed from an oxidative cleavage of the requisite olefin. This alpha-methyl acid 67 may then be condensed with an N-hydroxy amidine, and this intermediate elaborated into compounds such as 68 using methods illustrated in the Schemes above.

Scheme 16

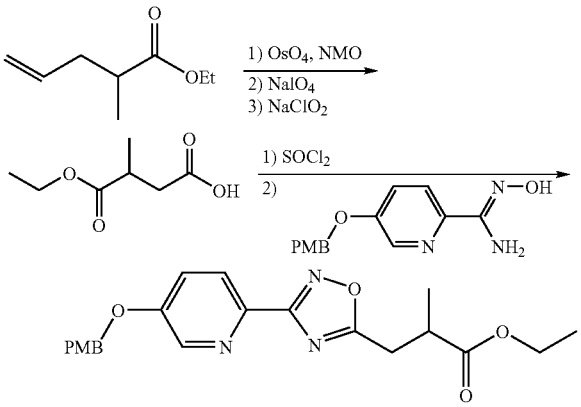

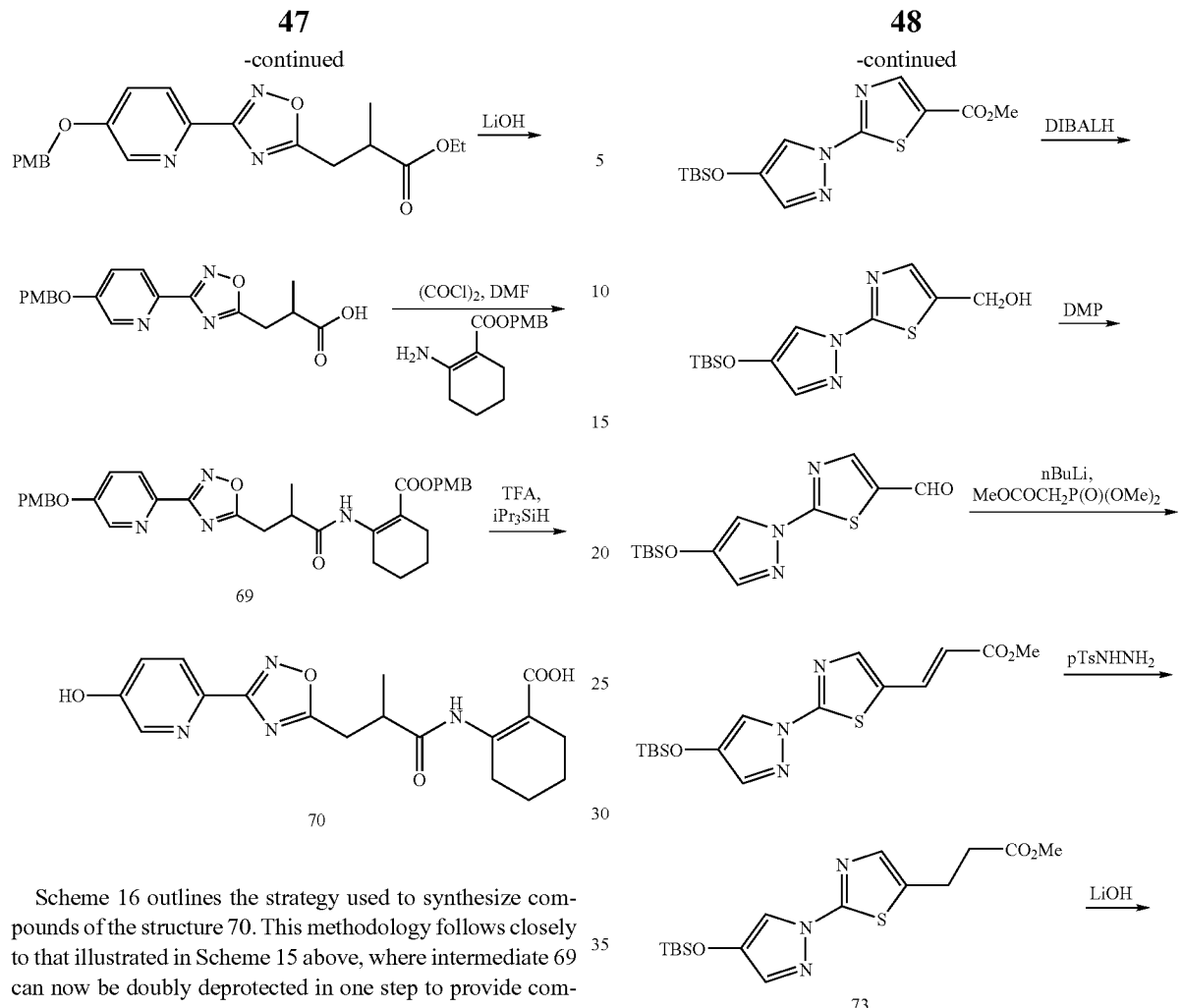

Scheme 16 outlines the strategy used to synthesize compounds of the structure 70. This methodology follows closely to that illustrated in Scheme 15 above, where intermediate 69 can now be doubly deprotected in one step to provide compounds such as 70, containing a methyl group alpha to the amide moiety.

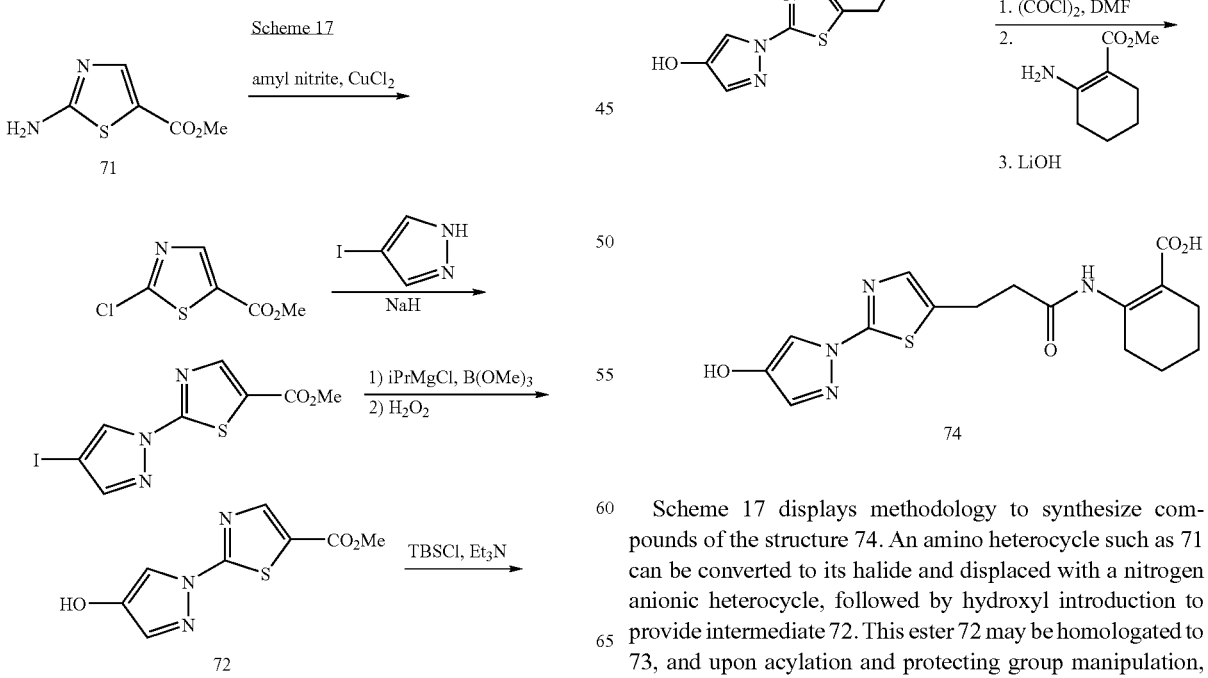

Scheme 17 displays methodology to synthesize compounds of the structure 74. An amino heterocycle such as 71 can be converted to its halide and displaced with a nitrogen anionic heterocycle, followed by hydroxyl introduction to provide intermediate 72. This ester 72 may be homologated to 73, and upon acylation and protecting group manipulation, converted to compounds such as 74.

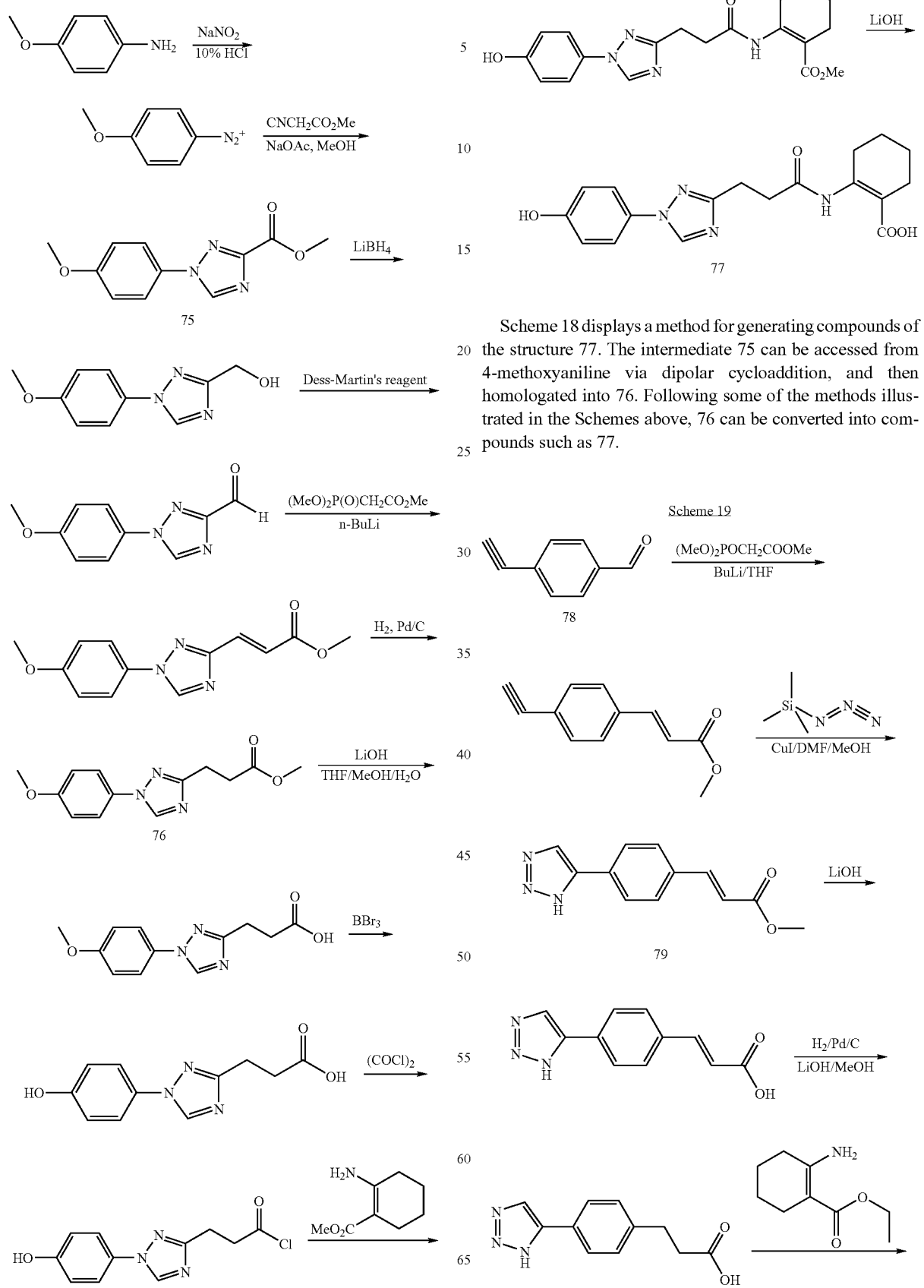
Scheme 18 displays a method for generating compounds of the structure 77. The intermediate 75 can be accessed from 4-methoxyaniline via dipolar cycloaddition, and then homologated into 76. Following some of the methods illustrated in the Schemes above, 76 can be converted into compounds such as 77.

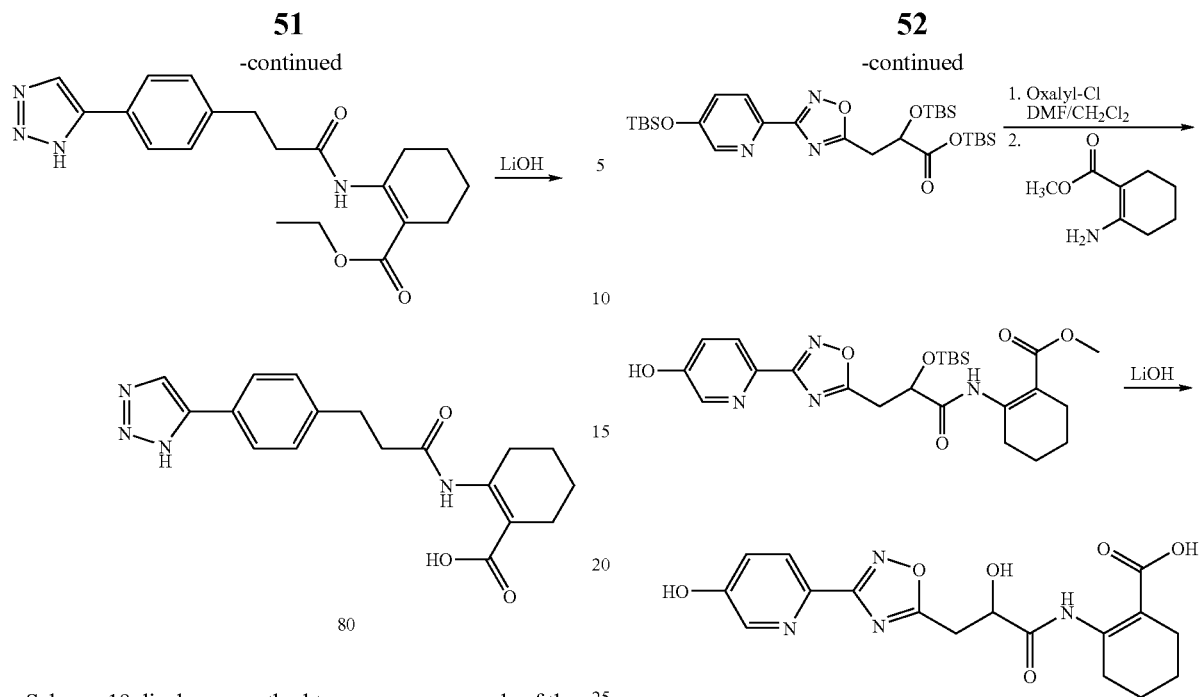

Scheme 19 displays a method to access compounds of the structure 80. Alkyne 78 may be homologated and undergo a cycloaddition reaction to generate intermediate 79. The enoate 79 may then be converted into compounds such as 80 using methods illustrated in the Schemes above.

Scheme 20 illustrates a strategy used to synthesize compounds of the structure 83. Malic acid 81 can be orthogonally protected, condensed with an N-hydroxy amidine, and deprotected to generate 82. The bis-hydroxyacid 82 may be globally silylated, and then acylated and deprotected to provide alpha-hydroxy compounds such as 83.

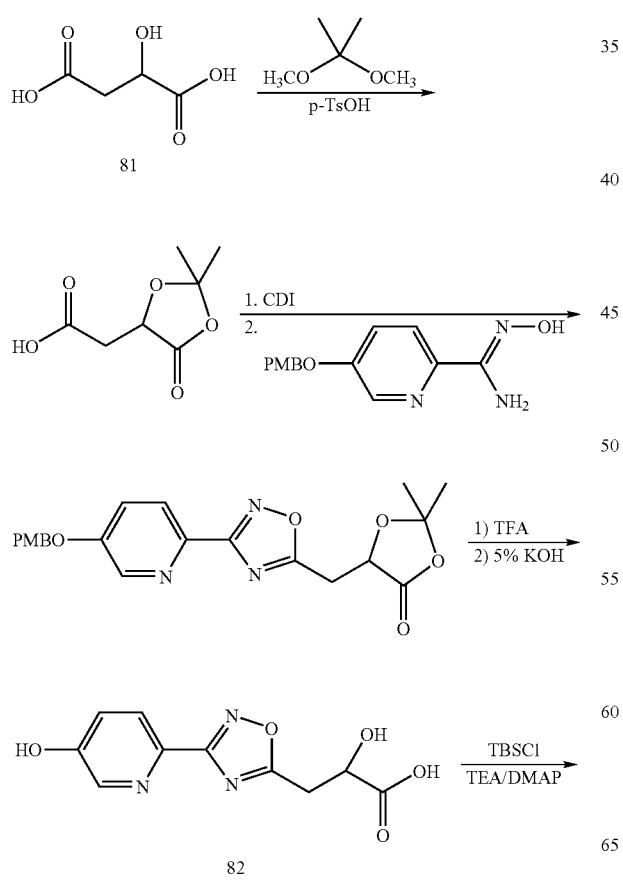

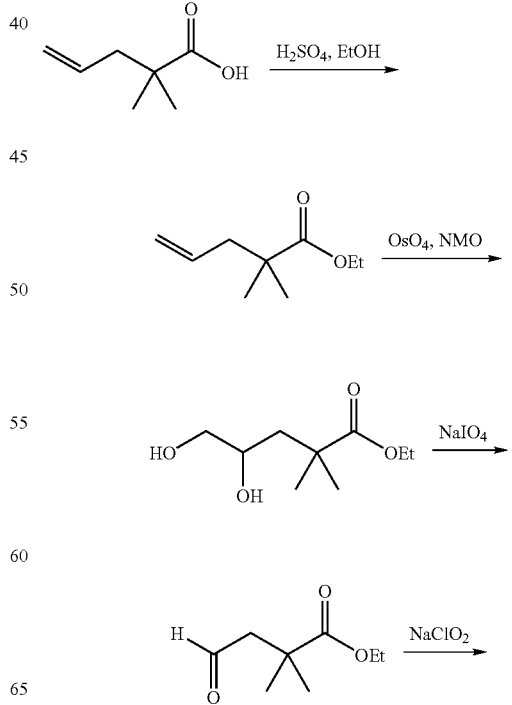

53

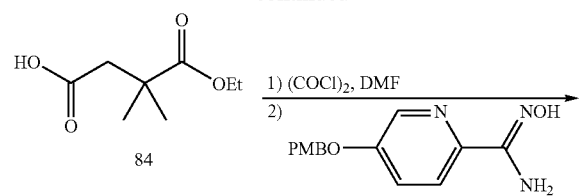

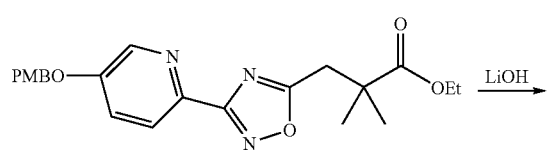

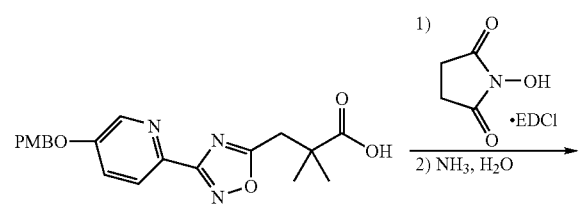

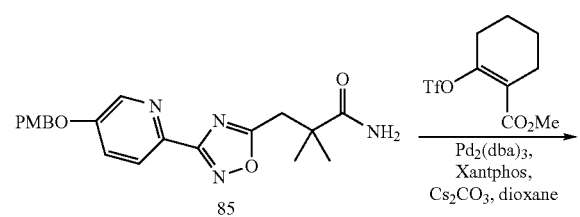

86

54

Scheme 22

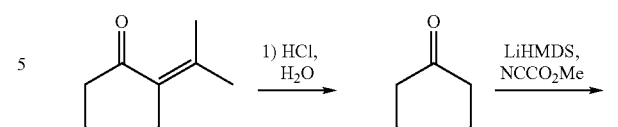

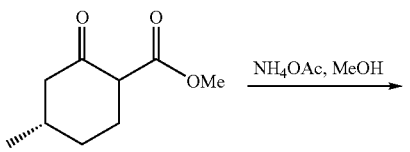

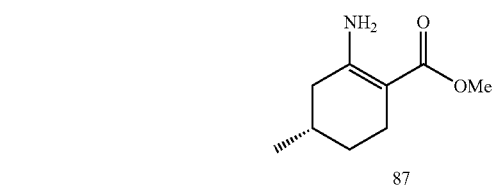

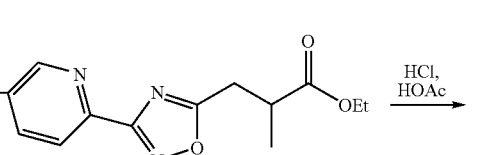

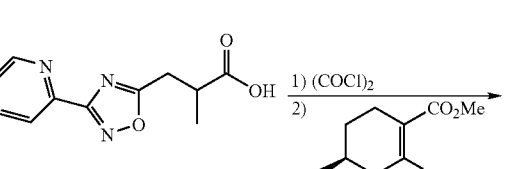

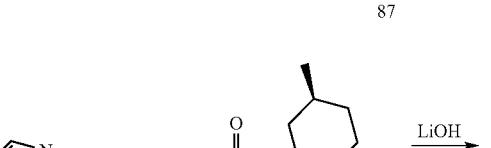

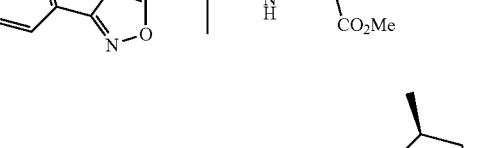

88

Scheme 21 displays a strategy used to generate compounds of the structure 86. Orthogonally protected acid ester intermediate 84 can be obtained via oxidative degradation of the requisite olefinic starting material. The acid 84 may then be condensed with an N-hydroxy amidine, and manipulated to provide a primary carboxamide 85. A primary carboxamide intermediate such as 85 may undergo a coupling reaction with an enol triflate, and upon further deprotection reactions, provide geminal dimethyl compounds such as 86.

Scheme 22 outlines a methodology to access compounds of the structure 88. Commercially available (S)-pulegone can be converted into intermediate 87 via reverse aldol, acylation with Mander's reagent, and enamine formation. Using a similar alpha-methyl ester intermediate illustrated in Scheme 16, chiral amine 87 may be elaborated into compounds such as 88.

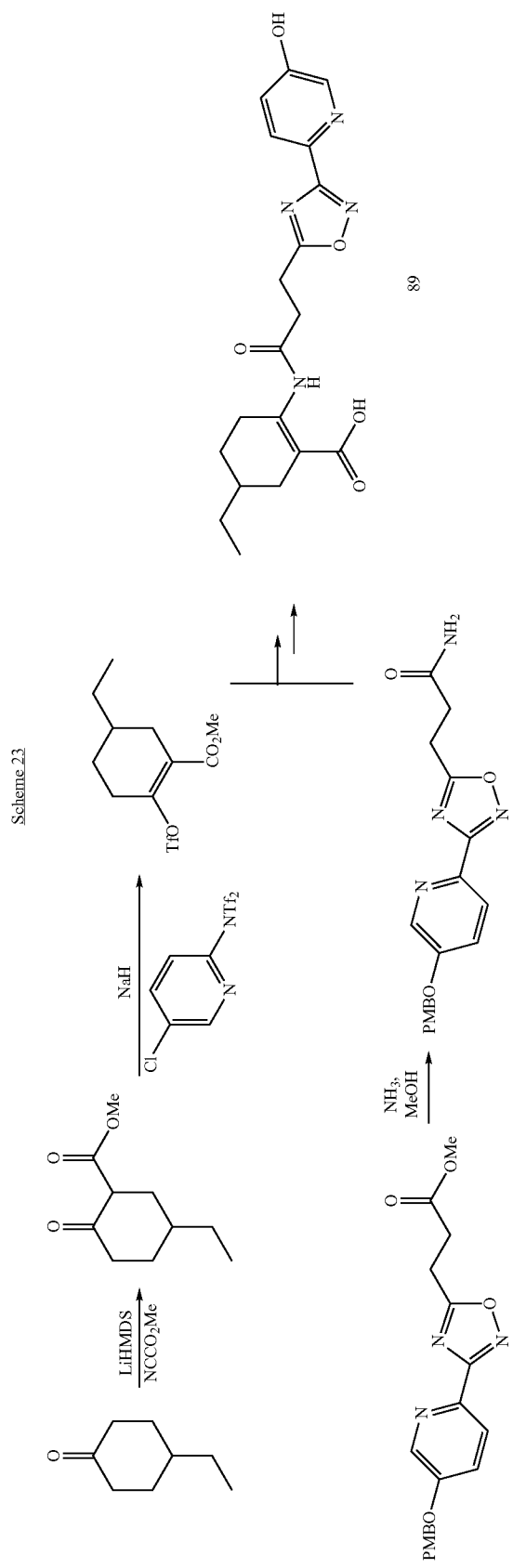

Scheme 23 displays a strategy to access compounds of the structure 89. Commercially available symmetrical ketones, such as 4-ethylcyclohexanone, can be acylated with Mander's reagent, followed by enol triflate formation with Comins' reagent. Using similar metal catalyzed coupling methodology illustrated in Scheme 21, different regioisomerically substituted cyclohexene compounds such as 89 may be accessed.

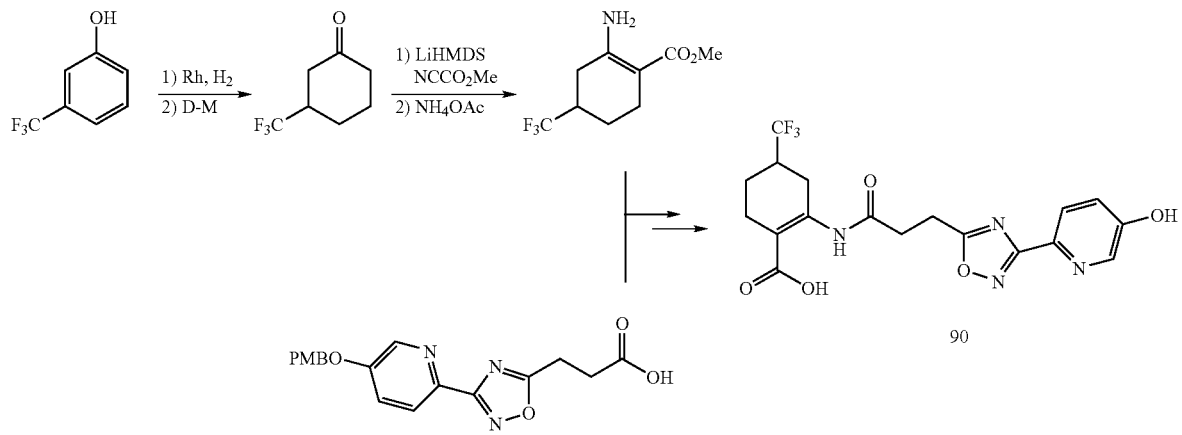

Scheme 24 illustrates a methodology to access compounds of the structure 90. Commercially available 3-(trifluoromethyl)phenol can be reduced to a hydroxy cyclohexane, oxidized with Dess-Martin reagent to the ketone, acylated with Mander's reagent, and followed by enamine formation. Using similar methodologies illustrated above, compounds such as 90 may be obtained that possess a trifluoromethyl substituted cyclohexene.

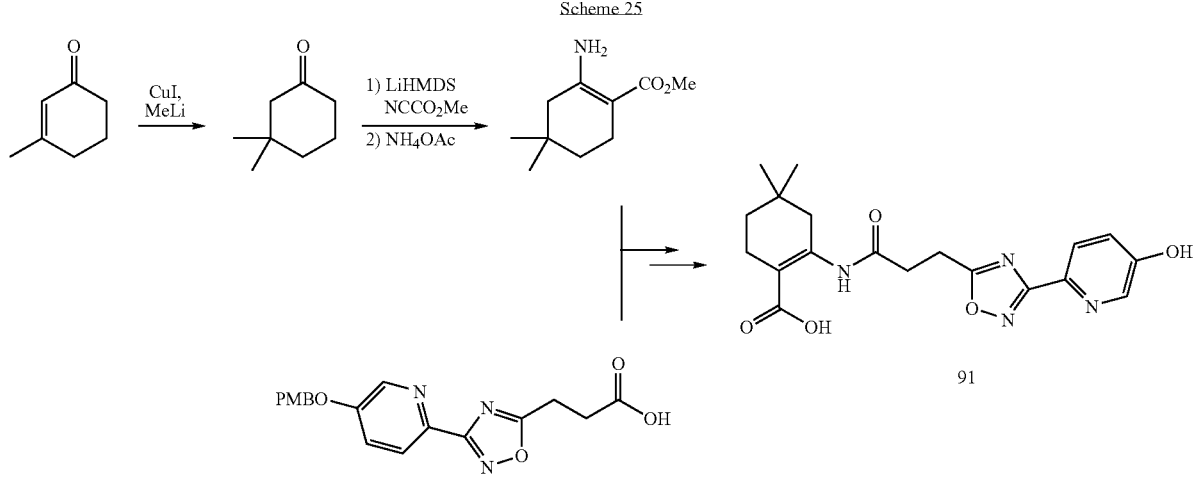

Scheme 25 displays a strategy to access compounds of the structure 91. Commercially available 3-methyl-2-cyclohexen-1-one can be substituted to generate a 3-geminal-dialkyl cyclohexanone. Upon acylation with Mander's reagent, enamine formation, and following similar methodologies illustrated above, compounds such as 91 may be obtained that possess a geminal dialkyl substituted cyclohexene.

Scheme 26
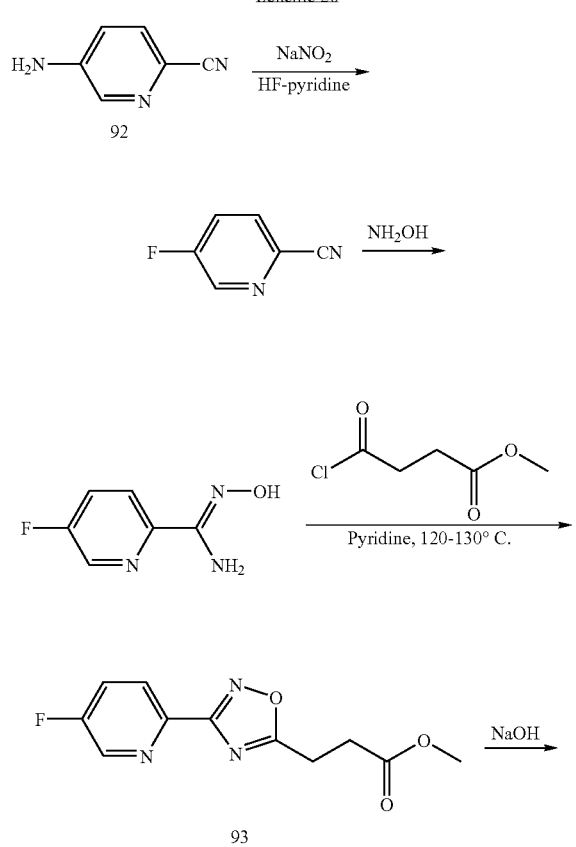
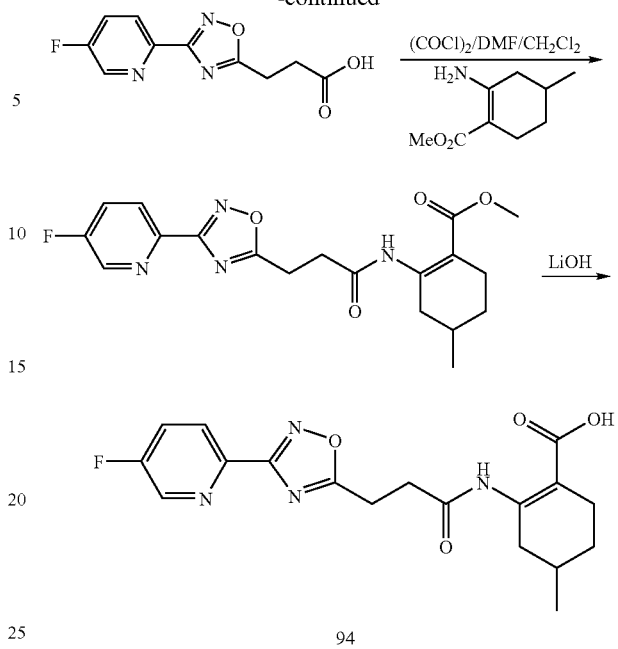
Scheme 26 shows a method to access compounds of the structure 94. Commercially available pyridine 92 can be fluorinated and incorporated into a fluoro biaryl intermediate such as 93. Subsequent hydrolysis, acylation, and saponification following similar methodologies illustrated above, may provide fluoropyridyl compounds such as 94.
Scheme 27
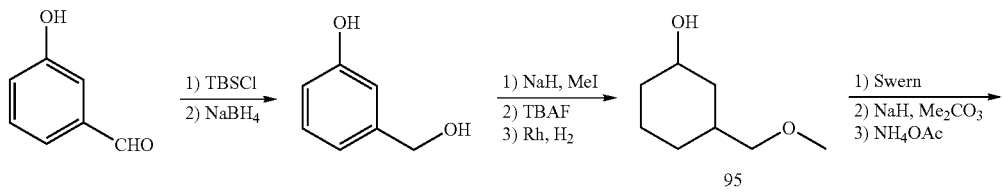
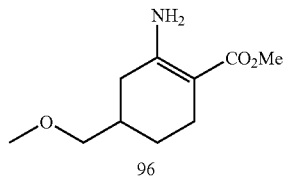
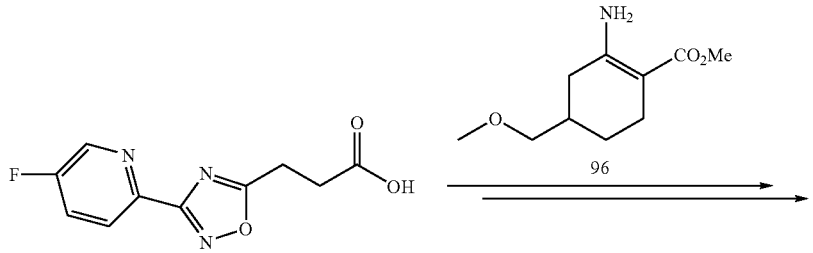

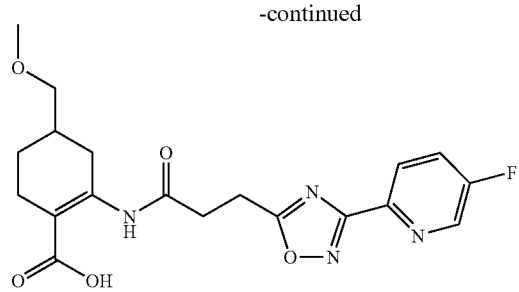

97

Scheme 27 illustrates a method to generate compounds of the structure 97. Commercially available 3-hydroxybenzaldehyde can be converted into the ether substituted cyclohexane intermediate 95 via the key reduction of the phenyl ring. Upon ketone formation and similar methodologies described above, the ether substituted cyclohexene aminoester 96 can be obtained. This enamine intermediate may be acylated and deprotected as described above, to generate compounds such as 97 that possess an ether substituted cyclohexene.

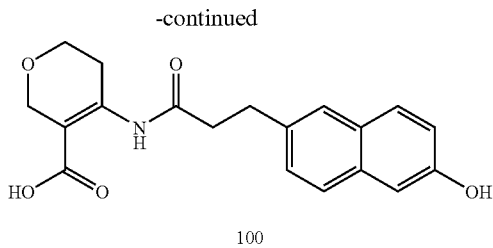

100

Scheme 28 displays methodology to access compounds of the structure 100. Commercially available tetrahydro-4-H-pyran-4-one can be converted into the dihydropyran triflate intermediate 98 via similar methodologies described above. In parallel, commercially available 6-methoxy-2-naphthaldehyde can be converted into the primary carboxamide intermediate 99, also via similar methodologies described above. Intermediates 98 and 99 may be coupled under similar metal catalyzed methodology illustrated in Scheme 21, to generate compounds such as 100 that possess a dihydropyran carboxylic acid moiety.

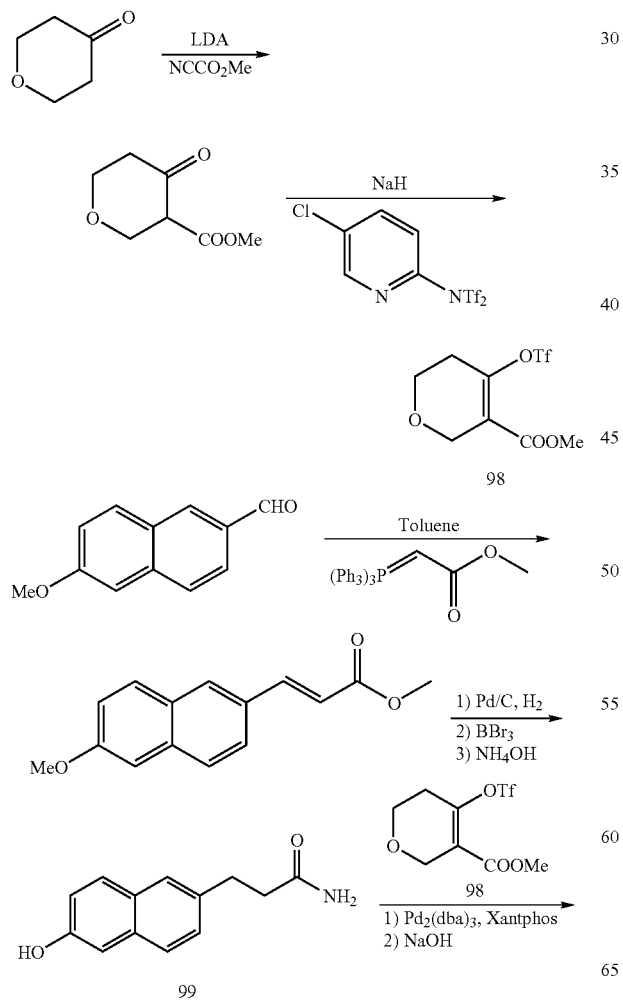

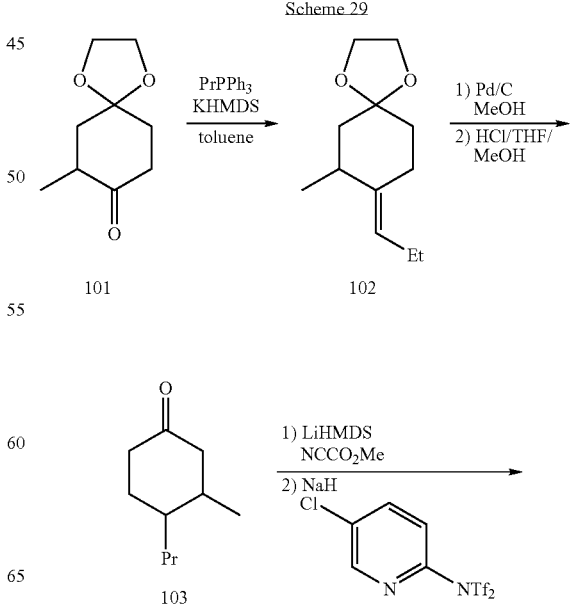

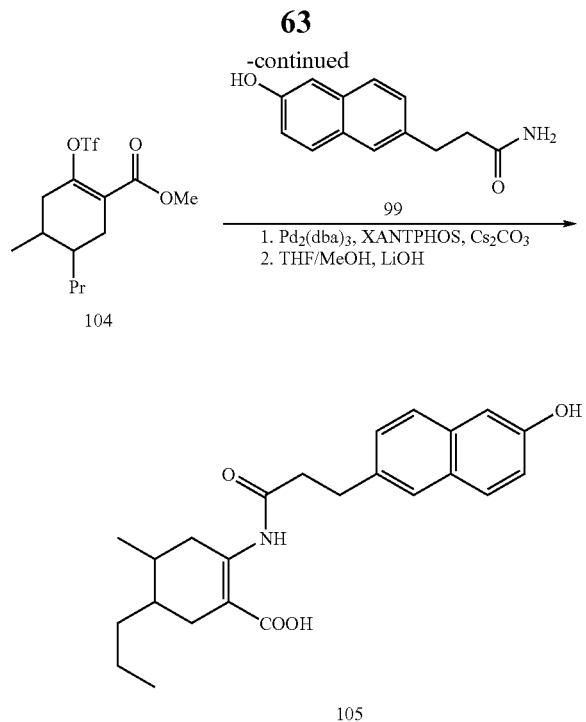

Scheme 29 illustrates a methodology to access compounds of the structure 105. The ketone 101 (for preparation see Danishefsky, et al *J. Am. Chem. Soc.* 2004, 126, 14358) can be converted to the olefin 102, followed by reduction of the double bond using standard hydrogenation conditions, and acid catalyzed removal of the ketal protecting group to provide the ketone 103. This material can be acylated using Mander's reagent to give the desired ketoester that is converted to the enol trifate 104 with Comins' reagent. Intermediates 104 and 99 may be coupled using similar metal catalyzed methodology illustrated in Scheme 21. Saponification of the methyl ester using standard conditions can generate vicinal disubstituted cyclohexene compounds such as 105.

The various organic group transformations and protecting groups utilized herein can be performed by a number of procedures other than those described above. References for other synthetic procedures that can be utilized for the preparation of intermediates or compounds disclosed herein can be found in, for example, M. B. Smith, J. March Advanced Organic Chemistry, 5$^{th}$ Edition, Wiley-Interscience (2001); R. C. Larock Comprehensive Organic Transformations, A Guide to Functional Group Preparations, 2$^{nd}$ Edition, VCH Publishers, Inc. (1999); T. L. Gilchrist Heterocyclic Chemistry, 3$^{rd}$ Edition, Addison Wesley Longman Ltd. (1997); J. A. Joule, K. Mills, G. F. Smith Heterocyclic Chemistry, 3$^{rd}$ Edition, Stanley Thornes Ltd. (1998); G. R. Newkome, W. W. Paudler Contempory Heterocyclic Chemistry, John Wiley and Sons (1982); or Wuts, P. G. M.; Greene, T. W.; Protective Groups in Organic Synthesis, 3$^{rd}$ Edition, John Wiley and Sons, (1999), all six incorporated herein by reference in their entirety.

REPRESENTATIVE EXAMPLES

The following examples are provided to more fully illustrate the present invention, and shall not be construed as limiting the scope in any manner. Unless stated otherwise:

(i) all operations were carried out at room or ambient temperature (RT), that is, at a temperature in the range 18-25° C.;

(ii) evaporation of solvent was carried out using a rotary evaporator under reduced pressure (4.5-30 mmHg) with a bath temperature of up to 50° C.;

(iii) the course of reactions was followed by thin layer chromatography (TLC) and/or tandem high performance liquid chromatography (HPLC) followed by mass spectroscopy (MS), herein termed LCMS, and any reaction times are given for illustration only;

(iv) yields, if given, are for illustration only;

(v) the structure of all final compounds was assured by at least one of the following techniques: MS or proton nuclear magnetic resonance (1H NMR) spectrometry, and the purity was assured by at least one of the following techniques: TLC or HPLC;

(vi) $^1$H NMR spectra were recorded on either a Varian Unity or a Varian Inova instrument at 500 or 600 MHz using the indicated solvent; when line-listed, NMR data is in the form of delta values for major diagnostic protons, given in parts per million (ppm) relative to residual solvent peaks (multiplicity and number of hydrogens); conventional abbreviations used for signal shape are: s. singlet; d. doublet (apparent); t. triplet (apparent); m. multiplet; br. broad; etc.;

(vii) MS data were recorded on a Waters Micromass unit, interfaced with a Hewlett-Packard (Agilent 1100) HPLC instrument, and operating on MassLynx/OpenLynx software; electrospray ionization was used with positive (ES+) or negative ion (ES−) detection; the method for LCMS ES+ was 1-2 mL/min, 10-95% B linear gradient over 5.5 min (B=0.05% TFA–acetonitrile, A=0.05% TFA–water), and the method for LCMS ES− was 1-2 mL/min, 10-95% B linear gradient over 5.5 min (B=0.1% formic acid–acetonitrile, A=0.1% formic acid–water), Waters XTerra C18—3.5 um–50×3.0 mmID and diode array detection;

(viii) automated purification of compounds by preparative reverse phase HPLC was performed on a Gilson system using a YMC-Pack Pro C18 column (150×20 mm i.d.) eluting at 20 mL/min with 0-50% acetonitrile in water (0.1% TFA);

(ix) the manual purification of compounds by preparative reverse phase HPLC (RPHPLC) was conducted on either a Waters Symmetry Prep C18—5 um–30×100 mmID, or a Waters Atlantis Prep dC18—5 um–20×100 mmID; 20 mL/min, 10-100% B linear gradient over 15 min (B=0.05% TFA–acetonitrile, A=0.05% TFA–water), and diode array detection;

(x) the purification of compounds by preparative thin layer chromatography (PTLC) was conducted on 20×20 cm glass prep plates coated with silica gel, commercially available from Analtech;

(xi) flash column chromatography was carried out on a glass silica gel column using Kieselgel 60, 0.063-0.200 mm ($SiO_2$), or a Biotage $SiO_2$ cartridge system including the Biotage Horizon and Biotage SP-1 systems;

(xii) chemical symbols have their usual meanings, and the following abbreviations have also been used: h (hours), min. (minutes), v (volume), w (weight), b.p. (boiling point), m.p. (melting point), L (liter(s)), mL (milliliters), g (gram(s)), mg (milligrams(s)), mol (moles), mmol (millimoles), eq or equiv (equivalent(s)), IC50 (molar concentration which results in 50% of maximum possible inhibition), EC50 (molar concentration which results in 50% of maximum possible efficacy), uM (micromolar), nM (nanomolar);

(xiii) definitions of acronyms are as follows:

| | |
|---|---|
| BBr₃ is boron tribromide | B(OMe)₃ is trimethyl borate |
| Comins' reagent is 2-[N,N-Bis(trifluromethylsulfonyl)amino]-5-chloropyridine | CDI is 1,1'-carbonyl diimidazole |
| DCM is dichloromethane (methylene chloride) | DIBALH is diisobutyl aluminum hydride |
| DMF is dimethylformamide | DMAP is 4-dimethyl amino pyridine |
| DMSO is dimethyl sulfoxide | iPrMgCl is isopropyl magenisium chloride |
| KHMDS is potassium bis(trimethylsilyl) amide | LDA is lithium diisopropyl amide |
| LiHMDS is lithium bis(trimethylsilyl) amide | Mander's reagent is methyl cyanoformate |
| NBS is N-bromo-succinimide | |
| NaOCl is sodium hypochlorite | NMO is 4-methylmorpholine N-oxide |
| OTf is triflate | Pd(PPh₃)₄ is tetrakis triphenylphosphine palladium (0) |
| Pd₂(dba)₃ is Tris(dibenzylideneacetone) dipalladium (0); | TBAF is tetrabutylammonium fluoride; |
| TBS Chloride is t-bulyl dimethyl silyl chloride | TBSOTF is t-butyl dimethyl silyl trifluoromethane sulfonate |
| TFA is trifluoroacetic acid | THF is tetrahydrofuran |
| XANTPHOS is 9,9-Dimethyl-4,5-bis(diphenyl-phosphino)xanthene | |

Example 1

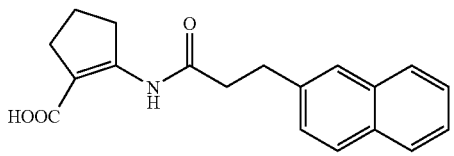

To a solution of methyl-2-oxocyclopentane-1-carboxylate (1.5 g, 10.55 mmol) in methanol was added ammonium acetate (4.07 g, 52.76 mmol). After stirring the reaction at room temperature for 18 h, it was concentrated in vacuo. The residue was dissolved in DCM, washed with water, brine, dried over anhydrous $Na_2SO_4$, filtered and concentrated in vacuo. This cyclopentene aminoester intermediate was used without any further purification.

To a solution of 3-(2-naphthyl)acrylic acid (1.5 g, 7.56 mmol) in 1:1 ethanol-ethyl acetate (50 mL) was added Pd/C and the resulting mixture stirred under a $H_2$ balloon for 18 h. The reaction mixture was filtered through celite, and concentrated in vacuo to give the desired saturated naphthyl acid as a white solid.

To a solution of this saturated naphthyl acid intermediate (150 mg, 0.75 mmol) in DCM (6 mL) cooled to 0° C. was added DMAP (201 mg, 1.65 mmol) followed by methanesulfonyl chloride (0.059 mL, 0.75 mmol). After 5 min, the cyclopentene aminoester intermediate (95 mg, 0.67 mmol) was added as a solid. The mixture was stirred at RT for 18 h, and quenched with saturated $NH_4Cl$ solution. The resulting mixture was extracted with DCM. The organic layer was dried over anhydrous $Na_2SO_4$ filtered and concentrated in vacuo. The residue was purified by flash chromatography using 10% ethyl acetate-hexanes as the eluant to give the desired amide product as a methyl ester.

To a solution of this ester intermediate (15 mg, 0.046 mmol) in THF (2 mL), was added methanol (1 mL) followed by 1 N NaOH (1 mL). The resulting reaction mixture was stirred at 23° C. for 6 h. It was neutralized to pH=7 by the addition of 1N HCl and extracted with ethyl acetate. The organic layer was dried over anhydrous $Na_2SO_4$, filtered and concentrated in vacuo. The residue was purified by reverse phase HPLC (Gilson) to provide Example 1. ¹H NMR (500 MHz, $CD_3OD$) δ 1.85 (m, 2H), 2.49 (m, 2H), 2.8 (t, 2H), 3.1 (m, 4H), 7.4 (m, 3H), 7.7 (bs, 1H), 7.8 (m, 3H); LCMS m/z 308 (M−1).

Preparation of Cyclohexene Aminoester and Enol Triflate Ester Intermediates

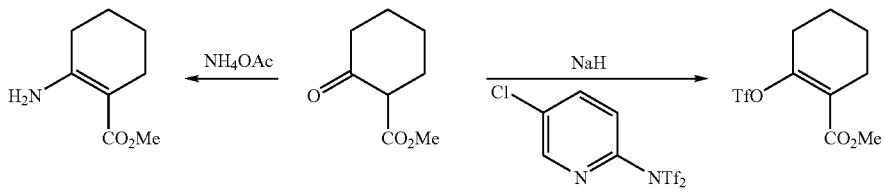

To a slurry of NaH (5.6 g, 60%) in 200 mL of THF was slowly added methyl cyclohexanone 2-carboxylate (19.9 g, 90%) at 0° C. After 30 min, the mixture was warmed to 23° C. and stirred for 15 min. The resulting mixture was cooled to 0° C., and to it was added Commin's reagent (50 g) in portions. The resulting mixture was warmed to RT and stirred for 2.5 h. The solution was then concentrated, and the residue was partitioned between ethyl acetate and water. The organic layer was dried with sodium sulfate and concentrated. The residue was purified by Biotage (5-10% ethyl acetate in hexane) to give the cyclohexene enol triflate ester.

To a solution of methyl cyclohexanone 2-carboxylate (10.3 g, 90%) in 100 mL of methanol was added ammonium acetate (8.5 g). The resulting mixture was stirred at room temperature overnight. The mixture was then concentrated, and the residue was dissolved in ethyl acetate. The solid was filtered, and the filtrate was washed with water, brine and dried over sodium sulfate. The resulting solution was concentrated to give the cyclohexene aminoester as an oil, which crystallized from hexane as a white solid.

Example 2

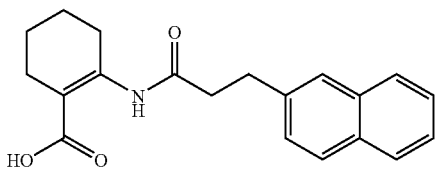

To a solution of the saturated naphthyl acid intermediate from Example 1 (194 mg, 0.97 mmol) in DCM (6 mL), was added DMAP (236 mg, 1.93 mmol) followed by methanesulfonyl chloride (0.05 mL, 0.64 mmol). After 5 min, a solution of methyl 2-aminocyclohex-1-ene-1-carboxylate (100 mg, 0.64 mmol) in DCM (1 mL) was added. The reaction mixture was stirred at RT for 18 h, and quenched with saturated NH$_4$Cl solution. The resulting mixture was extracted with DCM dried over anhydrous Na$_2$SO$_4$, filtered and concentrated in vacuo. The residue was purified by flash chromatography using 7% ethyl acetate-hexanes to provide the amide as a methyl ester.

To a solution of this ester intermediate in THF (2 mL) was added MeOH (1 mL) and 1N NaOH (1 mL). The resulting reaction mixture was stirred at room temperature for 18 h, then neutralized to pH=7 by the addition of 1N HCl, and extracted with ethyl acetate. The organic layer was dried over anhydrous Na$_2$SO$_4$, filtered, concentrated in vacuo and purified by reverse phase HPLC (Gilson) to provide Example 2. $^1$H NMR (500 MHz, CD$_3$OD) δ 1.55 (m, 4H), 2.3 (m, 2H), 2.7 (t, 2H), 2.85 (m, 2H), 3.1 (t, 2H), 7.45 (m, 3H), 7.66 (s, 1H), 7.77 (m, 3H); LCMS m/z 324 (M+1).

Example 3

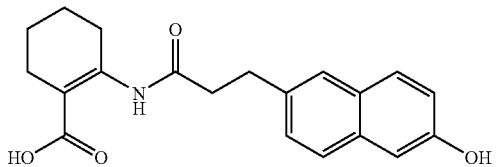

To a solution of 6-methoxy-2-naphthaldehyde (3.6 g, 19.38 mmol) in toluene (100 mL) placed in a pressure vessel, was added (tert-butoxycarbonyl-methylene)triphenyl-phospharane (8.76 g, 23.25 mmol). The resulting mixture was refluxed at 120° C. for 18 h. The reaction mixture was concentrated in vacuo and purified using a Biotage flash 40M column with 15% ethyl acetate-hexanes as the eluant to give the enoate intermediate.

To a solution of this tert-butyl-3-(6-methoxy-2-naphthyl) acrylate (4.88 g, 17.16 mmol) in ethanol (100 mL) was added Pd/C. The resulting mixture was stirred under a H$_2$ balloon for 18 h. The reaction mixture was filtered through celite and concentrated in vacuo to give the saturated ester as a white solid.

To a solution of this ether ester intermediate (150 mg, 0.52 mmol) in DCM cooled to 0° C., was added BBr$_3$ (5.23 mL, 1.0M in DCM). After 30 min, the reaction mixture was quenched by the addition of methanol (2 mL). The reaction mixture was concentrated in vacuo, and the residue was dissolved in ethyl acetate and washed with water. The organic layer was dried over anhydrous Na$_2$SO$_4$, filtered and concentrated in vacuo. The residue was purified by flash chromatography using 20% ethyl acetate-hexanes as eluant. This transesterified methyl ester (97 mg, 0.42 mmol) was dissolved in THF (3 mL) and MeOH was added (2 mL) followed by 1N NaOH (2 mL). After stirring for 6 h, the mixture was neutralized to pH=7 by the addition of 1N HCl. The resulting solution was extracted with ethyl acetate, dried over anhydrous Na$_2$SO$_4$, filtered and concentrated in vacuo. This naphtholic acid was used in the next step without any further purification.

To a solution of this naphtholic acid (106 mg, 0.49 mmol) in DCM (5 mL) cooled to 0° C., was added TBSOTf (0.17 mL, 0.73 mmol) followed by triethylamine (0.14 mL, 0.98 mmol). After warming the mixture to 23° C. and stirring for 2 h, it was quenched by the addition of water. The resulting mixture was extracted with DCM, dried over anhydrous Na$_2$SO$_4$, filtered and concentrated in vacuo. This bis-silylated material was dissolved in 1:1 THF/H$_2$O (2 mL) and AcOH (3 mL) was added. After stirring the mixture at RT for 1 h, it was diluted with water and extracted with ethyl acetate. The organic layer was dried over anhydrous Na$_2$SO$_4$, filtered and concentrated in vacuo to give the desired acid intermediate.

To a solution of this acid (51 mg, 0.154 mmol) in DCM (2 mL), was added DMAP (48 mg, 0.39 mmol) followed by methanesulfonyl chloride (0.012 mL, 0.154 mmol). After 5 min, methyl 2-aminocyclohex-1-ene-1-carboxylate (20 mg, 0.128 mmol) was added as a solid. The reaction mixture was heated to 50° C. for 18 h, and then cooled to RT and quenched by the addition of saturated ammonium chloride. The resulting mixture was extracted with DCM, dried over anhydrous Na$_2$SO$_4$ filtered and concentrated in vacuo. The residue was purified by flash chromatography using 10% ethyl acetate-hexanes as the eluant to provide the amide product.

To a solution of this intermediate ester (109 mg, 0.23 mmol) in THF (3 mL), was added 1N NaOH (1 mL) followed by MeOH (1.5 mL). After the reaction was complete, it was neutralized to pH=7 by the addition of 1N HCl. The resulting mixture was extracted with ethyl acetate, dried over anhydrous Na$_2$SO$_4$, filtered and concentrated in vacuo. The residue was purified by reverse phase HPLC (Gilson) to provide Example 3. $^1$H NMR (500 MHz, DMSO-d$_6$) δ 1.5 (m, 4H), 2.2 (bt, 2H), 2.63 (t, 2H), 2.8 (bt, 2H), 2.92 (t, 2H), 7.1 (m, 2H), 7.27 (d, 1H), 7.52 (m, 2H), 7.65 (d, 1H), 9.6 (bs, 1H), 11.6 (bs, 1H), 12.5 (bs, 1H); LCMS m/z 338 (M−1).

Example 4

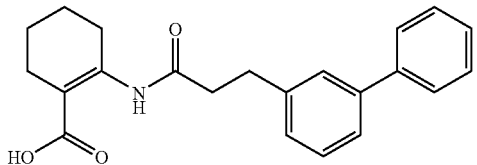

To a solution of methyl 3-(3-bromophenyl)propionate (100 mg, 0.411 mmol) in toluene (2 mL) was added phenyl boronic acid (100 mg, 0.82 mmol), 1M Na$_2$CO$_3$ solution (1 mL) followed by Pd(PPh$_3$)$_4$. The resulting reaction mixture was refluxed in a pressure tube. After 2 h the mixture was cooled to 23° C., diluted with ethyl acetate, washed with water, brine, dried over anhydrous Na$_2$SO$_4$, filtered and concentrated in vacuo. The residue was purified by flash chromatography using 10% ethyl acetate-hexanes to give the biaryl product.

To a solution of this ester intermediate (85 mg, 0.35 mmol) in THF (1 mL) was added MeOH (1 mL) and 5N NaOH (1 mL). After stirring for 1 h, the reaction mixture was neutralized to pH=7 by the addition of 1N HCl. The resulting mixture was extracted with ethyl acetate, and the organic phase was dried over anhydrous Na$_2$SO$_4$, filtered and concentrated in vacuo. The acid was used in the next step without any further purification. This acid intermediate was coupled to methyl- 2-amino-cyclohexene using the similar procedures as described in the Examples above. Example 4 was prepared by saponification of the penultimate ester using similar procedures as described in the Examples above. $^1$H NMR (500 MHz, CD$_3$OD) δ 1.6 (m, 4H), 2.3 (m, 2H), 2.68 (t, 2H), 2.85 (m, 2H), 3.01 (t, 2H), 7.2 (d, 1H), 7.35 (m, 2H), 7.45 (m, 4H), 7.58 (d, 2H); LCMS m/z 348 (M−1).

Example 5

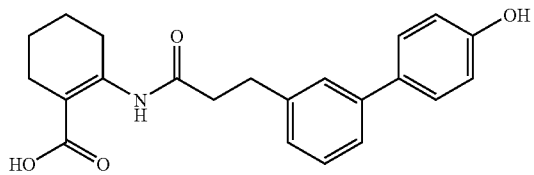

The coupling of 3-(3-bromophenyl) propionic acid with methyl 2-aminocyclohex-1-ene-1-carboxylate followed the similar procedures as described in the Examples above. To a solution of this aryl bromide intermediate (50 mg, 0.136 mmol) and 4-hydroxy-phenyl boronic acid (28 mg, 0.2 mmol) in THF (0.5 mL), was added K$_2$CO$_3$ (0.5 mL, 1.0M solution), followed by 1,1(bis-tert-butyl-phosphino) ferrocene palladium dichloride ligand. The reaction vessel was flushed with N$_2$ and heated to 85° C. After 30 min, the reaction mixture was cooled to RT and diluted with ethyl acetate. The resulting mixture was washed with water, brine, dried over anhydrous Na$_2$SO$_4$, filtered and concentrated in vacuo. The residue was purified by flash chromatography using 15% ethyl acetate-hexanes as the eluant to obtain the hydroxy biaryl methyl ester.

This intermediate ester was saponified following similar procedures described in the Examples above. $^1$H NMR (500 MHz, DMSO-d$_6$) δ 1.55 (m, 4H), 2.24 (m, 2H), 2.63 (t, 2H), 2.80 (bt, 2H), 2.9 (t, 2H), 6.83 (d, 2H), 7.13 (d, 1H), 7.33 (t, 1H), 7.38 (d, 1H), 7.42 (s, 1H), 7.45 (d, 2H), 9.52 (s, 1H); LCMS m/z 364 (M−1).

Example 6

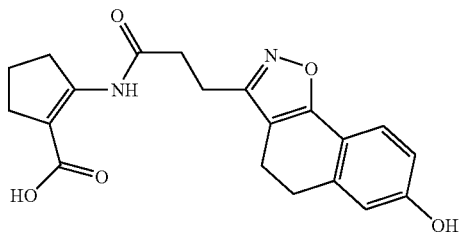

To a solution of diisopropylamine (5.3 g, 52 mmol) in 200 mL of THF was added n-butyllithium (22.4 mL, 56 mmol, 2.5 M in hexane) at −78° C. The resulting solution was stirred at −78° C. for 30 min, and then at RT for an additional 30 min. The solution was re-cooled to −78° C., and to this solution, was added dropwise a solution of tetralone 20 (7.03 g, 39.9 mmol) in 80 mL of THF. After 1 h at −78° C., to the above solution was added 4-chloro-4-oxobutyrate (8.43 g, 6.84 mL, 56 mmol) in one portion. The resulting solution was warmed to 23° C. over 2 h. The solvent was then evaporated, and the residue was diluted with 200 mL of THF/MeOH/water (v:v:v=3:1:1). To this mixture was added 100 mL of lithium hydroxide (1 M in water), and the resulting solution was stirred overnight. After removing some solvent in vacuo, the remaining aqueous layer was extracted with ethyl acetate. The aqueous phase was acidified with HCl until pH=3. The mixture was extracted with ethyl acetate, and the combined organic fractions were dried with sodium sulfate and concentrated in vacuo to give the ketoacid as a grey solid.

To a solution of this ketoacid intermediate (0.72 g, 2.6 mmol) in 15 mL of ethanol were added hydroxylamine hydrochloride (0.22 g, 3.1 mmol.) and triethylamine (320 mg, 0.44 mL, 3.1 mmol). The resulting mixture was heated at reflux for 5 h. After removing ethanol in vacuo, the residue was diluted with ethyl acetate (100 mL) and 1N HCl (20 mL). The aqueous layer was further extracted with 30% of isopropanol in chloroform (2×30 mL). The organic fractions were combined, dried with sodium sulfate and concentrated in vacuo to give the tricycle as a pale yellow solid. This intermediate was dissolved in dichloromethane (20 mL) and borontribromide (10 mL, 1 M in dichloromethane) was added at 0° C. The resulting dark solution was stirred at room temperature for 4 h before it was quenched with 100 mL of water at 0° C. The mixture was extracted with 30% isopropanol in chloroform. The aqueous layer contained a lot of product as a yellow solid, which was collected by filtration. The aqueous layer was further extracted with 30% isopropanol in chloroform. The organic phase was dried with sodium sulfate and concentrated in vacuo to give the hydroxy product as a yellow solid after reverse phase-HPLC purification.

To a solution of this hydroxy acid intermediate (110 mg, 0.42 mmol) in 15 mL of dichloromethane were added imidazole (87 mg, 1.3 mmol) and tert-butyldimethylsilyl chloride (192 mg, 1.3 mmol.) at RT. The resulting mixture was stirred for 4 h. The mixture was then purified by Biotage to give the product as a colorless oil.

To a solution of this bis-silyl intermediate (50 mg, 0.10 mmol) in 3 mL of dichloromethane were added 1 drop of DMF and oxalyl chloride (0.13 mL, 0.25 mmol, 2 M in dichloromethane) at 0° C. After 2 h at 0° C., the mixture was warmed to room temperature and stirred for 30 min. The volatiles were removed in vacuo, and to the residue was added 2 mL of dichloromethane followed by methyl 2-aminocyclopent-1-ene-1-carboxylate (35 mg, 0.25 mmol). The mixture was stirred overnight and then DMAP (10 mg) was added. The resulting mixture was stirred for an additional 2 h. The crude mixture was directly purified by Biotage (2-10% ethyl acetate/hexane) to give the amide product as a colorless oil.

To a solution of this silyl ether methyl ester intermediate (14 mg, 0.023 mmol, 23%) in 5 mL of THF/MeOH/water (v:v:v=3:1:1), was added 1 N sodium hydroxide (1 mL) and 3 drops of TBAF (1 M in THF). After 5 min at 23° C., the mixture was concentrated in vacuo and the residue was dissolved in DMSO, which was purified by reverse phase HPLC (Gilson) to give a colorless oil. This material was then dissolved in 3 mL of THF/MeOH/water (v:v:v=3:1:1). To this solution was added lithium hydroxide (2 mL, 1 M in water). The resulting mixture was stirred at room temperature for 3 h. The mixture was concentrated and dissolved in DMSO. The mixture was purified by reverse phase HPLC (Gilson) to provide Example 6 as a light brown solid. $^1$H NMR (acetone-d$_6$, 500 MHz) δ 10.4 (1H, s), 7.44 (1H, d), 6.85 (s, 1H), 6.80 (1H, dd), 3.13 (2H, t), 2.98 (4H, q), 2.83 (2H, t), 2.73 (2H, t), 2.49 (2H, t), 1.87 (2H, t); LCMS m/z 369 (M+1).

Examples 7-15

The following compounds were prepared under conditions similar to those described in Examples 1-6 above and illustrated in Schemes 1-6. Example 15 utilized triethylamine as base instead of imidazole/DMAP described for the TBSCl silylation step in Example 6.

| Example | | LCMS |
|---|---|---|
| 7 | 2-[3-(naphthalen-1-yl)propanamido]cyclohex-1-enecarboxylic acid | 322 (M − 1) |
| 8 | 5-methyl-2-[3-(naphthalen-2-yl)propanamido]cyclohex-1-enecarboxylic acid | 336 (M − 1) |
| 9 | 2-[3-(biphenyl-4-yl)propanamido]cyclohex-1-enecarboxylic acid | 348 (M − 1) |
| 10 | 2-{3-[2'-hydroxybiphenyl-3-yl]propanamido}cyclohex-1-enecarboxylic acid | 364 (M − 1) |
| 11 | 2-{3-[3'-hydroxybiphenyl-3-yl]propanamido}cyclohex-1-enecarboxylic acid | 364 (M − 1) |
| 12 | 2-{3-[3'-aminobiphenyl-3-yl]propanamido}cyclohex-1-enecarboxylic acid | 363 (M − 1) |
| 13 | 2-{3-[3-(2,3-dihydrobenzofuran-6-yl)phenyl]propanamido}cyclohex-1-enecarboxylic acid | 390 (M − 1) |

| Example | | LCMS |
|---|---|---|
| 14 | [structure] | 334 (M − 1) |
| 15 | [structure] | 383 (M + 1) |

NMR Data for Selected Examples

Example 7

$^1$H NMR (500 MHz, DMSO-d$_6$) δ 1.5 (m, 4H), 2.2 (bt, 2H), 2.65 (t, 2H), 2.8 (bt, 2H), 3.34 (t, 2H), 7.4 (m, 2H), 7.54 (m, 2H), 7.78 (d, 1H), 7.92 (d, 1H), 8.08 (d, 1H).

Example 8

$^1$H NMR (500 MHz, CD$_3$OD) δ 0.9 (d, 3H), 1.3 (m, 1H), 1.57 (m, 1H), 1.7 (m, 1H), 2.24 (m, 1H), 2.35 (m, 1H), 2.45 (m, 1H), 2.7 (t, 2H), 3.05 (dd, 1H), 3.1 (t, 2H), 7.34-7.43 (m, 3H), 7.65 (s, 1H), 7.72 (m, 3H).

Example 9

$^1$H NMR (500 MHz, DMSO-d$_6$) δ 1.55 (m, 4H), 2.2 (bt, 2H), 2.6 (t, 2H), 2.8 (bt, 2H), 2.9 (t, 2H), 7.3 (m, 3H), 7.44 (t, 2H), 7.56 (d, 2H), 7.62 (d, 2H), 11.6 (bs, 1H).

Example 10

$^1$H NMR (500 MHz, DMSO-d$_6$) δ1.55 (m, 4H), 2.4 (t, 2H), 2.62 (t, 2H), 2.84 (bt, 2H), 2.9 (t, 2H), 6.85 (t, 1H), 6.95 (d, 1H), 7.15 (m, 2H), 7.22 (d, 1H), 7.3 (t, 1H), 7.38 (m, 2H), 9.4 (s, 1H), 11.6 (s, 1H), 12.55 (bs, 1H).

Example 11

$^1$H NMR (500 MHz, DMSO-d$_6$) δ 1.55 (m, 4H), 2.24 (bt, 2H), 2.66 (t, 2H), 2.82 (bt, 2H), 2.94 (t, 2H), 6.75 (d, 1H), 6.9 (m, 1H), 7.05 (d, 1H), 7.25 (m, 2H), 7.35 (t, 1H), 7.4 (d, 1H), 7.45 (s, 1H), 9.49 (s, 1H).

Example 12

$^1$H NMR (500 MHz, DMSO-d$_6$) δ 1.55 (m, 4H), 2.22 (bt, 2H), 2.62 (t, 2H), 2.8 (bt, 2H), 2.9 (t, 2H), 6.9 (d, 1H), 7.2 (m, 3H), 7.3-7.4 (m, 3H), 7.44 (s, 1H), 11.6 (s, 1H).

Example 13

$^1$H NMR (500 MHz, DMSO-d$_6$) δ 1.55 (m, 4H), 2.2 (m, 2H), 2.6 (t, 2H), 2.8 (m, 2H), 2.9 (t, 2H), 3.2 (t, 2H), 4.55 (t, 2H), 6.82 (d, 1H), 7.14 (d, 1H), 7.3 (t, 1H), 7.39 (m, 2H), 7.42 (s, 1H), 7.49 (s, 1H), 11.62 (s, 1H), 12.5 (bs, 1H).

Example 14

$^1$H NMR (500 MHz, DMSO-d$_6$) δ 1.75 (m, 2H), 2.35 (bt, 2H), 2.7 (t, 2H), 2.85 (t, 2H), 3.02 (t, 2H), 7.35 (m, 3H), 7.44 (t, 2H), 7.56 (d, 2H), 7.62 (d, 2H).

Example 15

$^1$H NMR (acetone-d$_6$, 500 MHz) δ 11.8 (1H, s), 7.43 (1H, d), 6.81 (1H, d), 6.80 (1H, dd), 2.96 (8H, m), 2.72 (4H, q), 1.61 (4H, m).

Example 16

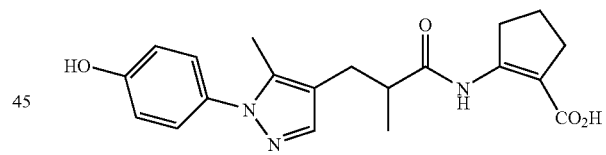

A solution of the aldehyde intermediate (1.45 g, 6.7 mmol), ethyl triphenylphosphonium methyl acetate (3.1 g, 8.1 mmol) in 15 mL of toluene was heated at 130° C. for 16 h. The mixture was directly purified by Biotage (5-20% ethyl acetate in hexane) to give the enoate as a light yellow solid.

This enoate intermediate (1.74 g, 5.8 mmol) and Pd/C (10%, 170 mg) in 200 mL of methanol was stirred under 1 atm of hydrogen gas (balloon) for 12 h. The slurry was filtered and concentrated in vacuo. The residue was dissolved in ethanol/methanol (1:1) and purified by chiral OJ-H (9 mL/min, 28% isopropanol/heptane, isocratic, 40 min/run) to give the enantiomers as white solids. Elution times of these enantiomeric intermediates were 18 min and 22 min using analytical Chiralcel-OJ, (25% isopropanol in heptane, isocratic).

The ethyl ester enantiomer (400 mg, 1.32 mmol.) was combined with concentrated HCl (2 mL) and 4 mL of acetic acid, and was heated at 80° C. for 3 h. The mixture was concentrated in vacuo, and to it was added 15 mL of water. The mixture was extracted with 30% isopropanol/chloroform. The organic layer was dried with sodium sulfate and concentrated in vacuo to give the acid product as a white solid.

To a solution of the methyl ether (410 mg, 1.50 mmol) in 20 mL of dichloromethane was added borontribromide (7.5 mL, 1 M in dichloromethane) at 0° C. The mixture was warmed to RT and stirred for 18 h. The mixture was quenched with water at 0° C. and concentrated in vacuo without further purification.

To a solution of the phenol in 60 mL of dichloromethane were added TBSCl (0.57 g, 3.8 mmol), imidazole (0.26 g, 3.8 mmol) and DMAP (37 mg, 0.3 mmol). The mixture was stirred at 23° C. for 5 h. The mixture was concentrated and purified by RP-HPLC to give monosilyl ether (0.37 g), which was resubmitted to a solution of TBSCl (225 mg), triethylamine (0.21 mL) and DMAP (20 mg) in 15 mL of dichloromethane. The reaction mixture was stirred for 3 h and washed with brine. The mixture was then dried with sodium sulfate and concentrated in vacuo to give the bis-silylated intermediate as a crude brown oil. Following the previously described amide formation and hydrolysis procedures using oxalyl chloride and lithium hydroxide respectively, the enantiomers of Example 16 were obtained. $^1$H NMR (methanol-$d_4$, 500 MHz) δ 7.41 (1H, s), 7.16 (2H, d), 6.88 (2H, d), 3.07 (2H, m), 2.73 (3H, m), 2.46 (2H, m), 2.15 (3H, s), 1.87 (2H, m), 1.23 (3H, d); LCMS m/z 370 (M+1).

Example 17

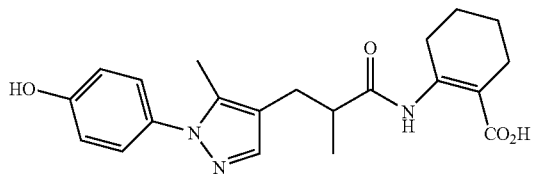

The enantiomers of Example 17 were prepared under similar conditions as described in the Examples above. $^1$H NMR (methanol-$d_4$, 500 MHz) δ 7.43 (1H, s), 7.18 (2H, dd), 6.89 (2H, dd), 2.86 (2H, m), 2.76 (1H, dd), 2.63 (1H, dd), 2.58 (1H, m), 2.30 (2H, m), 2.16 (3H, s), 1.60 (4H, m), 1.23 (3H, d); LCMS m/z 384 (M+1).

Example 18

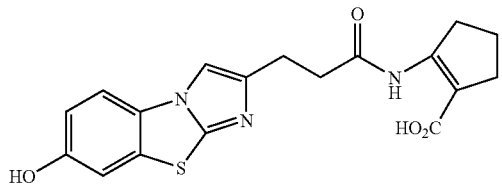

A mixture of the methoxy aminobenzothiazole (8.5 g, 47 mmol.) and ethyl α-bromopyruvate (12.9 g, 59 mmol) was heated in 120 mL of DME under reflux for 2 h. After cooling to RT, the precipitate was collected by filtration to afford the product as a yellow solid, which was then heated in a solution of ethanol (200 mL) under reflux for 4 h. The partitioning of the resulting residue after concentration using ethyl acetate and saturated aqueous sodium carbonate solution gave an organic fraction, which was dried with sodium sulfate. The concentration in vacuo led to the tricyclic intermediate as a solid.

To a solution of this ester (2.67 g, 9.65 mmol) in 100 mL of dichloromethane was added DIBALH (14.5 mL, 1 M in hexane, 14.5 mmol) at −78° C. After 1 h at −78° C., the mixture was quenched with water and slowly warmed to 23° C. A saturated aqueous Rochelle's salt solution was added, and the mixture turned clear overnight. The organic phase was washed with water and concentrated. The resulting residue was filtered to give the aldehyde as a yellow solid.

To a solution of trimethyl phosphonoacetate (0.71 mL, 4.33 mmol) in 40 mL of THF was added nBuLi (2.9 mL, 4.6 mmoL, 1.6 M in hexane) at 0° C. After 30 min, to the solution was added the aldehyde (0.67 g, 2.88 mmol). After 10 min, the mixture was quenched with water and diluted with ethyl acetate. The organic phase was concentrated and purified by Biotage (20-30% ethyl acetate/hexane) to give the enoate as a white solid.

To a solution of this enoate intermediate (0.43 g, 1.49 mmol) in 200 mL of methanol was added tosylhydrazide (2.77 g, 14.9 mmol). The mixture was heated under reflux for overnight. The resulting clear solution was concentrated and purified by Gilson to give the product as a white solid.

To a solution of this ester (230 mg) in 50 mL of THF/MeOH/water (v:v:v=3:1:1) was added 10 mL of 1 N aqueous LiOH solution. After 1.5 h, the mixture was acidified using HCl to pH=4. The mixture was extracted with 30% of isopropanol in chloroform. The organic phase was concentrated to dryness to give the acid as a white solid.

To a solution of the methyl ether (220 mg, 0.80 mmol) in 40 mL of dichloromethane was added borontribromide (6.4 mL, 1 M in dichloromethane) at 0° C. The mixture was warmed to RT and stirred for 12 h. The mixture was quenched with water at 0° C. and washed with 30% of isopropanol in chloroform. After concentration of the organic solvent, the product was obtained as a solid.

To a solution of this phenol in 60 mL of dichloromethane were added TBSCl (380 mg) and triethylamine (3 mL). The reaction mixture was stirred for 3 h and washed with water. After concentration of the organic fraction, the residue was purified by RP-HPLC to give the mono-TBS product (0.26 g), which was resubmitted to a solution of TBSCl (156 mg), triethylamine (0.24 mL) and DMAP (13 mg) in 60 mL of dichloromethane. The reaction mixture was stirred at 0° C. for 1 hr, and to the mixture was added additional 1 equivalent of triethylamine and TBSCl. The solution was stirred overnight at RT before it washed with water. The organic phase was then dried with sodium sulfate and concentrated in vacuo to give the bis-silylated product as a crude brown oil. Following the previously described amide formation and hydrolysis procedures using oxalyl chloride and lithium hydroxide respectively, Example 18 was obtained. $^1$H NMR (methanol-$d_4$, 500 MHz) δ 8.13 (1H, s), 7.88 (1H, d), 7.41 (1H, d), 7.11 (1H, dd), 3.16 (4H, m), 2.89 (2H, t), 2.50 (2H, t), 1.91 (2H, m); LCMS m/z 372 (M+1).

Example 19

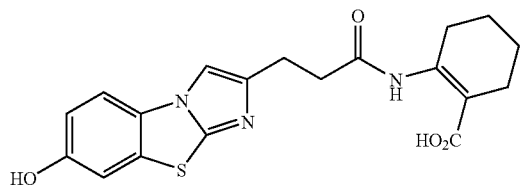

Example 19 was prepared under similar conditions as described in the Examples above. $^1$H NMR (methanol-$d_4$, 500 MHz) δ 8.04 (1H, s), 7.83 (1H, d), 7.37 (1H, d), 7.08 (1H, dd), 3.12 (2H, t), 2.93 (2H, m), 2.81 (2H, t), 2.34 (2H, m), 1.65 (4H, m); LCMS m/z 386 (M+1).

Example 20

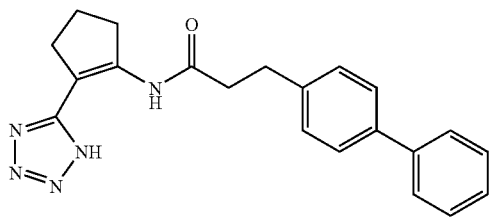

To a solution of adiponitrile (0.569 mL, 5.0 mmol) in anhydrous THF cooled to −78° C. under a nitrogen atmosphere, was added LDA (2.62 mL, 5.25 mmol, 2.0 M solution in THF). The reaction was warmed to −20° C. over 10 min, and then quenched with saturated NH$_4$Cl solution. The resulting mixture was extracted with ethyl acetate. The organic layer was washed with brine, dried over anhydrous Na$_2$SO$_4$, filtered and concentrated in vacuo. This material was purified by flash chromatography using 15% ethyl acetate-hexanes as the eluant to give the cyclopentene aminonitrile as an off white solid. This intermediate cyclopentene aminonitrile was coupled with 3-(4-bromophenyl) propionic acid, using similar procedures as described in the Examples above, to provide the amide bromide.

To a solution of this arylbromide intermediate (88 mg, 0.28 mmol) in THF (0.5 mL) was added phenyl boronic acid (48 mg, 0.41 mmol) followed by 1M K$_2$CO$_3$ (0.5 mL) and 1,1bis(di-tert-butylphosphino)ferrocene palladium dichloride ligand (18 mg, 0.03 mmol). After stirring the reaction in a sealed tube at 85° C. for 18 h, it was diluted with ethyl acetate, washed with H$_2$O and saturated NaCl. The organic layer was dried over anhydrous Na$_2$SO$_4$, filtered and concentrated in vacuo. The residue was purified by flash chromatography using 10% ethyl acetate-hexanes to give the biaryl intermediate as a colorless oil.

To a solution of this intermediate nitrile (34 mg, 0.11 mmol) in a 2:1 mixture of dioxane-H$_2$O (0.9 mL) was added sodium azide (21 mg, 0.32 mmol) and zinc bromide (29 mg, 0.13 mmol). The reaction mixture was stirred at 120° C. in a sealed tube for 18 h. The mixture was then cooled to room temperature and 1N HCl was added until the pH=7. The reaction mixture was concentrated in vacuo and purified by reverse phase HPLC (Gilson) to provide Example 20. $^1$H NMR (500 MHz, CD$_3$OD) δ 2.02 (m, 2H), 2.46 (m, 2H), 2.85 (m, 2H), 3.15 (m, 4H), 7.18 (d, 2H), 7.31 (t, 1H), 7.41 (t, 2H), 7.52 (d, 2H), 7.56 (t, 2H); LCMS m/z 360 (M+1).

Example 21

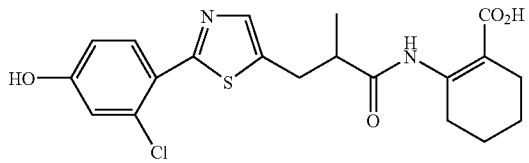

To the commercially available thiazole bromo aldehyde (4.97 g) shown in Scheme 10, in 200 mL of methanol was added NaBH$_4$ (0.98 g) in portions at 0° C. The mixture was stirred for 2 h and concentrated. The residue was suspended in saturated NH$_4$Cl solution (200 mL) to adjust the pH to 6. The mixture was then basified by NaOH (aq) to pH 11 before the extraction with ethyl acetate (4×200 mL). The combined organic fractions were dried with sodium sulfate and concentrated to give the alcohol.

To a solution of this hydroxy intermediate (4.91 g) in 120 mL of dichloromethane at 0° C. was added triphenylphosphine (9.96 g). To this solution was then added dropwise, carbon tetrabromide (12.6 g) in 30 mL of dichloromethane. After 2.5 h at 23° C., the mixture was stirred at −20° C. overnight. The solvent was then removed, and the residue was purified by Biotage (5-10% ethyl acetate in hexane) to give the bromide as a white solid.

To a solution of diethyl methylmalonate (5.19 g) in 100 mL of THF was added NaH (1.2 g, 60%) at 0° C. in portions. The mixture was stirred at 0° C. for 10 min, and to this solution was then added the bromide intermediate (3.84 g) in one portion. The mixture was warmed to 23° C. and stirred for 1 h before the addition of water. The resulting mixture was extracted with ethyl acetate, concentrated and purified by Biotage (5-10% ethyl acetate in hexane) to give the diester containing some diethyl methyl malonate contaminant as a crude oil.

To this diester (5 g) was added THF/MeOH/water (~100 mL, 3:1:1), LiOH (~50 mL, 1 N) at 23° C. The resulting solution was stirred overnight. After the removal of the organic solvent, to the residue was added concentrated HCl until pH=4. The mixture was extracted with ethyl acetate (5×100 mL). The combined organic layers were dried with sodium sulfate and concentrated to give the diacid as a white solid containing some α-methyl malonate acid contaminant.

The solution of this diacid intermediate (4.9 g) in 20 mL of DMF was heated at 150° C. for 7 min and then cooled to 0° C. The solution was diluted with ethyl acetate, washed with brine, dried with sodium sulfate and concentrated to give the monoacid containing some propanoic acid. The mixture was further purified by RP-HPLC to give pure alpha-methylacid as a colorless oil.

The mixture of this bromoacid intermediate (0.71 g), the aryl boronic acid (0.67 g), Pd(PPh$_3$)$_4$ (323 mg), NaHCO$_3$ solution (11.2 mL, 1 N) and dioxane (40 mL) was heated at 100° C. under nitrogen overnight in a sealed tube. The mixture was then partitioned between ethyl acetate and 1 N NaOH solution. The organic layer was washed with 1 N NaOH solution. The combined aqueous layers were acidified with concentrated HCl until pH=4-5. The resulting mixture was extracted with ethyl acetate three times. The combined organic layers were washed with brine and dried with sodium sulfate. The removal of solvent afforded the biaryl product.

To a solution of the methoxyaryl intermediate (0.88 g) in 60 mL of dichloromethane was added BBr$_3$ (22.7 mL, 1 M in dichloromethane) at 0° C. The mixture was warmed to room temperature and stirred overnight. To the mixture was then added water at 0° C., and the mixture was extracted with 30% isopropanol in chloroform. After concentrating the organic layer, the residue was hydrolyzed with LiOH (1 N) in 3:1:1 THF/MeOH/water for 2 h. After the removal of the organic solvent, the residue was washed with ethyl acetate. The alkaline aqueous phase was acidified with HCl until pH=4-5, and the mixture extracted with ethyl acetate (2×). The combined organic layers were washed with brine, dried with sodium sulfate and concentrated to give the phenol as a brown solid.

To a mixture of this phenolic acid intermediate (0.51 g) in 10 mL of dichloromethane was added triethylamine (0.84 mL). To this solution at 0° C. was added tert-butyldimethylsilyl chloride (0.91 g) and DMAP (42 mg). After 6 h at 23° C., the mixture was washed with water, brine and dried with sodium sulfate. The resulting organic fraction was concentrated in vacuo. To the resulting residue in dichloromethane (40 mL) was added one drop of DMF, and then a solution of oxalyl chloride (4 mL, 2 N in dichloromethane). The mixture was warmed to 23° C. and stirred for additional 4 h. The resulting mixture was concentrated in vacuo and then dissolved in dichloromethane (28 mL). To the resulting solution was then added the enamine fragment (717 mg) as in the examples above. The resulting mixture was stirred for overnight. The crude material was purified by RP-HPLC to give 430 mg of amide. To the resulting amide was added 6 mL of THF:methanol:water (3:1:1) and a solution of lithium hydroxide (10 mL, 1N). After 5 h, most of the low boiling solvent was removed in vacuo. To the residue was added concentrated HCl until pH=3. The mixture was extracted with 30% isopropanol in chloroform. The organic layer was concentrated and purified by RP-HPLC to give the desired Example 21. $^1$H NMR (DMSO-$d_6$, 500 MHz) δ 12.6 (1H, s), 11.6 (1H, s), 10.4 (1H, s), 7.95 (1H, d), 7.62 (1H, s), 6.94 (1H, d), 6.85 (1H, dd), 3.10 (1H, dd), 2.89 (1H, dd), 2.79 (2H, m), 2.62 (1H, m), 2.20 (2H, m), 1.52 (4H, m), 1.15 (3H, d); LCMS m/z 421 (M+1).

Example 22

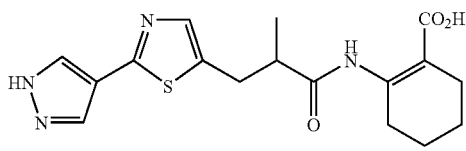

To the intermediate alpha-methylacid bromothiazole above (197 mg, Compound 52 in Scheme 11) in dichloromethane (10 mL) was added one drop of DMF, and then a solution of oxalyl chloride (1.6 mL, 2 N in dichloromethane). The mixture was warmed to room temperature and stirred for 1 h. The resulting mixture was concentrated in vacuo and then dissolved in dichloromethane (10 mL). To the resulting solution was then added the common 2-aminocyclohex-1-ene-1-carboxylate ester (400 mg). The resulting mixture was stirred overnight. The crude material was purified by Biotage (5-10% ethyl acetate in hexane) to give the amide as a colorless oil.

The mixture of this bromo intermediate (55 mg), phosphine ligand (14 mg), $K_2CO_3$ (440 mg, in 3.2 mL of water) in THF (4 mL) was degassed with argon followed by the addition of boronate ester (35 mg). The mixture was heated at 55° C. for 1 h and then 65° C. overnight. The resulting mixture was partitioned between ethyl acetate and brine. The organic layer was dried with sodium sulfate and purified by RP-HPLC to give the biaryl product. The similar hydrolysis procedure as described in the Examples above gave Example 22 as a white solid. $^1$H NMR (DMSO-$d_6$, 500 MHz) δ 11.6 (1H, s), 8.05 (1H, s), 7.43 (1H, d), 3.04 (1H, dd), 2.90 (1H, dd), 2.76 (2H, m), 2.58 (1H, m), 2.18 (2H, m), 1.50 (4H, m), 1.13 (3H, d); LCMS m/z 361 (M+1).

Example 23

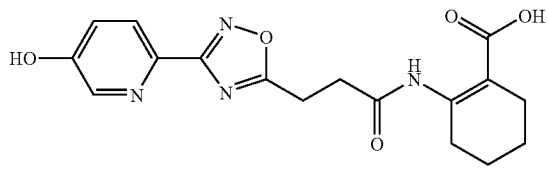

To NaH (7.2 g, 60%) was added DMF (100 mL) followed by 4-methoxybenzyl alcohol (18.7 mL) at 0° C. After 25 min at 0° C., the mixture was warmed to 23° C. and stirred for additional 30 min. To the resulting solution was added the pyridyl cyanobromide (22.9 g) in one portion. The reaction was exothermic and stirred for 10 min before it was cooled to room temperature. The mixture was diluted with 500 mL of ethyl acetate, washed with water (500 mL×3). The first two aqueous phases were extracted with dichloromethane (500 mL×2). The combined dichloromethane phase was washed with water (500 mL×3). The combined organic phases were dried over sodium sulfate and concentrated to give the PMB ether as a white solid.

To the suspension of this intermediate (24.6 g) and hydroxylamine hydrochloride (8.55 g) in ethanol (500 mL) was added NaOH (4.92 g in 50 mL of water) dropwise. The mixture was stirred at RT overnight. The solid was collected by filtration to give the N-hydroxy amidine as a white solid.

To this amidine intermediate (15.4 g) was added pyridine (40 mL) and the acid chloride shown in Scheme 12 (8.3 mL). The mixture was heated at 120° C. for 2 h and then 130° C. for 1 h. After removing most pyridine, the residue was partitioned between water and dichloromethane. The organic phase was washed with water four times and then dried with sodium sulfate. After removing the solvent, to the residue was added some methanol. The resulting slurry was filtered. The solid collected by the filtration was washed with methanol and dried in vacuo to give the methyl ester intermediate as a pale pink solid.

To this ester (30 g) suspended in 3:1:1 THF/MeOH/water (700 mL) was added LiOH (300 mL, 1 N). The mixture was stirred at RT for 1 h. After removing most of the solvent, the aqueous layer was acidified to pH=3. Filtration of the resulting slurry gave a white solid, which was washed with water, diethyl ether and azeotroped with toluene to give the acid as a white solid.

To a mixture of this acid (26.9 g) in 300 mL of dichloromethane were added 0.1 mL of DMF, and then a solution of oxalyl chloride (76 mL, 2 N in dichloromethane) at 0° C. After 0.5 h, the mixture was warmed to RT and stirred for additional 0.5 h. The resulting mixture was concentrated in vacuo and then dissolved in dichloromethane (250 mL). To the resulting solution was then added the methyl 2-aminocyclohex-1-ene-1-carboxylate (29 g). The resulting mixture was stirred for overnight. The solution was then washed with water (200 mL), saturated sodium bicarbonate solution (200 mL) and dried with sodium sulfate to give the amide as a crude material.

To a solution of the PMB ether intermediate (10.2 g) in 50 mL of dichloromethane was added triisopropylsilane (12.3 mL) and trifluoroacetic acid (20 mL) dropwise. The mixture was stirred at RT for 10 min, and the solvent was removed in vacuo. To the residue containing this hydroxy product was added 300 mL of THF:methanol:water (3:1:1) followed by a solution of lithium hydroxide (200 mL, 1N). After 12 h, most of the low-boiling solvent was removed in vacuo. To the residue was added ethyl acetate (200 mL×2), then the aqueous layer was neutralized to pH=5. The precipitate was collected by filtration to give the desired Example 23 as a light brown solid. $^1$H NMR (DMSO-$d_6$, 500 MHz) δ 12.6 (1H, s), 11.7 (1H, s), 10.6 (1H, s), 8.25 (1H, d), 7.88 (1H, d), 7.29 (1H, dd), 3.18 (2H, t), 2.89 (2H, t), 2.48 (2H, m), 2.21 (2H, m), 1.51 (4H, m); LCMS m/z 359 (M+1).

Example 24

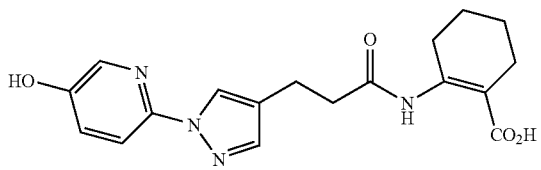

To a flask containing 20 mL diglyme and KH (1.33 g, 30%) at room temperature was added methylpyrazole (820 mg) in one portion. After 2 h, to this mixture was added the pyridyl nitrobromide (1.83 g). The mixture was then heated at 130° C. overnight. To the resulting mixture was added 100 mL of water and 100 mL of ethyl acetate. The aqueous layer was extracted with 100 mL of dichloromethane. The combined organic layers were dried with sodium sulfate and concentrated in vacuo to give a green slurry. To the slurry was added hexane to remove the mineral oil. The mixture was then filtered to give the pyridylpyrazole as a green solid.

The mixture of this methylated intermediate (204 mg), NBS (330 mg) and 5 mL of $CCl_4$ under light was refluxed for 3.5 h. The mixture was filtered and the filtrate was washed with saturated aqueous sodium sulfite (100 mL). The mixture was extracted with 30% of isopropanol in chloroform. The organic layer was washed with water, dried with sodium sulfate and concentrated. The residue was purified by Biotage eluting with 5-30% ethyl acetate in hexane/dichloromethane to give the bromide as a light yellow solid.

To NaH (350 mg, 60%) in 20 mL of THF was added dimethyl malonate (1.14 g) at 0° C. After 20 min, to the clear solution was added the bromomethylene intermediate (490 mg) in 10 mL of THF dropwise. The mixture was warmed to RT and stirred for additional 1 h. To the mixture was then added water (50 mL). The mixture was extracted with ethyl acetate (200 mL). The combined organic layers were concentrated, and the residue was submitted to 10 mL of LiOH (1N) and 50 mL of THF/MeOH/water (3:1:1). After 3 h, the mixture was acidified to pH=4 using concentrated HCl. The mixture was concentrated to remove organic solvents, and the residue was extracted with 30% isopropanol in chloroform. The organic layer was concentrated and purified by RP-HPLC to give the acidester. The mixture of this alpha-carboxyacid (1 g) in 10 mL of DMF was heated at 150° C. for 10 min. The mixture was then purified by RP-HPLC to give the monoester (880 mg) as a yellow solid. To this nitro intermediate (100 mg) in 6 mL of acetic acid was added Zn (234 mg). The slurry was heated at 60° C. for 30 min and filtered through celite. The filtrated was purified by RP-HPLC to give the amino methyl ester as a reddish oil.

To the mixture of this aminopyridine (580 mg), sodium nitrite (200 mg) was added in 2.5 mL of 10% sulfuric acid. The mixture was heated at 80° C. for 1 h. The mixture was purified by RP-HPLC to give the hydroxypyridine. To this hydroxyacid (86 mg) was added 5 mL of dichloromethane, 0.18 mL of triethyl amine and 139 mg of TBSCl. After 3 h, to the mixture was added water. The mixture was extracted with dichloromethane and 30% isopropanol in chloroform. The combined organic fractions were dried with sodium sulfate and concentrated in vacuo. The resulting residue was dissolved in 5 mL of dichloromethane. To the solution was added 1 drop of DMF, and 1 mL of oxalyl chloride (2 M in dichloromethane) at 0° C. The resulting mixture was warmed to 23° C. and stirred for 30 min before the mixture was concentrated in vacuo. The residue was diluted into 5 mL of dichloromethane, and to the solution was added 100 mg of methyl 2-aminocyclohex-1-ene-1-carboxylate. The mixture was stirred overnight. The reaction mixture was concentrated, and to the residue was added 20 mL of THF/MeOH/water (3:1:1) and 8 mL of LiOH (1 N). The mixture was stirred at RT for 8 h and concentrated to a smaller volume. To the residue was added concentrated HCl dropwise until pH<3. The mixture was extracted with 30% isopropanol in chloroform. The organic fraction was concentrated and the residue was purified by RP-HPLC to give Example 24. $^1$H NMR (Acetone-$d_6$, 500 MHz) δ 11.7 (1H, s), 8.32 (1H, s), 8.01 (1H, s), 7.78 (1H, d), 7.56 (1H, s), 7.40 (1H, d), 2.93 (2H, m), 2.87 (2H, t), 2.63 (2H, t), 2.32 (2H, m), 1.60 (4H, m); LCMS m/z 357 (M+1).

Example 25

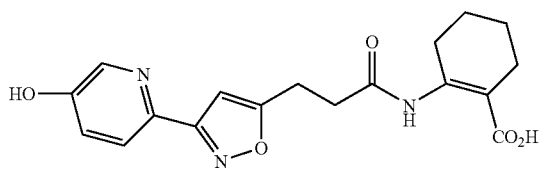

The cyanopyridine prepared above, was reduced with DIBAL-H under standard conditions, and the aldehyde (173 mg), in 5 mL of THF and 2 mL of water was combined with hydroxylamine hydrochloride (99 mg). The mixture was stirred for 5 h and concentrated in vacuo. The residue was purified by Biotage eluting with 5%-20% of ethyl acetate in 1:1 mixture of dichloromethane and hexane to give the oxime.

To this oxime (50 mg) and 4-pentynoic acid (76 mg) in 10 mL of dichloromethane at 0° C. was added 0.4 mL of NaOCl (>=4% in water). After 12 h, the solvent was removed, and to the residue was added 6 mL of DMF and 3 mL of NaOCl (>=4% in water). The mixture was stirred at RT for 2 days. The mixture was filtered, and the filtrate was purified with RP-HPLC to give the isoxazole.

To this PMB ether intermediate (42 mg), was added 1 mL of dichloromethane and 1 mL of TFA. After 30 min, the mixture was concentrated, and to the residue was added 10 mL of dichloromethane, 73 uL of triethyl amine and 48 mg of TBSCl. After 3 h, to the mixture was added water. The mixture was then extracted with dichloromethane and 30% isopropanol in chloroform. The combined organic fractions were dried with sodium sulfate and concentrated in vacuo. Following similar procedures as described in the Examples above, acylation and deprotection provided Example 25. $^1$H NMR (Acetone-$d_6$, 500 MHz) δ 11.8 (1H, s), 8.31 (1H, s), 7.94 (1H, s), 7.39 (1H, d), 6.73 (1H, s), 2.93 (2H, t), 2.82 (2H, t), 2.68 (2H, m), 2.33 (2H, m), 1.60 (4H, m); LCMS m/z 358 (M+1).

Example 26

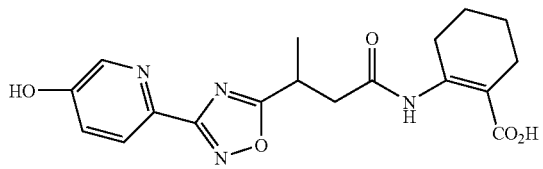

To the commercially available olefin (5 g) in 20 mL of propanol was added 0.5 mL of concentrated sulfuric acid. The mixture was heated at reflux for 2 days. The reaction mixture was purified by Biotage (5% ethyl acetate in hexane) to give the propyl ester as a colorless oil.

To a solution of this ester (4.8 g) and NMO (9.9 g) in 30 mL of dichloromethane was added $OsO_4$ (4.2 mL, 4% in water). The mixture was stirred for 12 h at RT. To the resulting solution was added water (150 mL) and dichloromethane (300 mL). The organic layer was concentrated. To the residue was added acetone (300 mL) and sodium periodate (14.4 g) in water (80 mL). A white slurry was formed. After 30 min, the slurry was filtered, and the filtrate was concentrated in vacuo. The residue was purified by Biotage (5% ethyl acetate in hexane) to give the corresponding aldehyde as a colorless oil. To this aldehyde was added t-butanol (25 mL), 2-methyl-2-butene (15 mL), a mixture of sodium chlorite (14.5 g, 80%) and sodium dihydrophosphate (18 g) in water (75 mL) at 0° C. The resulting brown solution was slowly warmed to 23° C. and stirred for 1.5 h. To this mixture was added NaOH (1 N) until pH=8. The organic layer was removed. To the aqueous layer was added concentrated HCl until pH=3. The mixture was then extracted with ethyl acetate (200 mL×3). The combined organic layers were dried to give the monoacid as a colorless oil.

To this acid intermediate (1 g) in 10 mL of toluene was added thionyl chloride (2 mL) at room temperature. The mixture was heated at 80° C. for 1 h, and the volatiles were removed and azetroped with toluene. The residue was then dissolved in pyridine (10 mL), and to the mixture was added the N-hydroxy amidine (1.0 g) described in the above Examples. The resulting mixture was heated at 120° C. for 2 h and then purified by Biotage (5-40% ethyl acetate in hexane) to give the oxadiazole as a brown oil. Following similar procedures described in the Examples above, acylation and deprotection gave the desired Example 26 as a white solid. $^1$H NMR (DMSO-$d_6$, 500 MHz) δ 11.6 (1H, s), 10.7 (1H, bs), 8.27 (1H, d), 7.90 (1H, d), 7.31 (1H, dd), 2.86 (1H, dd), 2.80 (1H, dd), 2.74 (3H, m), 2.22 (2H, m), 1.52 (4H, m), 1.37 (3H, d); LCMS m/z 373 (M+1).

Example 27

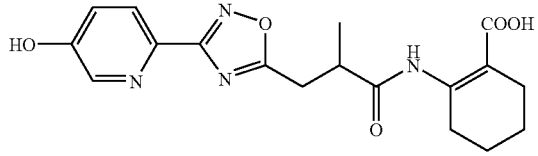

The similar procedures as described for the preparation of Example 26 above, gave the racemic oxadiazole ester intermediate shown below.

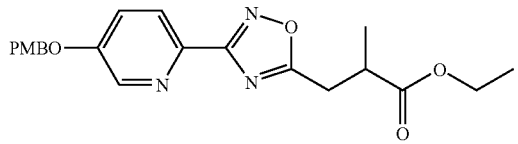

This oxadiazole intermediate (5 g) was purified by chrial AD-H to give two enantiomers. To each enantiomer (1.5 g) in 100 mL of THF/MeOH/water was added LiOH (15 mL, 1 N) at 0° C. After 30 min at 0° C., the mixture was acidified with HCl to pH=2-3. After the removal of the organic solvent in vacuo, the residue was extracted with 30% isopropanol in chloroform. The organic layer was dried with sodium sulfate. The removal of solvent in vacuo gave the acid containing some inorganic salt.

This material was submitted to amide formation following the same procedures as described in the Examples above, which was subsequently treated with dichloromethane (20 mL), triisopropylsilane (2 mL) and treated dropwise with TFA (10 mL). The resulting mixture was stirred at 0° C. for 25 min, and the mixture was concentrated in vacuo. The residue was dissolved in DMSO and purified by RP-HPLC to give an enriched single enantiomer of Example 27 (83% ee determined by chiral OJ-R). The same procedure starting with the opposite enantiomer gave enantiomerically enriched Example 27 (71% ee determined by chrial OJ-R).

These enantiomers of Example 27 were subsequently repurified and resolved by preparative SFC chiral chromatography (ChiralPak AD, 35% methanol(TFA)-$CO_2$) to obtain each enantiomer at 98-99% ee. Enantiomer A: $^1$H NMR (DMSO-$d_6$, 500 MHz) δ 11.7 (1H, s), 10.7 (1H, bs), 8.27 (1H, d), 7.88 (1H, d), 7.31 (1H, dd), 3.24 (1H, dd), 3.07 (1H, dd), 3.02 (1H, m), 2.75 (2H, m), 2.21 (2H, m), 1.51 (4H, m), 1.27 (3H, d); LCMS m/z 373 (M+1). Enantiomer B: $^1$H NMR ($CD_3$OD-$d_6$, 500 MHz) δ 8.25 (1H, d), 8.05 (1H, d), 7.42 (1H, dd), 3.34 (1H, dd), 3.12 (2H, m), 2.87 (2H, m), 2.34 (2H, m), 1.62 (4H, m), 1.37 (3H, d); LCMS m/z 373 (M+1).

Example 28

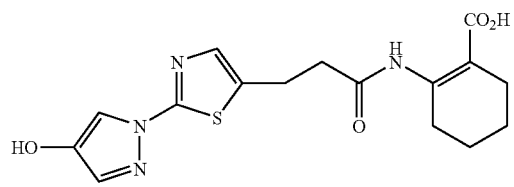

To a preheated (50° C.) slurry of copper (II) chloride (932 mg), 10 mL of acetonitrile was added, along with the thiazole aminoester (1 g) and amyl nitrite (737 mg). The mixture was heated at 50° C. for 2 h. The resulting mixture was concentrated and purified by Biotage (5-10% ethyl acetate in hexane) to give the chloride as a brown solid.

To 4-iodopyrazole (715 mg) in 15 mL of THF was added NaH (161 mg, 60%) at 0° C. After 30 min, to this mixture was added the chloride intermediate (595 mg). After 30 min at 0° C., the mixture was warmed to RT and stirred for 8 h. The mixture was quenched with water and extracted with ethyl acetate. The organic layer contained some white solid which is pure biaryl product, and was collected by filtration. The filtrate was concentrated and further purified by Biotage (20-100% ethyl acetate in hexane) to give additional biaryl product as a white solid.

To this iodo intermediate (750 mg) in 30 mL of THF was dropwise added iPrMgCl (1.4 mL, 2 M in diethyl ether) at −78° C. under nitrogen to give a light brown solution. After 1 h at −78° C., to the resulting solution was added B(OMe)$_3$ (0.29 mL). The mixture was slowly warmed to 23° C. and stirred for 12 h. The mixture was partitioned between ethyl acetate and water. The organic layer was concentrated and treated with 10 mL of 30% hydrogen peroxide and 50 mL of THF. The mixture was heated at 50° C. for overnight. The mixture was then concentrated and purified by RP-HPLC to give the hydroxypyrazole.

To this alcohol intermediate (200 mg) was added 15 mL of dichloromethane, 0.15 mL of triethylamine and 148 mg of TBSCl. The crude mixture was concentrated and purified by Biotage (5-10% ethyl acetate in hexane) to give the silyl ether as an off-white solid.

To this methyl ester (265 mg) in 20 mL of dichloromethane was added DIBAL-H (5 mL, 1 M in hexane) at −78° C. The mixture was warmed to RT and stirred for 5 h before it was quenched with a saturated solution of Rochelle's salt. The slurry was stirred vigorously, and the aqueous layer was extracted with dichloromethane. The combined organic layers were dried with sodium sulfate and concentrated to give the hydroxymethylene product as a crude oil, which was directly used for the next step.

To this crude alcohol (300 mg) in 10 mL of dichloromethane was added sodium bicarbonate (121 mg) and Dess-Martin periodinane (490 mg). After 2 h, the crude mixture was purified by Biotage (10% ethyl acetate in hexane) to give the aldehyde.

To a solution of trimethyl phosphonate acetate (182 mg) in 20 mL of THF was added n-butyllithium (0.75 mL, 1.6 M in hexane) at 0° C. The resulting solution was stirred at this temperature for 30 min. To this solution was added a THF solution (5 mL) of the aldehyde intermediate (270 mg). The mixture was slowly warmed to RT and stirred for 2 hours. After quenching the mixture with water, the mixture was extracted with ethyl acetate, concentrated and purified by Biotage to give the methyl enoate as a white solid.

A mixture of methyl enoate (159 mg) and p-toluenesulfonyl hydrazide (2 g) in 30 mL of methanol was heated at 65° C. for 2.5 days. The solvent was removed, and the residue was purified by RP-HPLC to give the saturated methyl ester as a white solid.

To this methyl ester (40 mg) in 5 mL of THF:MeOH:water (3:1:1) was added LiOH (1.5 mL, 1 M). The mixture was stirred for 2 hours. After being acidified with concentrated HCl until pH=3, the slurry was extracted with 30% isopropanol in chloroform, dried with sodium sulfate and concentrated in vacuo to give the acid as an oily solid.

Following the similar amide formation and hydrolysis procedures described in the Examples above, Example 28 was obtained as a white solid. $^1$H NMR (Acetone-d$_6$, 500 MHz) δ 11.8 (1H, s), 7.84 (1H, s), 7.42 (1H, s), 727 (1H, s), 3.13 (2H, t), 2.95 (2H, t), 2.71 (2H, t), 2.34 (2H, m), 1.62 (4H, m); LCMS m/z 363 (M+1).

Example 29

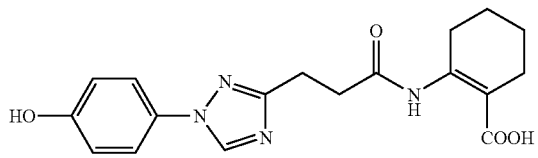

To a solution of 4-methoxyaniline (1.57 g) in 10% HCl (18 mL) was added sodium nitrite (0.87 g) in 4 mL of water at 0° C. After being stirred at 0° C. for 30 min, to this mixture was added dropwise, a solution of methyl isocyanoacetate (1.05 g) and sodium acetate (6.63 g) in methanol (40 mL) and water (12 mL) at 0° C. The mixture was stirred at 0° C. for 1.5 h. The solvent was removed in vacuo and the residue was extracted with ethyl acetate, washed with 5% HCl, saturated sodium bicarbonate solution and brine. The solution was then dried with sodium sulfate and purified by Biotage (40-80% ethyl acetate in hexane) to give the triazole intermediate.

To a solution of this triazole ester (0.7 g) in THF (40 mL) was added LiBH$_4$ (79 mg). The mixture was heated under reflux for 1 h and cooled to 23° C. The mixture was then quenched with 1 N HCl. After removing the solvent, the residue was dissolved in ethyl acetate, washed with saturated sodium bicarbonate solution, brine and dried with sodium sulfate. The concentration of this mixture gave the hydroxymethylene intermediate.

To this alcohol (0.46 g) was added 50 mL of dichloromethane and Dess-Martin reagent (227 mg) at 0° C. The mixture was warmed to RT and stirred for an additional 3 h. The mixture was purified by Biotage (40-80% ethyl acetate in hexane) to give the aldehyde.

To a solution of trimethyl phosphonoacetate (301 mg) in 20 mL of THF was added n-BuLi (0.73 mL, 2.5 M in hexane) at 0° C. After 30 min, to this solution was added the aldehyde intermediate (0.30 g). The resulting solution was stirred at RT for 1 h. To the solution was then added dichloromethane/water. The mixture was extracted with 30% isopropanol in chloroform. The organic layer was concentrated and purified by Biotage (40-80% ethyl acetate in hexane) to give the methyl enoate.

A mixture of the methyl enoate intermediate (186 mg), ca. 60 mg Pd/C (10%) and 200 mL of methanol/dichloromethane (1:1) was subjected to hydrogenation under a hydrogen balloon. After 20 min, the reaction mixture was filtered and the filtrate was concentrated to give the saturated methyl ester as a white solid.

Following the similar amide formation and hydrolysis procedures described in the Examples above, Example 29 was obtained as a white solid. $^1$H NMR (DMSO-d$_6$, 500 MHz) δ 12.5 (1H, bs), 11.7 (1H, s), 9.77 (1H, s), 7.57 (2H, d), 6.88 (2H, dd), 2.95 (2H, t), 2.82 (2H, m), 2.72 (2H, t), 2.23 (2H, m), 1.53 (4H, m); LCMS m/z 357 (M+1).

Example 30

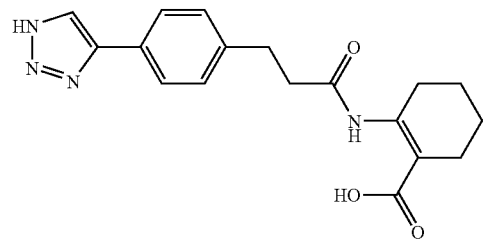

BuLi (10 mmol, 1.3 eq, 2.5M/THF, 4 mL) was added to a THF (8 mL) solution of trimethyl phosphonoacetate (9.23 mmol, 1.2 eq, 1.68 g) at −78° C. and stirred for 30 min. The solution was warmed to 0° C. for 10 min and re-cooled to −78° C. Then a THF (5 mL) solution of 4-ethynylbenzaldehyde (7.69 mmol, 1 eq, 1.00 g) was added dropwise and stirred for 2 h at RT. The reaction was partitioned between AcOEt and H$_2$O. The organic layer was dried, and the residue was recrystallized with CH$_2$Cl$_2$/MeOH to obtain a light yellow solid product.

A mixture of this methyl enoate acetylide (460 mg, 1 eq, 2.47 mmol), CuI (0.1 eq. 24 mg) and azidotrimethylsilane (427 mg, 1.5 eq, 3.71 mmol) were mixed in DMF/MeOH (5 mL, 9/1) in a sealed tube and heated to 100° C. for 15 h. The reaction solution was cooled to RT and diluted with AcOEt (10 mL). The solution was filtered through celite and dried under reduced pressure. The residue was recrystallized with CH$_2$Cl$_2$/MeOH to obtain a light yellow solid product triazole.

Then LiOH (0.5 M, 8 mL) was added to this methyl ester (450 mg, 1.97 mmol) in MeOH/THF (10 mL, 1/9) and stirred until all solids were dissolved (about 2 h). Then 20 mL of MeOH was added to this solution, followed by Pd/C (10 mg), and the mixture was subjected to hydrogenation under balloon pressure for 15 h. The reaction solution was filtered and acidified to pH=7. The product white solid was obtained by filtration of the precipitate.

Following the similar amide formation and hydrolysis procedures described in the Examples above, Example 30 was obtained. $^1$H NMR (CD$_3$OD, 500 MHz) δ 8.12 (s, 1H), 7.75 (d, 2H), 7.33 (d, 2H), 3.00 (t, 2H), 2.89 (t, 2H), 2.65 (t, 2H), 2.32 (t, 2H), 1.62 (m, 4H); LCMS m/z 339 (M−1).

Example 31

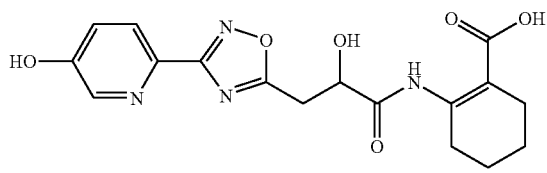

To racemic malic acid (1.03 g) was added 2,2-dimethoxypropane (25 mL) and p-TsOH hydrate (30 mg). The mixture was stirred overnight before the addition of sodium acetate. The mixture was stirred for additional 3 h and filtered. The filtrate was concentrated, and the mono-protected acid was crystallized from chloroform/hexane as a white solid.

To a solution of this acid intermediate (281 mg) in 10 mL of dichloromethane was added CDI (524 mg). The resulting mixture was stirred for 1 h, and to this mixture was added the N-hydroxy amidine (1.32 g) and dichloromethane (10 mL). The mixture was stirred over 2 days and then filtered. The filtrate was concentrated, and the residue was suspended in toluene (40 mL) and heated to 120° C. for 6 h and 130° C. for 2 h. After removing the solvent, the residue was purified by Biotage (20-40% ethyl acetate in hexane) to give the oxadiazole intermediate, which was dissolved in chloroform (5 mL) and treated with TFA (2.5 mL) for 20 min. The mixture was concentrated, and to the residue was added 5% KOH in ethanol (50 ml). The resulting mixture was stirred for 6 h and acidified with HCl until pH=4. The solution was extracted with 30% isopropanol in chloroform. The extracts were concentrated and purified by RP-HPLC to give the hydroxypyridyl alpha-hydroxy acid intermediate. Following similar procedures as described for the Examples above, Example 31 was obtained after silylation, amide formation and hydrolysis. $^1$H NMR (CD$_3$OD, 500 MHz) δ 8.25 (1H, s), 8.06 (1H, dd), 7.42 (1H, dd), 4.63 (1H, dd), 3.62 (1H, m), 3.52 (1H, m), 2.92 (1H, m), 2.35 (1H, m), 1.63 (6H, m); LCMS m/z 375 (M+1).

Example 32

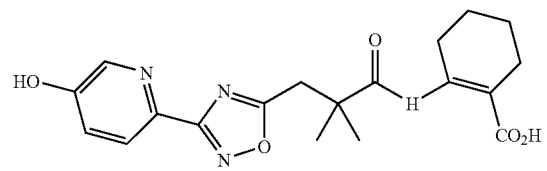

A solution of the commercially available olefinic acid shown in Scheme 21 (20 g) in ethanol (150 mL) in the presence of 0.5 mL of concentrated sulfuric acid, was heated under reflux for 1 day. A pad of 3A molecular sieves above the reaction flask was used to absorb the water generated from the reaction. The mixture containing the volatile ester was cooled to 0° C., and to the mixture was added NMO (21.9 g) and 4% of OsO$_4$ (1 mL). The solution was stirred at 0° C. for 1 h and then warmed to 23° C. and stirred overnight. Most of the solvent in this mixture was removed in vacuo, the residue was partitioned between water and ethyl acetate. The organic layer was concentrated to give the diol intermediate as a brown oil.

To a solution of this diol in 300 mL of acetone at 0° C. was added a slurry of sodium periodate (87 g) in 400 mL of water. The resulting white slurry was slowly warmed to RT and stirred for 1.5 h. The slurry was filtered and washed with acetone, and the filtrate was extracted with dichloromethane. The combined organic layers were carefully concentrated to provide the volatile aldehyde as a brown oil. At 0° C., to the solution of this aldehyde and tert-butanol (150 mL) was added 2-methyl-2-butene (20 mL) and a solution of sodium dihydrophosphate (15 g) and sodium chlorite (41 g, ~80%). The resulting brown mixture was slowly warmed to RT, and the mixture was stirred for 5 h. To the mixture was added 10% sodium hydroxide until pH>11. The mixture was then washed with ethyl acetate, and the aqueous layer was acidified with concentrated HCl until pH=4. The resulting aqueous fraction was extracted with ethyl acetate. The combined organic fractions were dried with sodium sulfate and concentrated in vacuo to give the mono-acid mono-ester as a colorless oil.

To a solution of this acid intermediate (13.5 g) in 120 mL of dichloromethane were added 50 μL of DMF and 97 mL of oxalyl chloride (2 M in dichloromethane) at 0° C. The mixture was stirred at 0° C. for 30 min, warmed to 23° C., and the resulting solution was stirred for an additional 2 h. After removing the volatiles, to the residue was added the N-hydroxy amidine (21.2 g) and 100 mL of pyridine. The mixture was then heated at 130° C. for overnight. The pyridine was removed in vacuo, and the residue was partitioned between water and dichloromethane. The organic phase was concentrated and purified by Biotage (eluting with 10-40% ethyl acetate in hexane) to give the bi-heterocyclic intermediate as a white solid.

To this ester (15.1 g) in 400 mL of THF/MeOH/water (3:1:1), was added LiOH (200 mL, 1 N) dropwise. The mixture was stirred at room temperature for 2 h. After removing most organic solvent in vacuo, the aqueous layer was acidified with 1 N HCl to pH=3. The precipitate was extracted with dichloromethane thrice. The combined organic phase was dried with sodium sulfate and concentrated to give the acid as a white solid.

To a solution of this acid intermediate (14.3 g) in 300 mL of dichloromethane, were added N-hydroxysuccinimide (4.52 g) and EDCI (7.53 g). The mixture was stirred for 2.5 h and then diluted to 1 L of dichloromethane. The resulting solution was washed with brine and dried with sodium sulfate. The solution was concentrated, and the resulting residue was dissolved in 700 mL of dioxane. To this solution was added ammonia in water (60 mL, 28-30%) at 0° C. The resulting mixture was stirred at RT for 15 min. The volatiles were removed in vacuo, and the residue was partitioned between water and dichloromethane. The organic phase was washed with water, saturated sodium bicarbonate, and then dried with sodium sulfate. The resulting solution was concentrated to give the primary carboxamide as a white solid.

A mixture of this carboxamide (6.83 g), the enol triflate (12.9 g), Pd$_2$(dba)$_3$ (1.31 g), Cs$_2$CO$_3$ (9.9 g, anhydrous), Xantphos (2.48 g) and 200 mL of dioxane was heated under argon at 80° C. for overnight. The mixture was cooled and filtered through celite, concentrated, and purified by Biotage (20-40% ethyl acetate in hexane) to give the cyclohexenylamide ester as an oil.

To this ester (8.6 g) in 84 mL of dichloromethane was added triisopropylsilane (8.4 mL) and TFA (40 mL) at 0° C. The mixture was stirred at room temperature for 15 min, the solvents removed, the residue dissolved in 200 mL of THF/MeOH/water (3:1:1), and the mixture treated dropwise with excess of LiOH (1 N). The mixture was stirred at RT overnight, and after removing most organic solvents in vacuo, the aqueous layer was washed with ethyl acetate. The aqueous layer was then acidified with 1N HCl to pH=5. The precipitate was collected by filtration, washed with water and diethyl ether to give the product as a crude material. This material was dissolved in 30% isopropanol in chloroform and filtered. The filtrate was concentrated to a small volume and the homogeneous mixture was kept at 0° C. overnight. The precipitate was collected, washed with methanol, then diethyl ether and dried under vacuum to provide Example 32 as a white solid. $^1$H NMR (Acetone-d6, 500 MHz) δ 12.1 (1H, s), 8.36 (1H, s), 7.98 (1H, d), 7.41 (1H, d), 3.27 (2H, s), 2.95 (2H, m), 2.37 (2H, m), 1.63 (4H, m), 1.46 (6H, s); LCMS m/z 387 (M+1).

Example 33

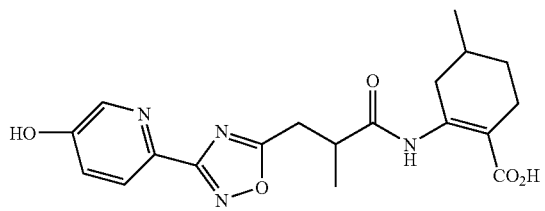

To (S)-pulegone (4 g) was added concentrated HCl (3.8 mL) and 12 mL of water. The mixture was heated at reflux for 20 h under vigorous stirring. The mixture was distilled to remove acetone and the heating oil was heated at 180° C. to distill off both organic layer and HCl (aq). The organic layer was separated from the aqueous layer and then was diluted with diethyl ether and washed with sodium bicarbonate solution. The organic layer was then dried with sodium sulfate and concentrated carefully to remove most of the diethyl ether to give the (S)-3-methylcyclohexanone.

To this (S)-3-methylcyclohexanone (2 g) in 50 mL of UV, was added LiHMDS (20 mL, 1 M in THF) at −78° C. The mixture was slowly warmed to 0° C. and stirred for 30 min before the solution was re-cooled to −78° C. To this mixture was added methyl cyanoformate (1.55 mL), and the mixture was stirred at −20° C. for 2 h before the addition of 1 N HCl solution. The aqueous layer was extracted with diethyl ether and purified by Biotage (10-20% diethyl ether in hexane) to give the ketoester as a colorless oil.

To this ketoester intermediate (1 g) in 20 mL of methanol, was added ammonium acetate (4.6 g), and the mixture was stirred overnight. After the removal of the solvent, the residue was diluted with ethyl acetate. The solid was filtered off, and the filtrate was washed with water, brine and dried with sodium sulfate. The liquid was then concentrated to give the (S)-cyclohexene aminoester as an oily solid.

The enantiomeric ester intermediates from Example 27 above (200 mg) were each heated at 70° C. in 1 mL of concentrated HCl/HOAc (v:v=1:2) for 30 min. The resulting mixture was concentrated under high vacuum overnight. The enantiomeric acids were then submitted directly for the next amidation step with the (S)-cyclohexene aminoester as described in the Examples above.

Following the similar hydrolysis procedures as described in the Examples above, provided two of the four possible diastereomers of Example 33 containing minor epimerization. (S)-Diastereomer A: $^1$H NMR (DMSO-d$_6$, 500 MHz) δ 12.6 (1H, s), 11.7 (1H, s), 10.6 (1H, s), 8.26 (1H, s), 7.88 (1H, d), 7.30 (1H, d), 3.02 (4H, m), 2.33 (2H, m), 2.16 (1H, m), 1.60 (2H, m), 1.27 (3H, s), 1.09 (1H, m), 0.91 (3H, d); LCMS m/z 387 (M+1). (S)-Diastereomer B: $^1$H NMR (DMSO-d$_6$, 500 MHz) δ 12.6 (1H, s), 11.69 (1H, s), 10.6 (1H, s), 8.26 (1H, s), 7.88 (1H, d), 7.30 (1H, d), 3.02 (4H, m), 2.33 (2H, m), 2.16 (1H, m), 1.60 (2H, m), 1.27 (3H, s), 1.09 (1H, m), 0.91 (3H, d); LCMS m/z 387 (M+1).

Utilizing the commercially available (R)-3-methylcyclohexanone, provided access to the additional other two diastereomers of Example 33. Thus to a suspension of sodium hydride (3.57 g, 89.15 mmol, 60% dispersion in oil) in anhydrous dioxane (25 mL) was added dimethyl carbonate (30 mL, 356.6 mmol). The resulting mixture was heated to 85° C., and a solution of (R)-3-methylcyclohexanone (5.0 g, 44.64 mmol) in dioxane (50 mL) was added dropwise via an addition funnel. After stirring at 80° C. for 2 hours, the reaction mixture was cooled to room temperature and quenched with 1N HCl. The resulting mixture was concentrated, the residue was extracted with ether, and the organic layer was washed with brine, dried over magnesium sulfate, filtered and concentrated. The residue was purified by Biotage using a gradient of 0-5% ethyl acetate-hexanes to give the desired product as a white crystalline solid.

To a solution of this methyl ketoester intermediate (2.5 g, 14.7 mmol) in methanol (50 mL) was added ammonium acetate (5.66 g, 73.52 mmol). The reaction mixture was left stirring at RT for 16 h. It was then concentrated, and the residue was diluted with ethyl acetate and washed with water. The organic layer was washed with brine, dried over anhydrous sodium sulfate, filtered and concentrated. A white solid was obtained for this methyl (R)-cyclohexene aminoester intermediate.

As before, the enantiomeric ester intermediates from Example 27 above were each converted to their respective acids. One enantiomeric acid was then submitted directly for the next amidation step with the methyl (R)-cyclohexene aminoester as described in the Examples above. Following the similar hydrolysis procedures as described in the Examples above, and subsequent purification by reverse phase HPLC, provided the third diastereomer of Example 33 containing minor epimerization. (R)-Diastereomer A: $^1$H NMR (500 MHz, DMSO-d$_6$) δ 11.73 (s, 1H), 8.26 (s, 1H), 7.9 (d, 1H), 7.37 (dd, 1H), 3.26 (m, 1H), 3.0 (m, 3H), 2.4 (m, 2H), 2.1 (m, 1H), 1.6 (m, 2H), 1.28 (d, 3H), 1.08 (m, 1H), 0.93 (d, 3H); LCMS m/z 387 (M+1).

To obtain the fourth diastereomer of Example 33, a solution of the (R)-3-methyl cyclohexanone (2.18 g, 19.46 mmol) in anhydrous THF (50 mL), cooled to −78° C., was treated with LiHMDS (23.35 mL, 1.0 M in THF). After 15 minutes, benzyl cyanoformate was added. The reaction mixture was slowly warmed to 0° C. over an hour, and quenched by the addition of 1N HCl. The resulting mixture was extracted with ethyl acetate. The organic layer was washed with brine, dried over anhydrous sodium sulfate, filtered and concentrated. The residue was purified by Biotage SP-I using a gradient of 0-15% ethyl acetate-hexanes to give the desired product as a colorless oil.

To a solution of this benzyl ketoester intermediate (1.0 g, 4.06 mmol) in methanol (20 mL) was added ammonium acetate (1.57 g, 20.32 mmol). After stirring the reaction at 23° C. for 16 hours it was concentrated. The residue was diluted with ethyl acetate and washed with water. The organic layer was washed with brine, dried over anhydrous sodium sulfate, filtered and concentrated. A white solid was obtained for this benzyl (R)-cyclohexene aminoester intermediate.

As before, the enantiomeric ester intermediates from Example 27 above were each converted to their respective acids. One enantiomeric acid was then submitted directly for the next amidation step with the benzyl (R)-cyclohexene aminoester as described in the Examples above. Following the similar PMB-ether deprotection procedures as described in the Examples above, provided the benzyl ester penultimate intermediate.

To a solution of this benzyl ester intermediate (27 mg, 0.056 mmol) in methanol (2 mL) was added Pd/C (10 mg). The resulting solution was stirred under a hydrogen balloon for 15 minutes. The reaction mixture was filtered through celite. The filtrate was concentrated and purified by reverse phase HPLC to provide the fourth diastereomer of Example 33 containing minor epimerization. (R)-Diastereomer B: $^1$H NMR (500 MHz, DMSO-$d_6$) δ 11.69 (s, 1H), 8.26 (s, 1H), 7.88 (d, 1H), 7.3 (dd, 1H), 3.24 (m, 1H), 3.0 (m, 3H), 2.4 (m, 2H), 2.1 (m, 1H), 1.6 (m, 2H), 1.26 (d, 3H), 1.1 (m, 1H), 0.92 (d, 3H); LCMS m/z 387 (M+1).

Example 34

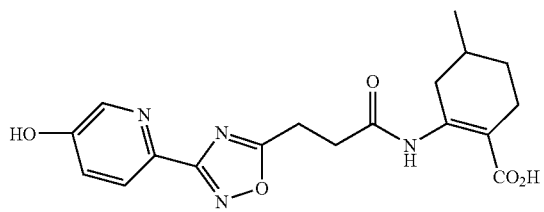

The enantiomers of Example 34 were generated from the respective methyl (R)-cyclohexene aminoester and methyl (S)-cyclohexene aminoester intermediates prepared in Example 33 above. These enantiomeric methyl cyclohexene aminoesters were acylated with the requisite carboxylic acid intermediate from Example 23, and the amides converted to the desired products following the procedures described in the Examples above. (S)-Enantiomer: $^1$H NMR. (CD$_3$OD, 500 MHz) δ 8.23 (1H, s), 8.01 (1H, d), 7.34 (1H, d), 3.29 (2H, m), 3.08 (1H, bd), 2.99 (2H, bs), 2.50 (1H, bd), 2.41 (1H, m), 2.28 (1H, m), 1.70 (1H, m), 1.66 (1H, m), 1.18 (1H, m), 1.01 (3H, d); LCMS m/z 373 (M+1). (R)-Enantiomer: $^1$H NMR (500 MHz, DMSO-$d_6$) δ 11.66 (s, 1H), 8.26 (s, 1H), 7.91 (d, 1H), 7.32 (dd, 1H), 3.2 (t, 2H), 3.0 (dd, 1H), 2.9 (m, 2H), 2.4 (m, 2H), 2.1 (m, 1H), 1.6 (m, 2H), 1.15 (m, 1H), 0.95 (d, 3H); LCMS m/z 373 (M+1).

Example 35

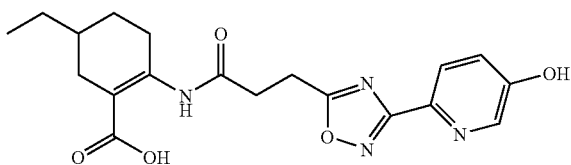

Commercially available 4-ethylcyclohexanone was converted to its methyl ketoester via Mander's reagent under the conditions described in the Examples above. This material as an orange oil was used in the next step without any further purification.

To a solution of this methyl ketoester intermediate (475 mg, 2.6 mmol) in anhydrous THF (25 mL) cooled to 0° C., was added NaH (113 mg, 2.84 mmol, 60%). After 30 min, 2-[N,N-bis(trifluoromethylsulfonyl)amino]-5-chloropyridine (1.13 g, 2.84 mmol) was added, and the resulting reaction stirred at room temperature for 2 h. The reaction mixture was quenched with 1N HCl, then extracted with EtOAc. The organic layers were washed with brine, dried over Na$_2$SO$_4$, filtered and concentrated to give a brown oil. This material was purified by Biotage using 50% EtOAc/hexanes as eluant to give the desired enol triflate intermediate.

As shown in Scheme 23, the methyl ester intermediate from Example 23 can be directly converted to its primary carboxamide. Thus to a solution of this methyl ester in dioxane in a pressure tube was added 7N ammonia in methanol. The resulting solution was heated at 70° C. for 16 hours. The reaction mixture was cooled to room temperature and concentrated to give the desired primary carboxamide intermediate as a white solid.

To a solution of the enol triflate intermediate (150 mg, 0.37 9 mmol) in anhydrous dioxane (3 mL) was added the primary carboxamide intermediate (112 mg, 0.316 mmol), XANTPHOS (37 mg, 0.06 mmol), cesium carbonate (46 mg, 0.36 mmol) and Pd$_2$(dba)$_3$ (20 mg, 0.019 mmol). The resulting mixture was de-gassed for 2 minutes by bubbling N$_2$. The reaction was heated at 60° C. under a N$_2$ atmosphere for 18 h. The reaction mixture was cooled to RT, and filtered through celite. The filtrate was concentrated, and the residue was purified by Prep-TLC (30% ethyl acetate-hexanes) to give the desired amide product.

To a solution of this intermediate (89 mg, 0.171 mmol) in DCM (2 mL) was added triisopropyl silane (0.3 mL) followed by TFA (1 mL). After stirring the mixture for 20 min, it was cooled to 0° C. and carefully quenched by the addition of saturated sodium bicarbonate solution. The resulting mixture was extracted with 30% isopropanol/chloroform. The organic layer was dried over anhydrous sodium sulfate, filtered and concentrated. This material was dissolved in THF (5 mL), 1N NaOH (2 mL) was added followed by enough MeOH to obtain a homogenous solution. After stirring the reaction at room temperature for 18 h, it was neutralized with 1N HCl. The resulting mixture was extracted with 20% isopropanol/chloroform. The organic layer was washed with brine and dried over Na$_2$SO$_4$, filtered and concentrated. The residue was purified by reverse phase HPLC (10-100% acetonitrile/H$_2$O (1% TFA)) to provide Example 35. $^1$H NMR (CD$_3$OD, 500 MHz), δ 8.25 (d, 1H), 7.90-7.88 (d, 1H) 7.31-7.29 (dd, 1H), 3.18 (t, 2H), 2.99-2.88 (m, 3H), 2.69-2.63 (m, 1H), 2.44-2.40 (m, 1H), 1.78-1.73 (m, 2H), 1.30-1.23 (m, 3H), 1.10-1.06 (m, 1H), 0.866 (t, 3H); LCMS m/z 387 (M+1).

Example 36

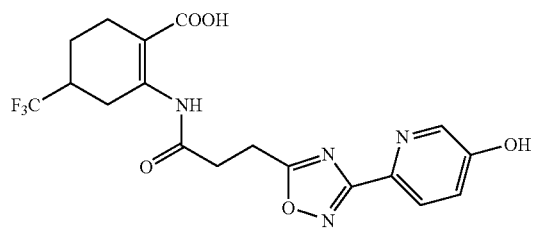

To a solution of 3-(trifluoromethyl)-phenol (3.0 g, 18.51 mmol) in methanol (20 mL) was added Rh/Al₂O₃ (100 mg). The resulting mixture was stirred under hydrogen atmosphere (50 psi) for 16 h. The reaction was filtered through celite and concentrated to give the cyclohexanol as a colorless oil.

To a solution of this cyclohexanol intermediate (3.0 g, 17.85 mmol) in dichloromethane (100 mL) was added Dess-Martin reagent (9.0 g, 21.42 mmol). After stirring at room temperature for 4 h, the mixture was quenched with saturated sodium bicarbonate solution. The resulting mixture was extracted with dichloromethane. The organic layer was dried over anhydrous sodium sulfate, filtered and concentrated to give the ketone as a colorless oil.

To a solution of this cyclohexanone intermediate (2.0 g, 12.04 mmol) in anhydrous THF cooled to −78° C. was added LiHMDS (14.5 mL, 14.5 mmol, 1.0 M in THY). The resulting mixture was warmed to 0° C. and stirred for 20 min. The reaction mixture was cooled back to −78° C. and methyl cyanoformate (1.15 mL, 14.46 mmol) was added. The reaction mixture was warmed to −20° C. and quenched with 1N HCl. The resulting mixture was extracted with ethyl acetate. The organic layer was washed with brine, dried over anhydrous sodium sulfate, filtered and concentrated. The residue was purified by flash chromatography using 10% ethyl acetate-hexanes to give the ketoester as a colorless oil.

To this ketoester intermediate (860 mg, 3.83 mmol) in methanol was added ammonium acetate (1.48 g, 19.2 mmol). After stirring the mixture at room temperature for 16 h, it was concentrated. The residue was diluted with ethyl acetate and washed with water. The organic layer was washed with brine, dried over anhydrous sodium sulfate, filtered and concentrated. A white solid of the trifluorocyclohexene aminoester was obtained.

As shown in Scheme 24, the carboxylic acid intermediate from Example 23 can be used to acylate this trifluorocyclohexene aminoester. Thus to a solution of the carboxylic acid (100 mg, 0.281 mmol) in anhydrous dichloromethane (5 mL) cooled to 0° C. under nitrogen atmosphere, was added DMF (10 μL) followed by oxalyl chloride (0.562 mL, 2.0 M solution in DCM). The reaction mixture was warmed to 23° C. and stirred for 30 min. The reaction mixture was concentrated, and the residue was dissolved in anhydrous dichloromethane. A solution of the trifluorocyclohexene aminoester (140 mg, 0.627 mmol) in dichloromethane (2 mL) was added. After stirring the mixture at RT for 16 h, it was quenched by the addition of saturated sodium bicarbonate solution. The resulting mixture was extracted with dichloromethane. The organic layer was dried over anhydrous sodium sulfate, filtered and concentrated. The residue was purified by flash chromatography using 40% ethyl acetate-hexanes to give the desired amide methyl ester as a white solid.

To a solution of this ester intermediate (44 mg) in THF (2 mL) was added 0.5 N NaOH (2 mL), followed by MeOH (1 mL). After stirring the mixture for 1 h, it was quenched by neutralizing with 1N HCl (1 mL). The resulting mixture was concentrated, and the residue was diluted with water (5 mL) and extracted with ethyl acetate. The organic layer was dried over anhydrous sodium sulfate, filtered and concentrated. The residue was purified by reverse phase HPLC to provide Example 36. ¹H NMR (500 MHz, DMSO-d₆) δ 11.64 (s, 1H), 10.62 (bs, 1H), 8.26 (bs, 1H), 7.9 (d, 1H), 7.32 (dd, 1H), 3.2 (m, 3H), 2.9 (m, 2H), 2.75 (m, 1H), 2.6 (m, 2H), 2.2 (m, 1H), 1.9 (m, 1H), 1.4 (m, 1H); LCMS m/z 427 (M+1).

Example 37

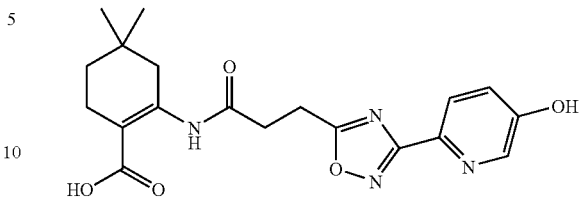

To a suspension of copper(I) iodide (3.8 g, 20 mmol) in anhydrous ether (20 mL) cooled to 0° C. under a nitrogen atmosphere was added dropwise a solution of methyl lithium (25 mL, 40 mmol, 1.6 M in diethylether). After stirring the mixture at 0° C. for 20 min, it was cooled to −78° C. and 3-methyl 2-cyclohexen-1-one was added. The reaction mixture was slowly warmed to −20° C. over 1 h and quenched by the addition of conc. ammonium hydroxide solution (10 mL). The resulting biphasic solution was stirred for 20 rain. The aqueous layer was extracted with ether, and the organic layer was washed with brine, dried over anhydrous sodium sulfate, filtered and concentrated. The residue was purified by flash chromatography using 10% ethyl acetate-hexanes to give the desired geminal dimethyl cyclohexanone as a yellow oil.

To a solution of this cyclohexanone intermediate (740 mg, 5.86 mmol) in anhydrous THF (20 mL) cooled to −78° C. under a nitrogen atmosphere, was added LiHMDS (7 mL, 7 mmol, 1.0 M solution). After 15 min, methyl cyanoformate (0.558 mL, 7.03 mmol) was added. After stirring the mixture at −78° C. for 20 min, it was quenched with 1N HCl. The biphasic mixture was extracted with ethyl acetate, washed with brine and dried over anhydrous sodium sulfate. The organic layer was filtered, concentrated and purified by flash chromatography using 10% ethyl acetate hexanes to give the ketoester as a colorless oil.

To a solution of this ketoester intermediate (500 mg, 2.72 mmol) in methanol (30 mL) was added ammonium acetate (1.05 g, 13.6 mmol). After stirring the reaction mixture at room temperature for 48 h, it was concentrated, and the residue was diluted with ethyl acetate and washed with water. The organic layer was washed with brine, dried over anhydrous sodium sulfate, filtered and concentrated. A white solid was obtained for the geminal dimethyl cyclohexene aminoester intermediate.

As shown in Scheme 25, the carboxylic acid intermediate from Example 23 can be used to acylate this cyclohexene aminoester. Thus to a solution of the carboxylic acid (100 mg, 0.281 mmol) in methylene chloride (4 mL) and DMF (20 uL), was added oxalyl chloride (0.281 mL, 0.563 mmol) at 0° C. The solution was stirred at RT for 30 min, then concentrated. To the resulting residue was added methylene chloride (3 mL) followed by a solution of the cyclohexene aminoester intermediate (129 mg, 0.703 mmol) in methylene chloride (2 mL). The reaction was stirred at 23° C. under N₂ for 3 h, then quenched with saturated NaHCO₃ solution and extracted with methylene chloride. The combined organic layers were dried over anhydrous sodium sulfate, filtered and concentrated. The residue was purified on silica, eluting with a gradient of 20%-60% EtOAc/hexanes over 10 column volumes, then 60%-100% EtOAc/hexanes over 4 column volumes, affording the desired amide as a white solid.

To a solution of this PMB ether intermediate (84 mg, 0.161 mmol) in methylene chloride (4 mL) was added triisopropylsilane (500 uL, 2.441 mmol) then TFA (2 ml, 26.0 mmol). The reaction was stirred for 5 min, then slowly quenched at 0° C. with saturated aqueous $NaHCO_3$ in an ice bath. This mixture was extracted with methylene chloride then 30% $IPA/CHCl_3$. The combined organic layers were dried over anhydrous sodium sulfate, filtered and concentrated. The solid residue was used in the next step without further purification.

To this ester intermediate was added THF (2 mL), NaOH (2 mL, 1.0 mmol) and methanol (1 mL). The mixture was stirred overnight, then quenched with 1N HCl (1 mL) and concentrated. The mixture was diluted with water and extracted with EtOAc. The combined organic layers were dried over anhydrous sodium sulfate, filtered and concentrated to an oily residue. The residue was purified by reverse phase HPLC to provide Example 37. $^1H$ NMR (500 MHz, DMSO-$d_6$) δ 11.67 (s, 1H), 8.26 (d, 1H), 7.89 (d, 1H), 7.30 (dd, 1H), 3.18 (t, 2H), 2.90 (t, 2H), 2.59 (s, 2H), 2.25 (t, 2H), 1.29 (t, 2H), 0.87 (s, 6H); LCMS m/z 369 (M–17).

Example 38

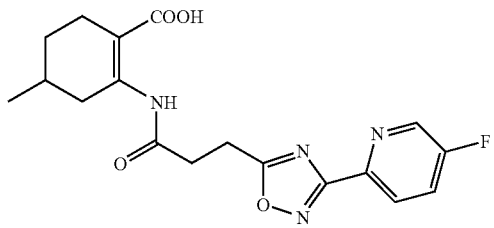

To a suspension of 5-amino-2-cyano pyridine (20.0 g, 0.168 mol) in HF-pyridine (100 g) in an Erlenmeyer flask cooled to 0° C. was added sodium nitrite (17.4 g, 0.251 mol) in four portions. After 45 min at 0° C. the reaction mixture was stirred at room temperature for 30 min and then heated to 80° C. for 90 min. The reaction mixture was quenched by pouring into ice/water mixture. The resulting mixture was extracted with DCM. The organic layer was dried over anhydrous sodium sulfate, filtered and concentrated to give the fluoropyridine as an orange solid.

To a suspension of this fluoropyridine nitrile intermediate (16.0 g, 0.131 mol) in methanol (200 mL) was added hydroxylamine (9.63 mL, 0.157 mmol, 50% by wt). After stirring the reaction at room temperature for 48 h, it was filtered through a fritted funnel. The precipitate was washed with ether and dried under vacuum to give the N-hydroxy amidine as a yellow solid.

To a suspension of this amidine intermediate (5.32 g, 34.32 mmol) in anhydrous pyridine (10 mL) was added 4-chloro-4-oxo-methyl butyrate (5 mL, 41.18 mmol). The resulting reaction mixture was heated at 120° C. for 2 h. The mixture was cooled to RT and concentrated. The residue was dissolved in ethyl acetate and washed with 1N HCl, water and brine. The organic layer was dried over anhydrous sodium sulfate, filtered and concentrated to give a dark brown solid. This material was purified by Biotage using 25%-60% ethyl acetate-hexanes gradient to give the heterobiaryl intermediate as a light yellow solid.

To a solution of this ester intermediate (900 mg, 3.58 mmol) in TIM (4 mL) was added methanol (2 mL) followed by 5N NaOH (1 mL). After 30 min, the reaction mixture was neutralized by the addition of 1N HCl (5 mL). The reaction mixture was concentrated. The residue was extracted with ethyl acetate, and the organic layer was washed with brine,
dried over anhydrous sodium sulfate, filtered and concentrated to give a light yellow solid of the carboxylic acid.

To a solution of this acid intermediate (50 mg, 0.21 mmol) in anhydrous dichloromethane (4 mL) cooled to 0° C. under nitrogen atmosphere was added DMF (10 μL) followed by oxalyl chloride (0.21 mL, 2.0 M solution in DCM). The reaction was warmed to 23° C. and stirred for 30 min. The reaction mixture was concentrated, and the residue was dissolved in anhydrous dichloromethane (2 mL) and cooled to 0° C. A dichloromethane (2 mL) solution of the methyl (R)-cyclohexene aminoester described in the Examples above (90 mg, 0.525 mmol) was then added. The ice-bath was removed, and the resulting solution was stirred at RT for 16 h. The reaction mixture was quenched by the addition of saturated sodium bicarbonate solution. The resulting mixture was extracted with dichloromethane. The organic layer was dried over anhydrous sodium sulfate, filtered and concentrated. The residue was purified by flash chromatography using 25% then 35% ethyl acetate-hexanes to give the amide as a white solid.

To a solution of this amide ester intermediate (41 mg) in THF was added 1N LiOH (1 mL). The resulting mixture was stirred for 16 h. The reaction mixture was neutralized by the addition of 1N HCl (1 mL). The resulting biphasic mixture was extracted with ethyl acetate. The organic layer was dried over anhydrous sodium sulfate, filtered and concentrated. The residue was purified by reverse phase HPLC to provide Example 38 as the (R)-enantiomer. $^1H$ NMR. (500 MHz, DMSO-$d_6$) δ 12.6 (bs, 1H), 11.64 (s, 1H), 8.76 (d, 1H), 8.14 (dd, 1H), 7.93 (dt, 1H), 3.2 (t, 2H), 2.9 (m, 3H), 2.3 (m, 2H), 2.15 (m, 1H), 1.6 (m, 2H), 1.1 (m, 1H), 0.92 (d, 3H); LCMS m/z 397 (M+Na).

Example 39

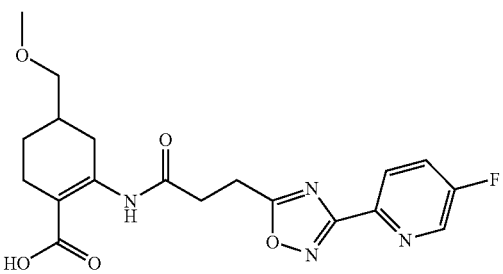

To a solution of 3-hydroxy benzaldehyde (1.2 g, 10 mmol) in anhydrous DCM (50 mL) was added imidazole (1.02 g, 15 mmol) followed by TBSCl (1.65 g, 11 mmol). After stirring the reaction at room temperature for 1 h, it was quenched by pouring into saturated sodium bicarbonate solution. The resulting mixture was extracted with DCM, and the organic layer was dried over anhydrous sodium sulfate, filtered and concentrated to give the silyl ether aldehyde.

To a solution of this aldehyde intermediate (2.24 g, 9.5 mmol) in ethanol (50 mL) was added sodium borohydride (0.5 g, 14.5 mmol). After stirring the mixture at RT for 1 h, it was concentrated, and the residue was dissolved in ethyl acetate and washed with water and brine. The organic layer was dried over anhydrous sodium sulfate, filtered and concentrated to give the hydroxy methylene intermediate.

To a solution of this alcohol (2.25 g, 9.5 mmol) in anhydrous THF (50 mL) cooled to 0° C. under a nitrogen atmosphere was added sodium hydride (0.57 g, 14.25 mmol). After 15 min, methyl iodide (0.89 mL, 14.25 mmol) was added. After stirring the mixture at room temperature for 1 h, it was quenched with saturated ammonium chloride solution. The resulting mixture was extracted with ethyl acetate, washed with brine, dried over anhydrous sodium sulfate, filtered and concentrated. The crude material was dissolved in THF (20 mL) and TBAF (2 mL) was added. After 1 h, the reaction mixture was concentrated and the residue purified by flash chromatography using 30% ethyl acetate hexanes to give the methyl ether as a colorless oil.

To a solution of this phenol intermediate (0.9 g, 6.52 mmol) in methanol (20 mL) was added Rh/Al$_2$O$_3$ (50 mg). The resulting mixture was stirred under a hydrogen balloon for 18 h. The mixture was filtered through celite and concentrated to give the desired cyclohexanol as a colorless oil.

To a solution of this cyclohexanol (870 mg, 6 mmol) in DCM cooled to −78° C. was added DMSO (0.85 ml, 12 mmol) followed by oxalyl chloride (4.5 mL, 2M in DCM). After 10 min, triethylamine (1.67 mL, 12 mmol) was added and the reaction mixture slowly warmed to 0° C. over 1 h. The mixture was quenched by pouring into saturated sodium bicarbonate solution. The resulting mixture was extracted with DCM. The organic layer was dried over anhydrous sodium sulfate, filtered and concentrated. The residue was purified by flash chromatography using 10% ethyl acetate-hexanes to give the cyclohexanone intermediate.

To a suspension of sodium hydride (0.225 g, 5.62 mmol, 60% dispersion in oil) in anhydrous dioxane (5 mL) was added dimethyl carbonate (1 mL, 11.87 mmol). The resulting mixture was heated to 85° C., and a solution the cyclohexanone intermediate (400 mg, 2.81 mmol) in dioxane (5 mL) was added dropwise via an addition funnel. After stirring at 80° C. for 2 h, the reaction mixture was cooled to room temperature and quenched with 1N HCl. The resulting mixture was concentrated. The residue was extracted with ether. The organic layer was washed with brine, dried over magnesium sulfate, filtered and concentrated. The residue was purified by flash chromatography 30% ethyl acetate-hexanes to give the ketoester.

To a solution of this ketoester (199 mg, 0.994 mmol) in methanol (12 mL), was added ammonium acetate (383 mg, 4.97 mmol). The reaction was left stirring at room temperature, and concentrated. The residue was dissolved in EtOAc and washed with water and brine. The organic phase was dried over anhydrous sodium sulfate, filtered and concentrated to give the methoxymethyl ether substituted cyclohexene aminoester.

Following similar procedures as described for the Examples above, Example 39 was obtained after amide formation and hydrolysis. The residue was purified by reverse phase HPLC to provide Example 39. $^1$H NMR. (500 MHz, DMSO-d$_6$) δ 11.66 (s, 1H), 8.76 (d, 1H), 8.14 (dd, 1H), 7.94 (m, 1), 3.24-3.20 (m, 7H), 3.01-2.89 (m, 3H), 2.43 (t, 1H), 2.37 (d, 1H), 2.16 (m, 1H), 1.75 (m, 1H), 1.68 (br d, 1H), 1.14 (m, 1H); LCMS m/z 403 (M−1).

Example 40

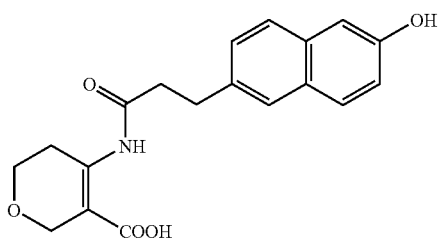

To a solution of tetrahydro-4-H-pyran-4-one (1 mL, 10.82 mmol) in anhydrous THF (50 mL) cooled to −78° C. under a nitrogen atmosphere, was added lithium diisopropylamide (6.5 mL, 13.02 mmol, 2.0 M solution). After 20 min, methyl cyanoformate (1.03 mL, 13.03 mmol) was added. The resulting mixture was slowly warmed to −20° C., and quenched with saturated ammonium chloride solution. The biphasic mixture was extracted with ethyl acetate, washed with brine and dried over anhydrous sodium sulfate. The organic layer was filtered, concentrated and purified by flash chromatography using 30% ethyl acetate hexanes to give the ketoester as a colorless oil.

To a solution of this ketoester intermediate (0.450 g, 2.85 mmol) in anhydrous THF (20 mL) cooled to 0° C., was added sodium hydride (0.171 g, 4.27 mmol, 60% by weight). After 30 min, 2-[N,N-Bis(trifluoromethylsulfonyl)amino]-5-chloropyridine (1.34 g, 3.42 mmol) was added. After stirring the reaction mixture at room temperature for 2 h, it was quenched with saturated ammonium chloride solution. The resulting mixture was extracted with ethyl acetate, and the combined organic layers were washed with brine, dried over anhydrous sodium sulfate, filtered and concentrated. The residue was purified by flash chromatography using 30% ethyl acetate-hexanes to give the enol triflate as colorless oil.

To a solution of 6-methoxy-2-naphthaldehyde (3.72 g, 20.0 mmol) in toluene (40 mL) placed in a pressure vessel, was added methyl(triphenylphosphoranylidene)acetate (6.7 g, 20 mmol). The resulting mixture was refluxed at 120° C. for 18 h. The reaction mixture was concentrated and purified using a Biotage flash 40M column with 15% ethyl acetate-hexanes as the eluant, to provide the enoate.

To a solution of this enoate (4.64 g, 19.14 mmol) in 1:1 dichloromethane-methanol (100 mL) was added Pd/C. The resulting mixture was stirred under a H$_2$ balloon for 18 h. The reaction mixture was filtered through celite and concentrated to give the methoxy ester as a white solid.

To a solution of this methyl ether intermediate (3.0 g, 12.3 mmol) in DCM (80 mL) cooled to 0° C., was added BBr$_3$ (61.5 mL, 1.0M in DCM). After 30 min, the mixture was quenched with methanol (50 mL) followed by cold water. The resulting mixture was concentrated, and the residue diluted with water and extracted with dichloromethane. The organic layer was dried over anhydrous Na$_2$SO$_4$, filtered and concentrated. This naphtholic ester was used in the next step without any further purification.

To a solution of this ester intermediate (3.0 g, 12.3 mmol) in 1,4-dioxane (50 mL) placed in a pressure tube, was added concentrated NH$_4$OH solution. The resulting mixture was stirred at RT for 18 h. The reaction mixture was concentrated and the residue was suspended in ethyl acetate, washed with water, dried over anhydrous sodium sulfate filtered and concentrated. The residue was purified by flash chromatography using 50% ethyl acetate hexanes then 100% ethyl acetate as the eluant to give the naphtholic primary carboxamide as an off-white solid.

To a solution of the enol triflate intermediate (100 mg, 0.344 mmol) in anhydrous dioxane (3 mL) was added the primary carboxamide intermediate (61 mg, 0.287 mmol), XANTPHOS (40 mg, 0.068 mmol), cesium carbonate (157 mg, 0.481 mmol) and Pd$_2$(dba)$_3$ (19 mg, 0.02 mmol). The resulting mixture was degassed for 2 min by bubbling N$_2$ gas. The reaction mixture was heated at 50° C. under a N$_2$ atmosphere for 2 h. The reaction mixture was cooled to room temperature, and filtered through celite. The filtrate was concentrated and purified by flash chromatography using 40% ethyl acetate-hexanes to give the amide product.

To a solution of this ester penultimate intermediate (44 mg) in THF (2 mL) was added 1N NaOH (1 mL) followed by MeOH (1 mL). The resulting mixture was stirred at 23° C. for 5 h. The reaction mixture was quenched by the addition of 1N HCl (1 mL). The resulting mixture was concentrated, and the residue was extracted with ethyl acetate. The combined organic layers were washed with brine, dried over anhydrous sodium sulfate, filtered and concentrated. The residue was purified by reverse phase HPLC (Gilson) to provide Example 40. $^1$H NMR (500 MHz, DMSO-d$_6$) δ 11.38 (s, 1H), 9.59 (bs, 1H), 7.65 (d, 1H), 7.56 (m, 2H), 7.28 (d, 1H), 7.05 (m, 2H), 4.16 (s, 2H), 3.65 (t, 2H), 2.9 (t, 2H), 2.86 (bt, 2H), 2.65 (t, 2H); LCMS m/z 342 (M+1).

Example 41

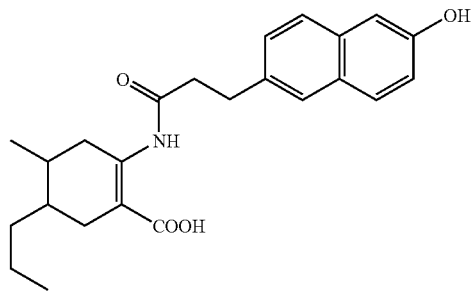

Potassium hexamethyldisilazide (35 mL of a 0.5 M solution in THF, 17.5 mmol) was added to propyl triphenylphosphonium bromide (7.1 g, 18.5 mmol) in toluene (75 mL) at 0° C. The solution was stirred for 15 min, and the ketone (2.1 g, 12.3 mmol) in toluene (50 mL) was added. The solution was stirred at 0° C. for 1 h and then heated at 100° C. overnight. Solvent was removed, and the product was purified by flash chromatography (Biotage, Horizon) 0 to 10% ethyl acetate/hexanes. The product was dissolved in methanol (150 mL) and stirred over palladium on carbon (5%, 1 g) under an atmosphere of hydrogen overnight. The solution was filtered through celite and solvent was removed. The product was dissolved in THF/MeOH/3N HCl (50 mL/20 mL/10 mL) for 36 h. The mixture was neutralized with saturated sodium bicarbonate, and the solvent was removed. The solution was washed with ethyl acetate, and the resulting organic layer was washed with brine and dried over Na$_2$SO$_4$. The product was purified by flash chromatography (Biotage, Horizon) 0 to 20% ethyl acetate/hexanes.

To a solution of the ketone (796 m g, 5.2 mmol) in anhydrous THF (25 mL) cooled to −78° C. under a N$_2$ atmosphere, was added LiHMDS (6.2 mL, 6.2 mmol, 1.0 M in THF). After 30 min, methyl cyanoformate (0.538 mL, 6.7 mmol) was added, and the reaction mixture was allowed to warm to 0° C. over several hours. The mixture was quenched with 1N HCl and extracted with EtOAc (2×). The organic layer was washed with brine and dried over Na$_2$SO$_4$, filtered and concentrated in vacuo. This material was used in the next step without any further purification.

To a solution of the ketoester (1095 mg, 5.2 mmol) in anhydrous THF (50 mL) was added NaH (309 mg, 7.7 mmol, 60%). After 15 min, 2-[N,N-Bis(trifluoromethylsulfonyl)amino]-5-chloropyridine (2.02 g, 5.2 mmol) was added. The reaction mixture was stirred at room temperature for 18 h and then quenched with water. The resulting mixture was extracted with EtOAc (2×). The organic layer was washed with brine, dried over Na$_2$SO$_4$, filtered, and concentrated in vacuo. The crude material was purified by flash chromatography (Biotage, Horizon) (0% EtOAc/Hexane to 20% EtOAc/Hexane) to give the desired product.

To a solution of the vinyl triflate (200 mg, 0.58 mmol) in anhydrous dioxane (11 mL) was added the amide (15 mg, 0.07 mmol), XANTPHOS (32 mg, 0.05 mmol), cesium carbonate (22 mg, 0.17 mmol) and Pd$_2$(dba)$_3$ (20 mg, 0.02 mmol). The resulting mixture was de-gassed for 2 min by bubbling gaseous N$_2$. The mixture was heated at 60° C. under a N$_2$ atmosphere for 18 h. The reaction mixture was cooled to room temperature, and filtered through celite. The filtrate was concentrated in vacuo, and the residue was purified by reverse phase HPLC (Gilson) to give the desired product.

To a solution of the methyl ester in dioxane (3 mL) was added MeOH (1 mL) and 1N LiOH (1 mL). The resulting mixture was stirred at room temperature for 18 h, and then neutralized to pH=7 by the addition of 1N HCl, and purified by reverse phase HPLC (Gilson) to provide Example 41. $^1$H NMR (500 MHz, DMSO-d$_6$) δ 7.65 (d, 1H), 7.58 (d, 1H), 7.56 (s, 1H), 7.28 (d, 1H), 7.06-7.02 (m, 2H), 2.97-2.88 (m, 3H), 2.65-2.63 (m, 3H), 2.45-2.33 (m, 2H), 1.84-1.71 (m, 1H), 1.65-1.62 (m, 1H), 1.51-1.15 (m, 4H), 0.901 (d, 3H), 0.86 (t, 3H); LCMS m/z 396 (M+1).

Biological Assays

The activity of the compounds of the present invention regarding niacin receptor affinity and function can be evaluated using the following assays:

$^3$H-Niacin Binding Assay:

1. Membrane: Membrane preps are stored in liquid nitrogen in:
    20 mM HEPES, pH 7.4
    0.1 mM EDTA Thaw receptor membranes quickly and place on ice. Resuspend by pipetting up and down vigorously, pool all tubes, and mix well. Use clean human at 15 µg/well, clean mouse at 10 ug/well, dirty preps at 30 ug/well.
    1a. (human): Dilute in Binding Buffer.
    1b. (human+4% serum): Add 5.7% of 100% human serum stock (stored at −20° C.) for a final concentration of 4%. Dilute in Binding Buffer.
    1c. (mouse): Dilute in Binding Buffer.
2. Wash buffer and dilution buffer: Make 10 liters of ice-cold Binding Buffer:
    20 mM HEPES, pH 7.4
    1 mM MgCl$_2$
    0.01% CHAPS (w/v)
    use molecular grade or ddH$_2$O water
3. [5,6-$^3$H]-nicotinic acid: American Radiolabeled Chemicals, Inc. (cat #ART-689). Stock is ~50 Ci/mmol, 1 mCi/ml, 1 ml total in ethanol→20 µM Make an intermediate $^3$H-niacin working solution containing 7.5% EtOH and 0.25 µM tracer. 40 µL of this will be diluted into 200 fL total in each well→1.5% EtOH, 50 nM tracer final.
4. Unlabeled nicotinic acid:
    Make 100 mM, 10 mM, and 80 µM stocks; store at −20° C. Dilute in DMSO.
5. Preparing Plates:
1) Aliquot manually into plates. All compounds are tested in duplicate. 10 mM unlabeled nicotinic acid must be included as a sample compound in each experiment.
2) Dilute the 10 mM compounds across the plate in 1:5 dilutions (8 µl:40 µl).
3) Add 195 µL binding buffer to all wells of Intermediate Plates to create working solutions (250 µM→0). There will be one Intermediate Plate for each Drug Plate.
4) Transfer 5 µL from Drug Plate to the Intermediate Plate. Mix 4-5 times.

6. Procedure:
1) Add 140 μL of appropriate diluted 19CD membrane to every well. There will be three plates for each drug plate: one human, one human+serum, one mouse.
2) Add 20 μL of compound from the appropriate intermediate plate
3) Add 40 μL of 0.25 μM $^3$H-nicotinic acid to all wells.
4) Seal plates, cover with aluminum foil, and shake at RT for 3-4 hours, speed 2, titer plate shaker.
5) Filter and wash with 8×200 μL ice-cold binding buffer. Be sure to rinse the apparatus with >1 liter of water after last plate.
6) Air dry overnight in hood (prop plate up so that air can flow through).
7) Seal the back of the plate
8) Add 40 μL Microscint-20 to each well.
9) Seal tops with sealer.
10) Count in Packard Topcount scintillation counter.
11) Upload data to calculation program, and also plot raw counts in Prism, determining that the graphs generated, and the $IC_{50}$ values agree.

The compounds of the invention generally have an $IC_{50}$ in the $^3$H-nicotinic acid competition binding assay within the range of 1 nM to about 25 μM.

$^{35}$S-GTPγS Binding Assay:

Membranes prepared from Chinese Hamster Ovary (CHO)-K1 cells stably expressing the niacin receptor or vector control (7 μg/assay) were diluted in assay buffer (100 mM HEPES, 100 mM NaCl and 10 mM $MgCl_2$, pH 7.4) in Wallac Scintistrip plates and pre-incubated with test compounds diluted in assay buffer containing 40 μM GDP (final [GDP] was 10 μM) for ~10 minutes before addition of $^{35}$S-GTPγS to 0.3 nM. To avoid potential compound precipitation, all compounds were first prepared in 100% DMSO and then diluted with assay buffer resulting in a final concentration of 3% DMSO in the assay. Binding was allowed to proceed for one hour before centrifuging the plates at 4000 rpm for 15 minutes at room temperature and subsequent counting in a TopCount scintillation counter. Non-linear regression analysis of the binding curves was performed in GraphPad Prism.

Membrane Preparation
Materials:
CHO-K1 cell culture medium: F-12 Kaighn's Modified Cell Culture Medium with 10% FBS, 2 mM L-Glutamine, 1 mM Sodium Pyruvate and 400 μg/ml G418
Membrane Scrape Buffer: 20 mM HEPES
    10 mM EDTA, pH 7.4
Membrane Wash Buffer: 20 mM HEPES
    0.1 mM EDTA, pH 7.4
Protease Inhibitor Cocktail: P-8340, (Sigma, St. Louis, Mo.)
Procedure:
    (Keep everything on ice throughout prep; buffers and plates of cells)
    Aspirate cell culture media off the 15 $cm^2$ plates, rinse with 5 mL cold PBS and aspirate.
    Add 5 ml Membrane Scrape Buffer and scrape cells. Transfer scrape into 50 mL centrifuge tube. Add 50 uL Protease Inhibitor Cocktail.
    Spin at 20,000 rpm for 17 minutes at 4° C.
    Aspirate off the supernatant and resuspend pellet in 30 mL Membrane Wash Buffer. Add 50 μL Protease Inhibitor Cocktail.
    Spin at 20,000 rpm for 17 minutes at 4° C.
    Aspirate the supernatant off the membrane pellet. The pellet may be frozen at −80° C. for later use or it can be used immediately.

Assay
Materials:
Guanosine 5'-diphosphate sodium salt (GDP, Sigma-Aldrich Catalog #87127)
Guanosine 5'-[γ$^{35}$S]thiotriphosphate, triethylammonium salt ([$^{35}$S]GTPγS, Amersham Biosciences Catalog #SJ1320, ~1000 Ci/mmol)
96 well Scintiplates (Perkin-Elmer #1450-501)
Binding Buffer: 20 mM HEPES, pH 7.4
    100 mM NaCl
    10 mM $MgCl_2$
GDP Buffer: binding buffer plus GDP, ranging from 0.4 to 40 μM, make fresh before assay
Procedure:
    (total assay volume=100 μwell)
    25 μL GDP buffer with or without compounds (final GDP 10 μM—so use 40 μM stock)
    50 μL membrane in binding buffer (0.4 mg protein/mL)
    25 μL [$^{35}$S]GTPγS in binding buffer. This is made by adding 5 μl [$^{35}$S]GTPγS stock into 10 mL binding buffer (This buffer has no GDP)
        Thaw compound plates to be screened (daughter plates with 5 μL compound @ 2 mM in 100% DMSO)
        Dilute the 2 mM compounds 1:50 with 245 μL GDP buffer to 40 μM in 2% DMSO. (Note: the concentration of GDP in the GDP buffer depends on the receptor and should be optimized to obtain maximal signal to noise; 40 μM).
        Thaw frozen membrane pellet on ice. (Note: they are really membranes at this point, the cells were broken in the hypotonic buffer without any salt during the membrane prep step, and most cellular proteins were washed away)
        Homogenize membranes briefly (few seconds—don't allow the membranes to warm up, so keep on ice between bursts of homogenization) until in suspension using a POLYTRON PT3100 (probe PT-DA 3007/2 at setting of 7000 rpm). Determine the membrane protein concentration by Bradford assay. Dilute membrane to a protein concentrations of 0.40 mg/ml in Binding Buffer. (Note: the final assay concentration is 20 μg/well).
        Add 25 μL compounds in GDP buffer per well to Scintiplate.
        Add 50 μL of membranes per well to Scintiplate.
        Pre-incubate for 5-10 minutes at room temperature. (cover plates with foil since compounds may be light sensitive)
        Add 25 μL of diluted [$^{35}$S]GTPγS. Incubate on shaker (Lab-Line model #1314, shake at setting of 4) for 60 minutes at room temperature. Cover the plates with foil since some compounds might be light sensitive.
        Assay is stopped by spinning plates sealed with plate covers at 2500 rpm for 20 minutes at 22° C.
        Read on TopCount NXT scintillation counter—35S protocol.

The compounds of the invention generally have an $EC_{50}$ in the functional in vitro GTPγS binding assay within the range of about less than 1 μM to as high as about 100 μM.

Flushing via Laser Doppler

Male C57B16 mice (~25 g) are anesthetized using 10 mg/ml/kg Nembutal sodium. When antagonists are to be administered they are co-injected with the Nembutal anesthesia. After ten minutes the animal is placed under the laser and the ear is folded back to expose the ventral side. The laser is positioned in the center of the ear and focused to an intensity of 8.4-9.0 V (with is generally ~4.5 cm above the ear). Data acquisition is initiated with a 15 by 15 image format, auto interval, 60 images and a 20 sec time delay with a medium resolution. Test compounds are administered following the 10th image via injection into the peritoneal space. Images 1-10 are considered the animal's baseline and data is normalized to an average of the baseline mean intensities.

Materials and Methods—Laser Doppler Pirimed PimII; Niacin (Sigma); Nembutal (Abbott Labs).

All patents, patent applications and publications that are cited herein are hereby incorporated by reference in their entirety. While certain preferred embodiments have been described herein in detail, numerous alternative embodiments are seen as falling within the scope of the invention.

What is claimed is:

1. A compound represented by formula I:

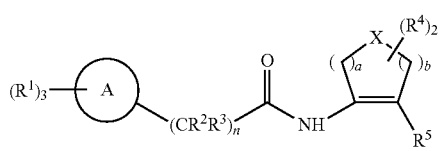

I or a pharmaceutically acceptable salt thereof is disclosed wherein:

X represents $CH_2$, $R^6$ represents $C_{1-3}$alkyl optionally substituted with 1-3 groups, 0-3 of which are halo, and 0-1 of which are selected from the group consisting of: $OC_{1-3}$alkyl, OH, $NH_2$, $NHC_{1-3}$alkyl, $N(C_{1-3}$alkyl$)_2$, CN, Hetcy, Aryl and HAR, said Aryl and HAR being further optionally substituted with 1-3 groups, 1-3 of which are halo, and 0-1 of which are selected from the group consisting of: OH, $NH_2$, $C_{1-3}$alkyl, $C_{1-3}$alkoxy, halo$C_{1-3}$alkyl and halo$C_{1-3}$alkoxy groups;

a and b are each integers 1 or 2, such that the sum of a and b is 3;

ring A is selected from the group consisting of: phenyl; naphthyl; HAR which represents a member selected from the group consisting of: pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, benzopyrazolyl, benzotriazolyl, furo(2,3-b)pyridyl, benzoxazinyl, tetrahydrohydroquinolinyl, tetrahydroisoquinolinyl, quinolyl, isoquinolyl, indolyl, dihydroindolyl, quinoxalinyl, quinazolinyl, naphthyridinyl, pteridinyl, 2,3-dihydrofuro(2,3-b)pyridyl indolinyl, dihydrobenzofuranyl, dihydrobenzothiophenyl, dihydrobenzoxazolyl, or a member selected from the group consisting of:

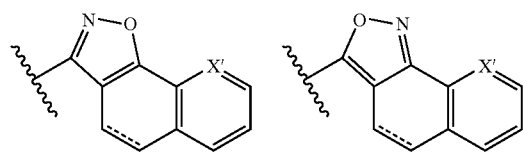

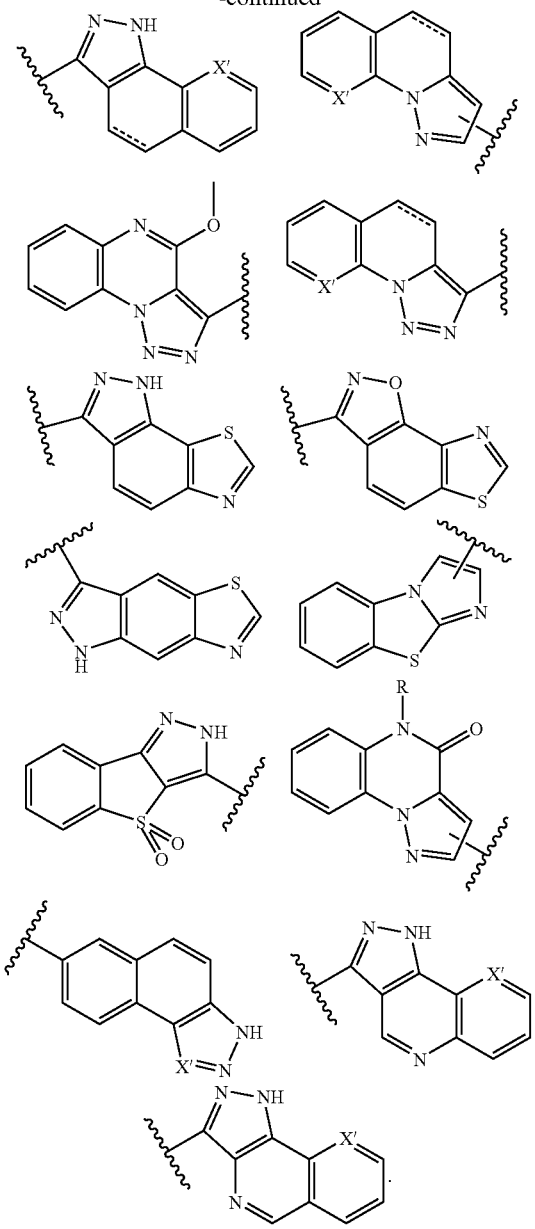

----- is a single or double bond
X' = CH or N
R = H or $CH_3$ each $R^2$ and $R^3$ is independently H, $C_{1-3}$alkyl, halo$C_{1-3}$alkyl, $OC_{1-3}$alkyl, halo$C_{1-3}$alkoxy, OH or F;

n represents an integer of from 1 to 5;

each $R^4$ is H or is independently selected from halo and $R^6$;

$R^5$ represents —$CO_2H$,

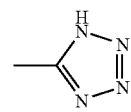

or —$C(O)NHSO_2R^e$ wherein $R^e$ represents $C_{1-4}$alkyl or phenyl, said $C_{1-4}$alkyl and phenyl each being optionally substituted with 1-3 groups, 1-3 of which are selected from halo and C$_{1-3}$alkyl, and 1-2 of which are selected from the group consisting of: OC$_{1-3}$alkyl, haloC$_{1-3}$alkyl, haloC$_{1-3}$alkoxy, OH, NH$_2$ and NHC$_{1-3}$alkyl;

and each R$^1$ is H or is independently selected from the group consisting of:
a) halo, OH,
f) phenyl or a 5-6 membered heteroaryl, said heteroaryl is pyridinyl, pyrazolyl, triazolyl, or dihydrobenzofuranyl, attached at any available ring atom and each being optionally substituted with 1-3 groups, 1-3 of which are selected from halo, OH; NH$_2$.

2. A compound in accordance with claim 1 wherein ring A is selected from the group consisting of: phenyl; naphthyl; and HAR which is a member selected from the group consisting of: isoxazolyl, pyrazolyl, oxazolyl, oxadiazolyl, thiazolyl, triazolyl, thienyl, benzothiazolyl, and a member selected from the group consisting of:

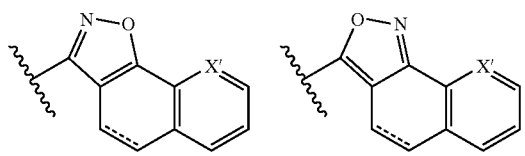

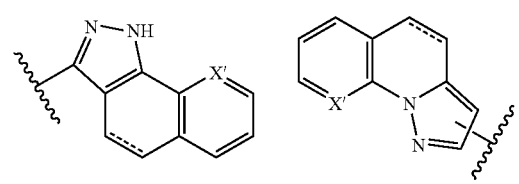

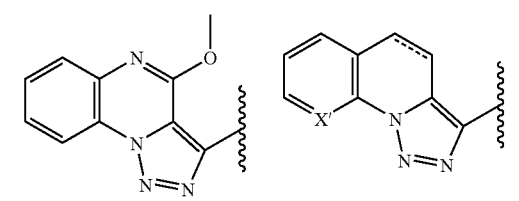

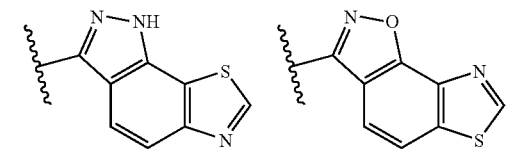

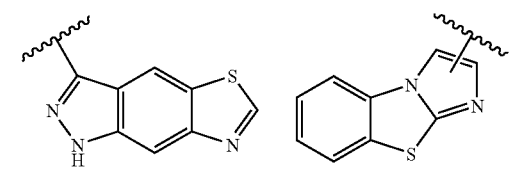

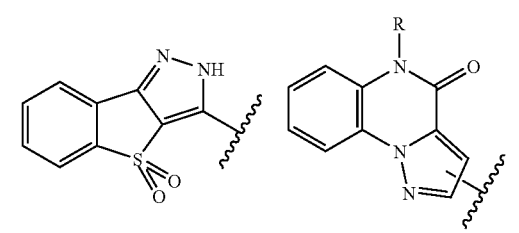

-continued

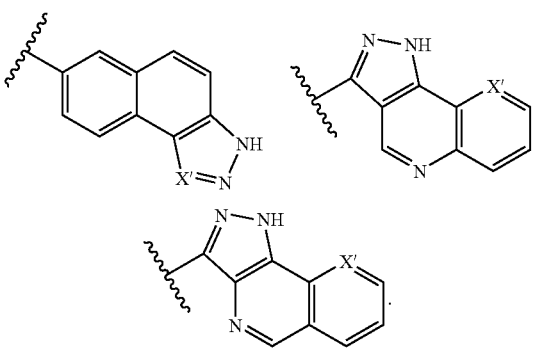

----- is a single or double bond
X' = CH or N
R = H or CH$_3$

3. A compound in accordance with claim 1 wherein R$^2$ and R$^3$ are independently H, C$_{1-3}$alkyl, OH or haloC$_{1-3}$alkyl.

4. A compound in accordance with claim 3 wherein R$^2$ and R$^3$ are independently H or methyl.

5. A compound in accordance with claim 1 wherein n represents an integer of from 2 to 4.

6. A compound in accordance with claim 5 wherein n is 2.

7. A compound in accordance with claim 1 wherein each R$^4$ is H or is independently selected from the group consisting of: halo, C$_{1-3}$alkyl optionally substituted with 1-3 halo groups or 0-1 OC$_{1-3}$alkyl groups.

8. A compound in accordance with claim 1 wherein R$^5$ represents —CO$_2$H.

9. A compound in accordance with claim 1 wherein:

ring A is selected from the group consisting of: phenyl; naphthyl; HAR which represents a member selected from the group consisting of: pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, benzopyrazolyl, benzotriazolyl, furo(2,3-b)pyridyl, benzoxazinyl, tetrahydrohydroquinolinyl, tetrahydroisoquinolinyl, quinolyl, isoquinolyl, indolyl, dihydroindolyl, quinoxalinyl, quinazolinyl, naphthyridinyl, pteridinyl, 2,3-dihydrofuro(2,3-b)pyridyl indolinyl, dihydrobenzofuranyl, dihydrobenzothiophenyl, dihydrobenzoxazolyl, or a member selected from the group consisting of:

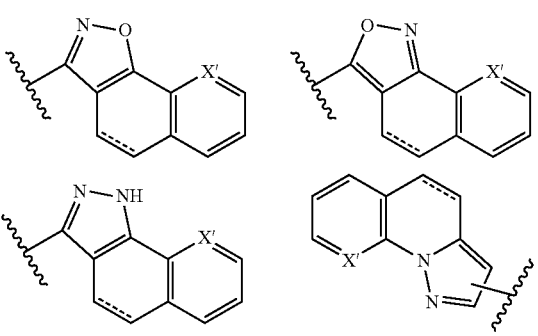

-continued

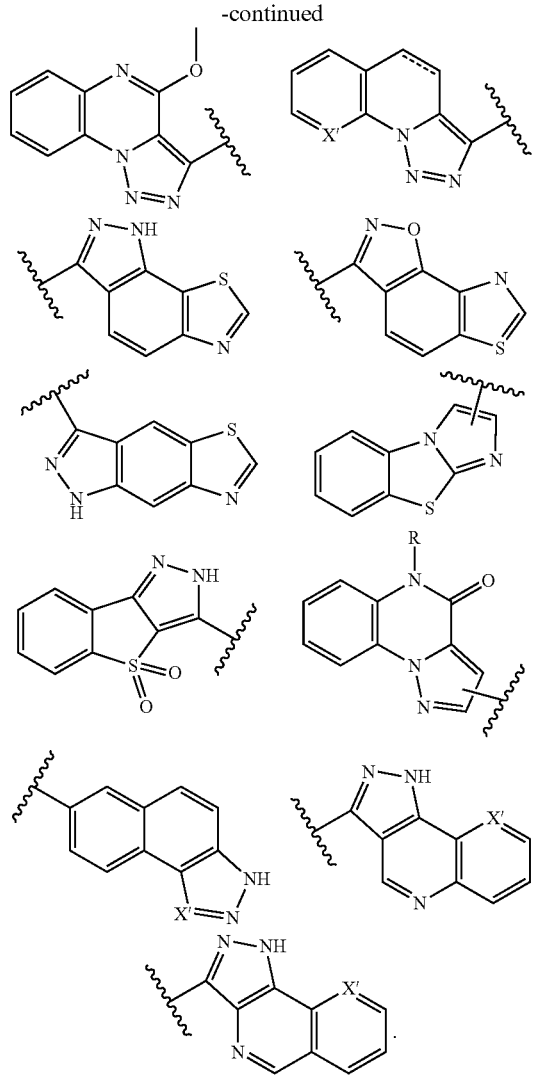
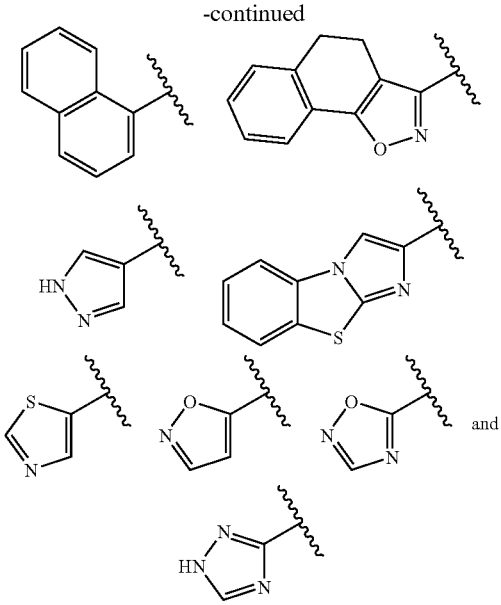

----- is a single or double bond
X' = CH or N
R = H or CH₃ a and b are 1 or 2 such that the sum of a and b is 2 or 3;

X represents O or CH₂;

$R^2$ and $R^3$ are independently H, OH, $C_{1-3}$alkyl or halo$C_{1-3}$alkyl;

n represents 2;

$R^4$ is H or is independently selected from the group consisting of: halo, $C_{1-3}$alkyl optionally substituted with 1-3 halo groups or 0-1 $OC_{1-3}$alkyl groups; and $R^5$ represents —CO₂H.

10. A compound in accordance with claim 1 wherein:
ring A is selected from the group consisting of:

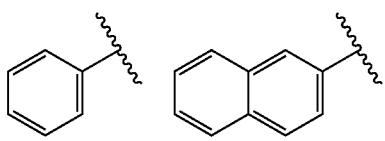

each $R^1$ is independently H, CH₃, phenyl, 4-hydroxy-phenyl, OH, 2-hydroxy-phenyl, 3-hydroxy-phenyl, 3-amino-phenyl, 2,3-dihydro-benzofuran-6-yl, 2-chloro-4-hydroxy-phenyl, 1H-pyrazol-4-yl, 5-hydroxy-pyridin-2-yl, 4-hydroxy-pyrazol-1-yl, 1H-[1,2,3]triazol-4-yl, or 5-fluoro-pyridin-2-yl;

a and b are 1 or 2 such that the sum of a and b is 2 or 3;

X represents CH₂;

each $R^2$ and $R^3$ is independently H, OH or CH₃;

n represents 2;

$R^4$ is H, CH₃, CH₂CH₃, CF₃ or CH₂OCH₃; and $R^5$ represents —CO₂H.

11. A compound in accordance with claim 1 selected from the following table:

TABLE 1

Compound 2

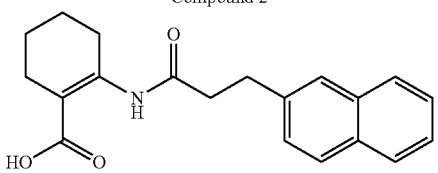

Compound 3

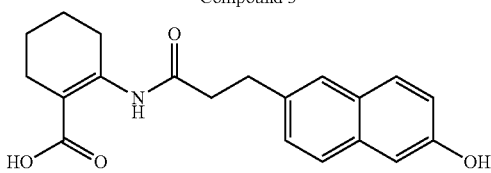

Compound 4

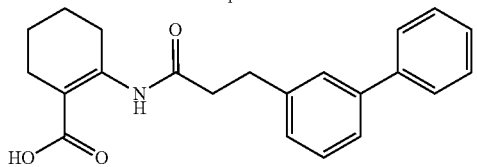

TABLE 1-continued
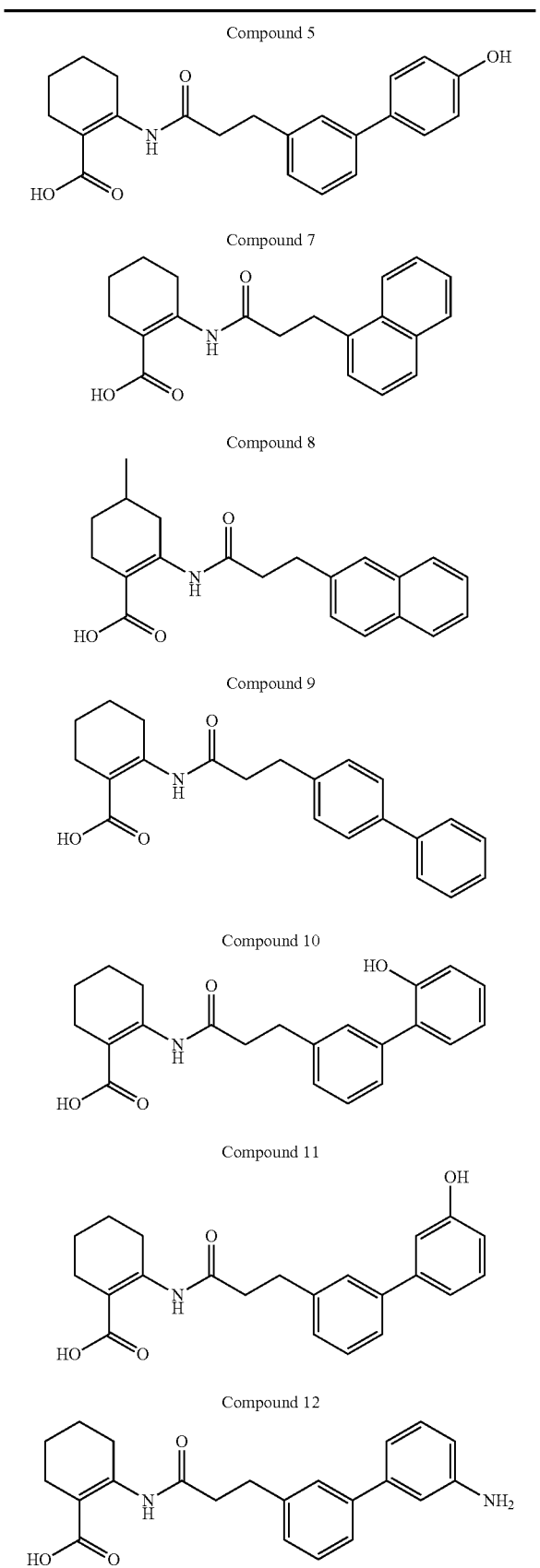
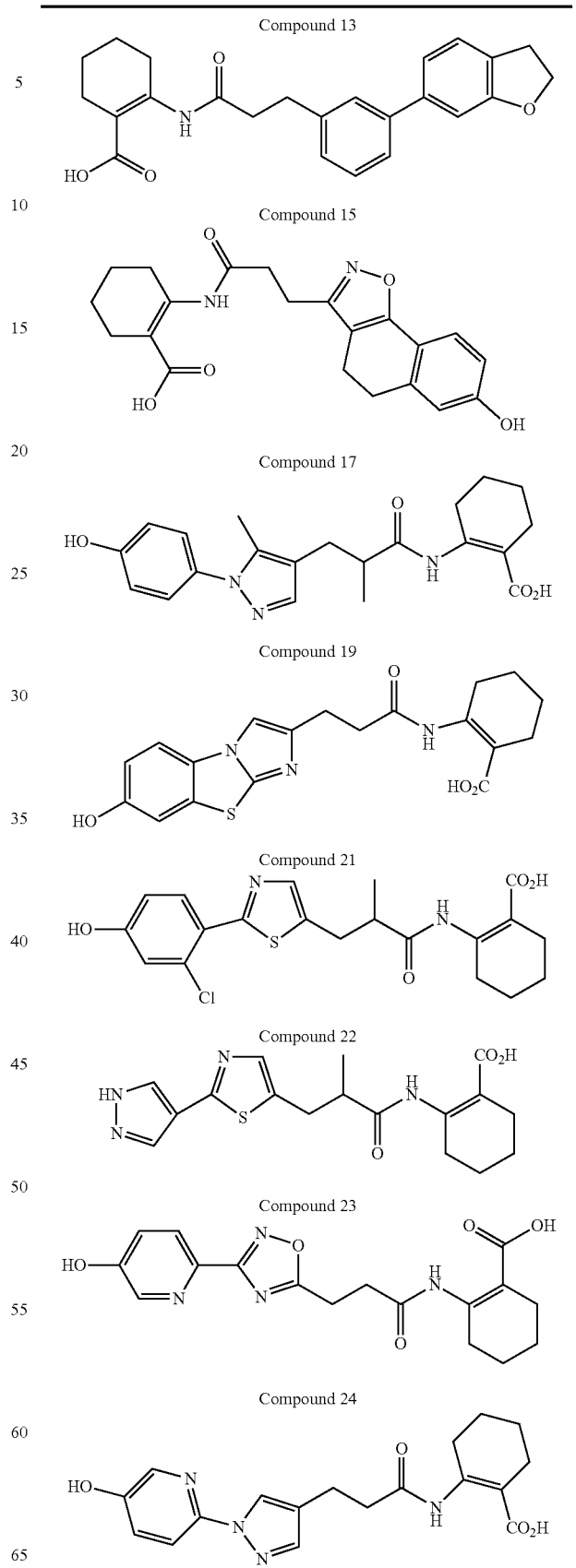

TABLE 1-continued
Compound 25
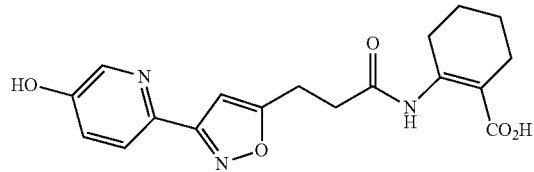
Compound 26
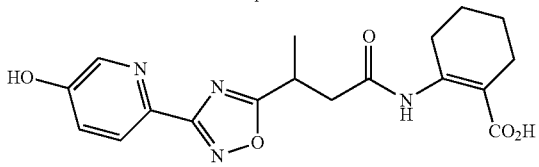
Compound 27
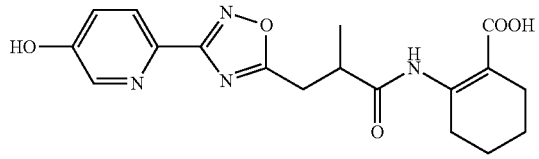
Compound 28
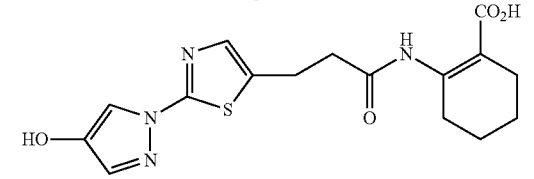
Compound 29
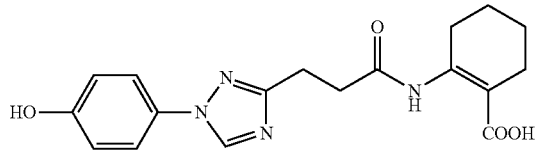
Compound 30
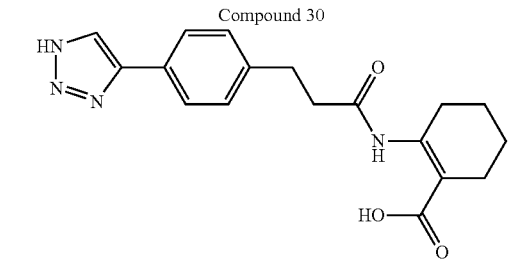
Compound 31
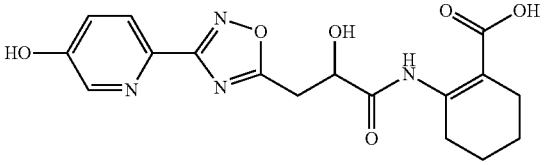
Compound 32
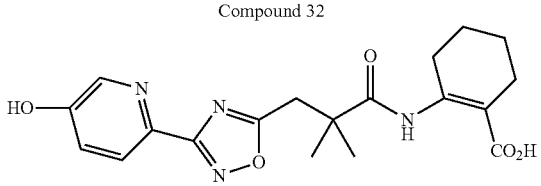
TABLE 1-continued
Compound 33
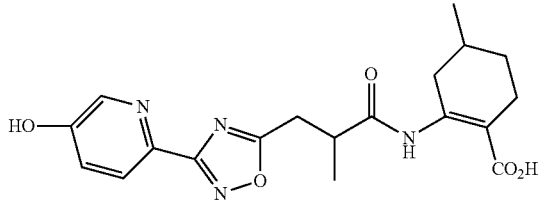
Compound 34
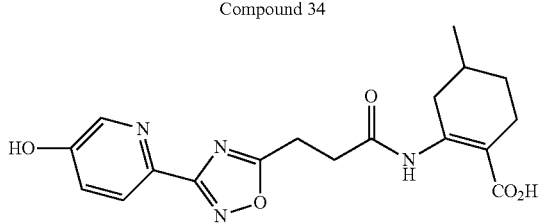
Compound 35
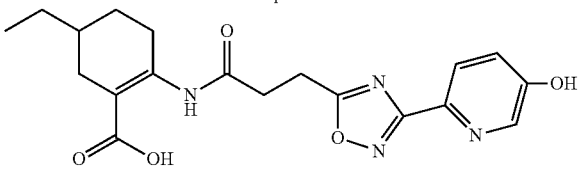
Compound 36
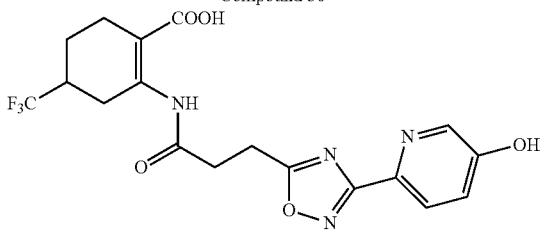
Compound 37
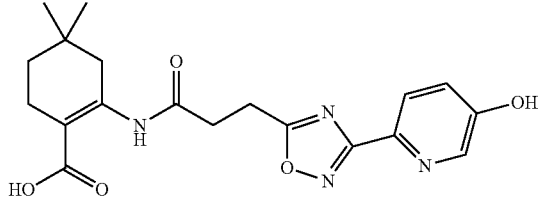
Compound 38
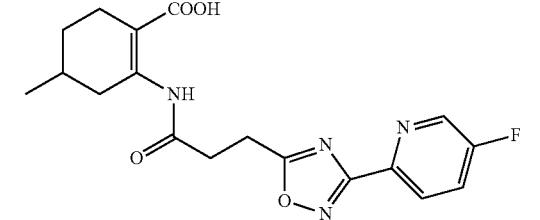

TABLE 1-continued

Compound 39

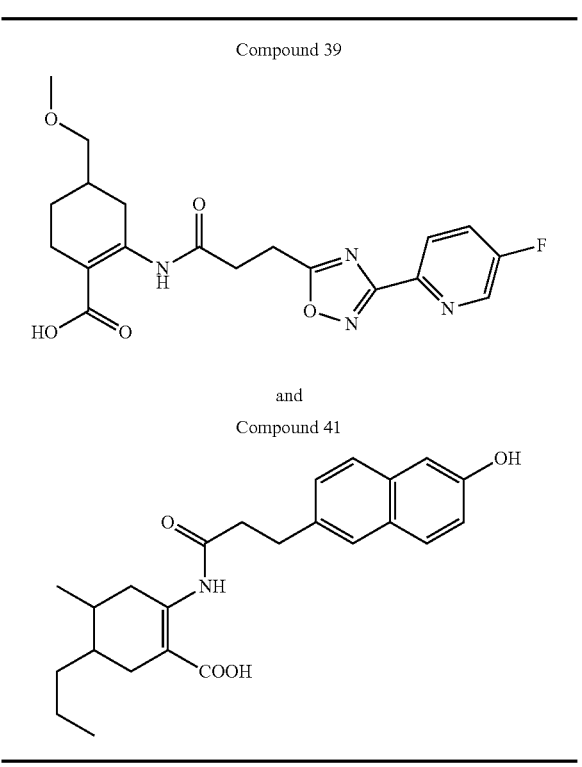

and
Compound 41

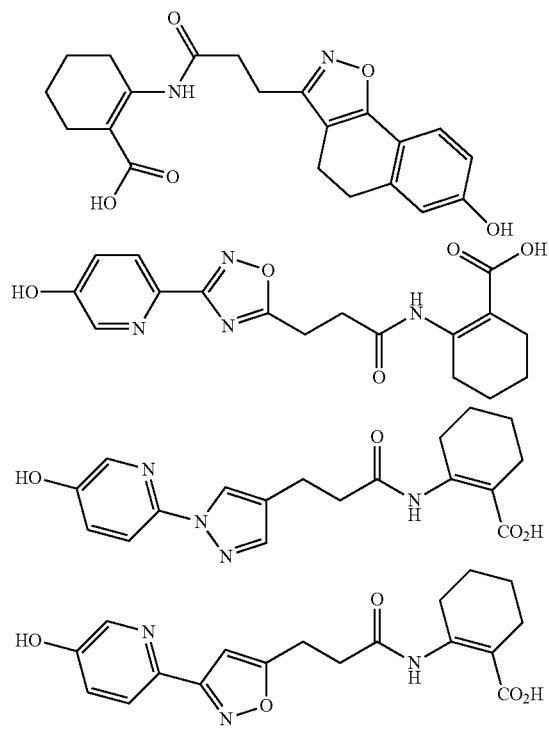

or a pharmaceutically acceptable salt thereof.

12. A pharmaceutical composition comprising a compound in accordance with claim 1 in combination with a pharmaceutically acceptable carrier.

13. The compound of claim 11

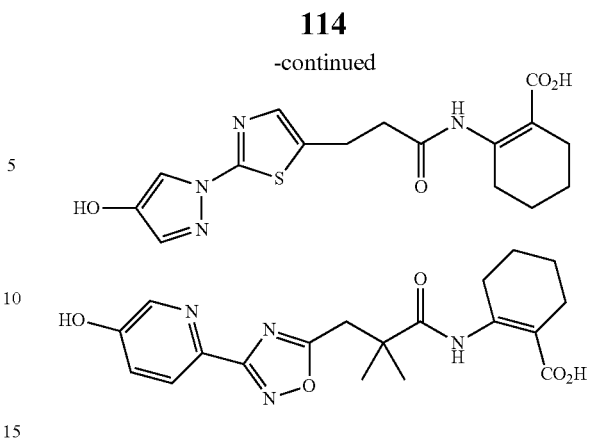

or a pharmaceutically acceptable salt thereof.

14. The compound, according to claim 13, of formula

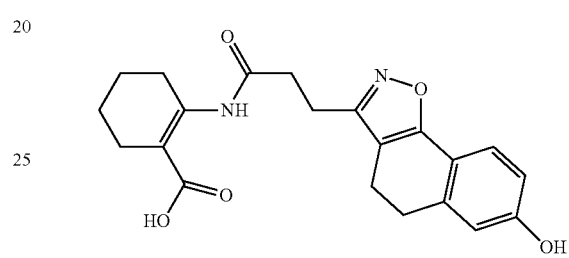

or a pharmaceutically acceptable salt thereof.

15. The compound, according to claim 13, of formula

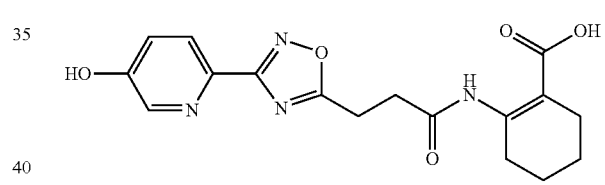

or a pharmaceutically acceptable salt thereof.

16. The compound, according to claim 13, of formula

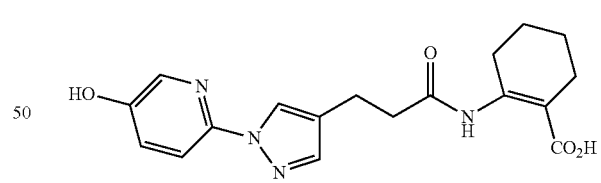

or a pharmaceutically acceptable salt thereof.

17. The compound, according to claim 13, of formula

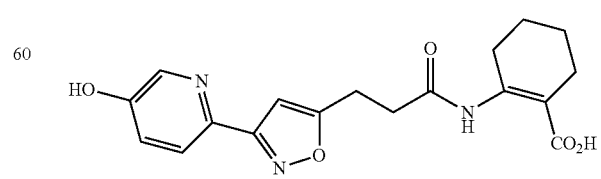

or a pharmaceutically acceptable salt thereof.

18. The compound, according to claim 13, of formula

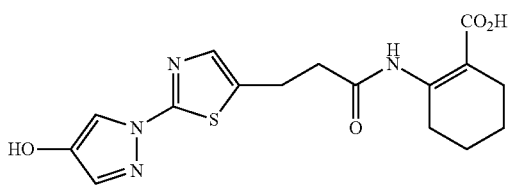

or a pharmaceutically acceptable salt thereof.

19. The compound, according to claim 13, of formula

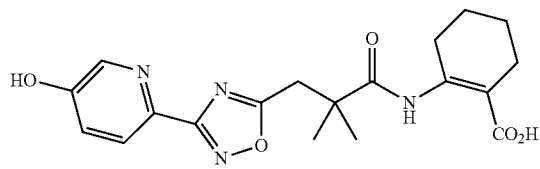

or a pharmaceutically acceptable salt thereof.

20. A pharmaceutical composition comprising a compound in accordance with claim 13 or a pharmaceutically acceptable salt thereof and DP receptor antagonist of formula:

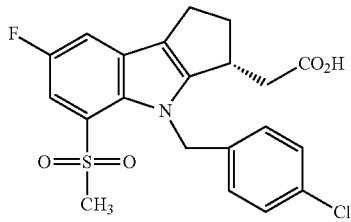

in combination with a pharmaceutically acceptable carrier.

* * * * *